US009062286B2

(12) United States Patent
Ichiyanagi et al.

(10) Patent No.: US 9,062,286 B2
(45) Date of Patent: Jun. 23, 2015

(54) AMADORIASE HAVING ALTERED SUBSTRATE SPECIFICITY

(75) Inventors: Atsushi Ichiyanagi, Chiba (JP); Kozo Hirokawa, Chiba (JP); Yasuko Tanabe, Chiba (JP); Yosuke Masakari, Chiba (JP)

(73) Assignee: Kikkoman Corporation, Chiba (JP)

( * ) Notice: Subject to any disclaimer, the term of this patent is extended or adjusted under 35 U.S.C. 154(b) by 0 days.

(21) Appl. No.: 13/814,692

(22) PCT Filed: Aug. 4, 2011

(86) PCT No.: PCT/JP2011/067898
§ 371 (c)(1),
(2), (4) Date: Feb. 6, 2013

(87) PCT Pub. No.: WO2012/018094
PCT Pub. Date: Feb. 9, 2012

(65) Prior Publication Data
US 2013/0267007 A1  Oct. 10, 2013

(30) Foreign Application Priority Data

Aug. 6, 2010  (JP) ................................. 2010-176967
Sep. 24, 2010  (JP) ................................. 2010-213070

(51) Int. Cl.
| | | |
|---|---|---|
| C12N 9/06 | (2006.01) | |
| C12N 1/00 | (2006.01) | |
| C12N 15/63 | (2006.01) | |
| G01N 33/72 | (2006.01) | |
| C12Q 1/26 | (2006.01) | |

(52) U.S. Cl.
CPC ................ *C12N 9/0032* (2013.01); *C12N 1/00* (2013.01); *C12N 15/63* (2013.01); *G01N 33/723* (2013.01); *G01N 2333/902* (2013.01); *C12Q 1/26* (2013.01)

(58) Field of Classification Search
None
See application file for complete search history.

(56) References Cited

U.S. PATENT DOCUMENTS

| | | | |
|---|---|---|---|
| 5,370,990 A | 12/1994 | Staniford et al. | |
| 6,033,867 A | 3/2000 | Kato et al. | |
| 7,018,823 B2 * | 3/2006 | Kurosawa et al. | ............ 435/189 |

(Continued)

FOREIGN PATENT DOCUMENTS

| | | |
|---|---|---|
| JP | 5-33997 B2 | 5/1993 |
| JP | 11-127895 A | 5/1999 |

(Continued)

OTHER PUBLICATIONS

GenBank Accession No. XP_002477846.1, available May 2, 2007.*

(Continued)

*Primary Examiner* — Rebecca Prouty
*Assistant Examiner* — Richard Ekstrom
(74) *Attorney, Agent, or Firm* — Foley & Lardner LLP

(57) ABSTRACT

This invention provides an amadoriase having high substrate specificity to fructosyl valyl histidine. Such amadoriase comprises substitution of one or more amino acid residues at positions corresponding to amino acids selected from the group consisting of position 98, position 259, position 154, position 125, position 261, position 263, position 106, position 103, position 355, position 96, position 66, position 67, position 70, position 100, position 110, position 113, position 114, and position 156 in the amadoriase derived from the genus *Coniochaeta*. This invention enables accurate measurement of α-fructosyl valyl histidine derived from the β-chain amino terminus in glycated hemoglobin in the presence of ε-fructosyl lysine.

9 Claims, 2 Drawing Sheets

(56) References Cited

U.S. PATENT DOCUMENTS

| | | | |
|---|---|---|---|
| 7,070,948 | B1 | 7/2006 | Sakaue et al. |
| 8,497,083 | B2 * | 7/2013 | Ikebukuro et al. ............. 435/25 |
| 8,721,853 | B2 * | 5/2014 | Ikebukuro et al. ....... 204/403.14 |
| 2003/0157593 | A1 | 8/2003 | Kurosawa et al. |
| 2008/0113381 | A1 | 5/2008 | Matsuoka et al. |
| 2008/0233605 | A1 | 9/2008 | Taniguchi et al. |
| 2009/0239239 | A1 | 9/2009 | Hirokawa et al. |
| 2011/0136202 | A1 * | 6/2011 | Hirokawa et al. ............ 435/191 |
| 2011/0195444 | A1 * | 8/2011 | Hirao et al. .................... 435/25 |

FOREIGN PATENT DOCUMENTS

| | | |
|---|---|---|
| JP | 2001-095598 A | 4/2001 |
| JP | 2003-235585 A | 8/2003 |
| JP | 2004-275013 A | 10/2004 |
| JP | 2004-275063 A | 10/2004 |
| JP | WO2007/125779 A1 | 11/2007 |
| JP | 2010-035469 A | 2/2010 |
| JP | 2010-057474 A | 3/2010 |
| JP | 2010-104278 A | 5/2010 |
| JP | 2010-115189 A | 5/2010 |
| JP | 2010-148358 A | 7/2010 |
| JP | 2010-233501 A | 10/2010 |
| JP | 2010-233502 A | 10/2010 |
| WO | WO-97/13872 A1 | 4/1997 |
| WO | WO-2004/104203 A1 | 12/2004 |
| WO | WO-2005/049857 A1 | 6/2005 |

OTHER PUBLICATIONS

Lin et al., "Occurrence, characteristics, and applications of fructosyl amine oxidases (amadoriases)", Applied Microbiology and Biotechnology, vol. 86, pp. 1613-1619, 2010.*

Guo et al., "Protein tolerance to random amino acid change", Proceedings of the National Academy of Sciences USA, vol. 101, No. 25, pp. 9205-9210, 2004.*

Supplementary European Search Report dated Jan. 29, 2014, in EP 11814719.8.

Ferri et al., "Review of Fructosyl Amino Acid Oxidase Engineering Research: A Glimpse into the Future of Hemoglobin A1c Biosensing," Journal of Diabetes Science and Technology, May 2009, 3(3):585-592.

Miura et al., "Development of fructosyl amine oxidase specific to fructosyl valine by site-directed mutagenesis," Protein Engineering, Design & Selection,, 2008, 21(4):233-239.

Delpierre, G. et al "Identification of Fructosamine Residues Deglycated by Fructosamine-3-kinase in Human Hemoglobin", The Journal of Biological Chemistry, vol. 279, No. 26, Issue of Juen 25, pp. 27613-27620, 2004.

Fujiwara, M., et al. Alteration of Substrate Specificity of Fructosyl-Amino Acid Oxidase from *Ulocladium* sp. JS-103, Journal of Bioscience and Bioengineering, vol. 102, No. 3, pp. 241-243. 2006.

Hirokawa, K., et al. "Molecular cloning and expression of novel fructosyl peptide oxidases and their application for the measurement of glycated protein.", Biochem. Biophys. Res. Commun., 2003, 311, pp. 104-111.

Kim, S., et al."Motif-Based Search for a Novel Fructosyl Peptide Oxidase From Genome Databases" Biotechnology and Bioengineering, vol. 106, No. 3, Jun. 15, 2010, pp. 358-366.

Yoshida, N. et al. "Primary structures of fungal fructosyl amino acid oxidases and their application to the measurement of glycated proteins", Eur.J. Biochem, 242, pp. 499-505(1996).

PCT/JP2011/067898 International Search Report.

* cited by examiner

```
                          SEQUENCE LISTING

<160> NUMBER OF SEQ ID NOS: 282

<210> SEQ ID NO 1
<211> LENGTH: 437
<212> TYPE: PRT
<213> ORGANISM: Coniochaeta sp.

<400> SEQUENCE: 1

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
                100                 105                 110

Ala Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335
```

| | | | | | | | | | | | | |
|---|---|---|---|---|---|---|---|---|---|---|---|---|
|Gln|Asp|Lys|Glu|Leu|Phe|Asn|Arg|Ala|Leu|Cys|Trp|Cys|Thr|Asp|Thr|
| | |340| | | | |345| | | | |350| | | |
|Ala|Asp|Ala|Ala|Leu|Leu|Met|Cys|Glu|His|Pro|Lys|Trp|Lys|Asn|Phe|
| | | |355| | | | |360| | | | |365| | |
|Ile|Leu|Ala|Thr|Gly|Asp|Ser|Gly|His|Ser|Phe|Lys|Ile|Leu|Pro|Asn|
| | |370| | | | |375| | | | |380| | | |
|Val|Gly|Lys|Tyr|Val|Val|Glu|Leu|Ile|Glu|Gly|Arg|Leu|Pro|Glu|Glu|
|385| | | | |390| | | | |395| | | | |400|
|Met|Ala|Tyr|Gln|Trp|Arg|Trp|Arg|Pro|Gly|Gly|Asp|Ala|Leu|Lys|Ser|
| | | | |405| | | | |410| | | | |415| |
|Arg|Arg|Ala|Ala|Pro|Pro|Lys|Asp|Leu|Ala|Asp|Met|Pro|Gly|Trp|Lys|
| | |420| | | | |425| | | | |430| | | |
|His|Asp|Pro|Lys|Leu| | | | | | | | | | | |
| | |435| | | | | | | | | | | | | |

```
<210> SEQ ID NO 2
<211> LENGTH: 1314
<212> TYPE: DNA
<213> ORGANISM: Coniochaeta sp.

<400> SEQUENCE: 2
atgacgtcga atcgtgcaga tacaagggtg attgtcgtcg gtggcggagg aacgattggt     60
tcctcgacag cgctgcatct tgtgaggagt ggttatgctc ccgcaaatat acggtcttg    120
gacacatttg agattccatc ggctcaatca gccggccatg atctcaacaa gatcatggga    180
atacgactgc gcaacaaggt ggacctgcaa atgagtctag aggctagaca gatgtggaag    240
gaggatgagt tattccagcc cttctttcac aataccggca gaatggactg cgaacacacg    300
cctgagggta tcgaggacct gaaaaagcag taccaggcac tgcacgatgc cggtgcgggt    360
ctggagaaga ctcatgcctg gttggacaac gaggatgaga tcttatccaa gatgccgttg    420
cttcaacgtg accaaataca aggatggaaa gcaatatgga gtcaagatgg cggctggtta    480
gctgcggcaa aggccatcaa tgcgatcgga cagttcttga agaacgtggt gtaaagttc    540
ggattcggcg cgctggatc cttcaagcaa cccctttcg acgatgaagg cacaacttgc    600
attggcgttg agacggcaga tggtaccaaa tattacgctg acaaggtggt cttagcagct    660
ggcgcatgga gcccaaccct ggtggacctg aagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag gaacatcaac cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca atggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314

<210> SEQ ID NO 3
<211> LENGTH: 31
<212> TYPE: DNA
<213> ORGANISM: Artificial Sequence
<220> FEATURE:
```

```
<223> OTHER INFORMATION: Artificially Synthesized Primer Sequence

<400> SEQUENCE: 3
gactgcgcaa cggcgtggac ctgcaaatga g                            31

<210> SEQ ID NO 4
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 4
tgcaggtcca cgccgttgcg cagtcgtatt c                            31

<210> SEQ ID NO 5
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 5
tgcgcaacaa gccggacctg caaatgag                                28

<210> SEQ ID NO 6
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 6
tttgcaggtc cggcttgttg cgcagtcg                                28

<210> SEQ ID NO 7
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 7
gactgcgcaa cggcccggac ctgcaaatg                               29

<210> SEQ ID NO 8
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 8
tttgcaggtc cgggccgttg cgcagtcg                                28

<210> SEQ ID NO 9
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 9
aaggtggacc tgccaatgag tctagag                                 27
```

-continued

```
<210> SEQ ID NO 10
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 10
tctagactca ttggcaggtc caccttg                                       27

<210> SEQ ID NO 11
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 11
ggcagaatgg cctgcgaaca cac                                           23

<210> SEQ ID NO 12
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 12
gtgttcgcag gccattctgc cg                                            22

<210> SEQ ID NO 13
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 13
agaatggact gccaacacac gcctgag                                       27

<210> SEQ ID NO 14
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 14
tcaggcgtgt gttggcagtc cattctg                                       27

<210> SEQ ID NO 15
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 15
actgcgaaca ccgtcctgag ggtatc                                        26

<210> SEQ ID NO 16
<211> LENGTH: 26
<212> TYPE: DNA
<213> ORGANISM: Artificial Sequence
<220> FEATURE:
<223> OTHER INFORMATION: Artificially Synthesized Primer Sequence
```

```
<400> SEQUENCE: 16
ataccctcag gacggtgttc gcagtc                                          26

<210> SEQ ID NO 17
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 17
acacgcctga gcgtatcgag gacctg                                          26

<210> SEQ ID NO 18
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 18
aggtcctcga tacgctcagg cgtgtg                                          26

<210> SEQ ID NO 19
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 19
agggtatcga ggccctgaaa aagcag                                          26

<210> SEQ ID NO 20
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 20 tgcttttca gggcctcgat accctc                                           26

<210> SEQ ID NO 21
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 21
acctgaaaaa ggcgtaccag gcactgcac                                       29

<210> SEQ ID NO 22
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 22
agtgcctggt acgccttttt caggtcctc                                       29

<210> SEQ ID NO 23
<211> LENGTH: 31
```

```
<212> TYPE: DNA
<213> ORGANISM: Artificial Sequence
<220> FEATURE:
<223> OTHER INFORMATION: Artificially Synthesized Primer Sequence

<400> SEQUENCE: 23
aaaaagcagt accaggaact gcacgatgcc g                                          31

<210> SEQ ID NO 24
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 24
ggcatcgtgc agttcctggt actgcttttt c                                          31

<210> SEQ ID NO 25
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 25
agtaccaggc aaagcacgat gccggtgcg                                             29

<210> SEQ ID NO 26
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 26
gcaccggcat cgtgctttgc ctggtactg                                             29

<210> SEQ ID NO 27
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 27
tggagaagac tgaagcctgg ttggac                                                26

<210> SEQ ID NO 28
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 28
tccaaccagg cttcagtctt ctccag                                                26

<210> SEQ ID NO 29
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 29
```

```
aaagcaatat gggaacaaga tggcggc                                               27

<210> SEQ ID NO 30
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 30
ccgccatctt gttcccatat tgctttc                                               27

<210> SEQ ID NO 31
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 31
aatatggagt caaaatggcg gctggttag                                             29

<210> SEQ ID NO 32
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 32
taaccagccg ccattttgac tccatattg                                             29

<210> SEQ ID NO 33
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 33
agggtgtccc agctgtgtat aatggcg                                               27

<210> SEQ ID NO 34
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 34
ccattataca cagctgggac acccttatac                                            30

<210> SEQ ID NO 35
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 35
tgtcccagtt gtggctaatg gcgaatttg                                             29

<210> SEQ ID NO 36
<211> LENGTH: 29
<212> TYPE: DNA
<213> ORGANISM: Artificial Sequence
```

```
<220> FEATURE:
<223> OTHER INFORMATION: Artificially Synthesized Primer Sequence

<400> SEQUENCE: 36
aaattcgcca ttagccacaa ctgggacac                                      29

<210> SEQ ID NO 37
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 37
ttgtgtataa tcgcgaattt ggcttc                                         26

<210> SEQ ID NO 38
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 38
aagccaaatt cgcgattata cacaac                                         26

<210> SEQ ID NO 39
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 39
agacactgcg gacaaagctc tcttgatgtg                                     30

<210> SEQ ID NO 40
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 40
acatcaagag agctttgtcc gcagtgtctg                                     30

<210> SEQ ID NO 41
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 41
ggcagaatga gctgcgaaca cac                                            23

<210> SEQ ID NO 42
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 42
gtgttcgcag ctcattctgc cg                                             22
```

```
<210> SEQ ID NO 43
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 43
ggcagaatga actgcgaaca cac                                              23

<210> SEQ ID NO 44
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 44
gtgttcgcag ttcattctgc cg                                               22

<210> SEQ ID NO 45
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 45
ggcagaatgc actgcgaaca cac                                              23

<210> SEQ ID NO 46
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 46
gtgttcgcag tgcattctgc cg                                               22

<210> SEQ ID NO 47
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 47
agaatggact gccatcacac gcctgag                                          27

<210> SEQ ID NO 48
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 48
tcaggcgtgt gatggcagtc cattctg                                          27

<210> SEQ ID NO 49
<211> LENGTH: 27
<212> TYPE: DNA
<213> ORGANISM: Artificial Sequence
<220> FEATURE:
<223> OTHER INFORMATION: Artificially Synthesized Primer Sequence
```

```
<400> SEQUENCE: 49
agaatggact gcaaacacac gcctgag                                              27

<210> SEQ ID NO 50
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 50
tcaggcgtgt gtttgcagtc cattctg                                              27

<210> SEQ ID NO 51
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 51
agaatggact gccgccacac gcctgag                                              27

<210> SEQ ID NO 52
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 52
tcaggcgtgt ggcggcagtc cattctg                                              27

<210> SEQ ID NO 53
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 53
agaatggact gcggacacac gcctgag                                              27

<210> SEQ ID NO 54
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 54
tcaggcgtgt gtccgcagtc cattctg                                              27

<210> SEQ ID NO 55
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 55
agaatggact gcgcacacac gcctgag                                              27

<210> SEQ ID NO 56
```

```
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 56
tcaggcgtgt gtgcgcagtc cattctg                                              27

<210> SEQ ID NO 57
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 57
agaatggact gcgtacacac gcctgag                                              27

<210> SEQ ID NO 58
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 58
tcaggcgtgt gtacgcagtc cattctg                                              27

<210> SEQ ID NO 59
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 59
agaatggact gcattcacac gcctgag                                              27

<210> SEQ ID NO 60
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 60
tcaggcgtgt gaatgcagtc cattctg                                              27

<210> SEQ ID NO 61
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 61
agaatggact gcttacacac gcctgag                                              27

<210> SEQ ID NO 62
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 62
```
tcaggcgtgt gtaagcagtc cattctg    27

<210> SEQ ID NO 63
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 63
agaatggact gcatgcacac gcctgag    27

<210> SEQ ID NO 64
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 64
tcaggcgtgt gcatgcagtc cattctg    27

<210> SEQ ID NO 65
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 65
agaatggact gctgccacac gcctgag    27

<210> SEQ ID NO 66
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 66
tcaggcgtgt ggcagcagtc cattctg    27

<210> SEQ ID NO 67
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 67
agaatggact gctcacacac gcctgag    27

<210> SEQ ID NO 68
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 68
tcaggcgtgt gtgagcagtc cattctg    27

<210> SEQ ID NO 69
<211> LENGTH: 27
<212> TYPE: DNA

```
<213> ORGANISM: Artificial Sequence
<220> FEATURE:
<223> OTHER INFORMATION: Artificially Synthesized Primer Sequence

<400> SEQUENCE: 69
agaatggact gcacacacac gcctgag                                           27

<210> SEQ ID NO 70
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 70
tcaggcgtgt gtgtgcagtc cattctg                                           27

<210> SEQ ID NO 71
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 71
agaatggact gcaaccacac gcctgag                                           27

<210> SEQ ID NO 72
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 72
tcaggcgtgt ggttgcagtc cattctg                                           27

<210> SEQ ID NO 73
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 73
agaatggact gcgatcacac gcctgag                                           27

<210> SEQ ID NO 74
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 74
tcaggcgtgt gatcgcagtc cattctg                                           27

<210> SEQ ID NO 75
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 75
agaatggact gctttcacac gcctgag                                           27
```

<210> SEQ ID NO 76
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 76
tcaggcgtgt gaaagcagtc cattctg                                27

<210> SEQ ID NO 77
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 77
agaatggact gctatcacac gcctgag                                27

<210> SEQ ID NO 78
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 78
tcaggcgtgt gatagcagtc cattctg                                27

<210> SEQ ID NO 79
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 79
agaatggact gctggcacac gcctgag                                27

<210> SEQ ID NO 80
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 80
tcaggcgtgt gccagcagtc cattctg                                27

<210> SEQ ID NO 81
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 81
agaatggact gcccacacac gcctgag                                27

<210> SEQ ID NO 82
<211> LENGTH: 27
<212> TYPE: DNA
<213> ORGANISM: Artificial Sequence
<220> FEATURE:

```
<223> OTHER INFORMATION: Artificially Synthesized Primer Sequence

<400> SEQUENCE: 82
tcaggcgtgt gtgggcagtc cattctg                                              27

<210> SEQ ID NO 83
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 83
acacgcctga gaaaatcgag gacctg                                               26

<210> SEQ ID NO 84
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 84
aggtcctcga ttttctcagg cgtgtg                                               26

<210> SEQ ID NO 85
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 85
agggtatcga gggcctgaaa aagcag                                               26

<210> SEQ ID NO 86
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 86
tgcttttTCa ggccctcgat accctc                                               26

<210> SEQ ID NO 87
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 87
agggtatcga gagcctgaaa aagcag                                               26

<210> SEQ ID NO 88
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 88
tgcttttTCa ggctctcgat accctc                                               26
```

```
<210> SEQ ID NO 89
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 89
agggtatcga gaccctgaaa aagcag                                              26

<210> SEQ ID NO 90
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 90 tgcttttttca gggtctcgat accctc                                              26

<210> SEQ ID NO 91
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 91
agggtatcga gaacctgaaa aagcag                                              26

<210> SEQ ID NO 92
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 92 tgcttttttca ggttctcgat accctc                                              26

<210> SEQ ID NO 93
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 93
agggtatcga gtgcctgaaa aagcag                                              26

<210> SEQ ID NO 94
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 94 tgcttttttca ggcactcgat accctc                                              26

<210> SEQ ID NO 95
<211> LENGTH: 26
<212> TYPE: DNA
<213> ORGANISM: Artificial Sequence
<220> FEATURE:
<223> OTHER INFORMATION: Artificially Synthesized Primer Sequence
```

```
<400> SEQUENCE: 95
agggtatcga ggtcctgaaa aagcag                                          26

<210> SEQ ID NO 96
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 96 tgcttttca ggacctcgat accctc                                           26

<210> SEQ ID NO 97
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 97
agggtatcga gctgctgaaa aagcag                                          26

<210> SEQ ID NO 98
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 98 tgcttttca gcagctcgat accctc                                           26

<210> SEQ ID NO 99
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 99
agggtatcga gatcctgaaa aagcag                                          26

<210> SEQ ID NO 100
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 100 tgcttttca ggatctcgat accctc                                           26

<210> SEQ ID NO 101
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 101
acctgaaaaa gctgtaccag gcactgcac                                       29

<210> SEQ ID NO 102
<211> LENGTH: 29
```

```
<212> TYPE: DNA
<213> ORGANISM: Artificial Sequence
<220> FEATURE:
<223> OTHER INFORMATION: Artificially Synthesized Primer Sequence

<400> SEQUENCE: 102
agtgcctggt acagctttt caggtcctc                                29

<210> SEQ ID NO 103
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 103
acctgaaaaa gatgtaccag gcactgcac                               29

<210> SEQ ID NO 104
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 104
agtgcctggt acatctttt caggtcctc                                29

<210> SEQ ID NO 105
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 105
acctgaaaaa gttctaccag gcactgcac                               29

<210> SEQ ID NO 106
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 106
agtgcctggt agaactttt caggtcctc                                29

<210> SEQ ID NO 107
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 107
acctgaaaaa gtggtaccag gcactgcac                               29

<210> SEQ ID NO 108
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 108
```
agtgcctggt accactttt caggtcctc                               29

<210> SEQ ID NO 109
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 109
acctgaaaaa gaactaccag gcactgcac                              29

<210> SEQ ID NO 110
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 110
agtgcctggt agttctttt caggtcctc                               29

<210> SEQ ID NO 111
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 111
acctgaaaaa gcactaccag gcactgcac                              29

<210> SEQ ID NO 112
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 112
agtgcctggt agtgctttt caggtcctc                               29

<210> SEQ ID NO 113
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 113
acctgaaaaa gaagtaccag gcactgcac                              29

<210> SEQ ID NO 114
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 114
agtgcctggt acttctttt caggtcctc                               29

<210> SEQ ID NO 115
<211> LENGTH: 29
<212> TYPE: DNA
<213> ORGANISM: Artificial Sequence

```
<220> FEATURE:
<223> OTHER INFORMATION: Artificially Synthesized Primer Sequence

<400> SEQUENCE: 115
acctgaaaaa gcgctaccag gcactgcac                                              29

<210> SEQ ID NO 116
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 116
agtgcctggt agcgcttttt caggtcctc                                              29

<210> SEQ ID NO 117
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 117
acctgaaaaa ggagtaccag gcactgcac                                              29

<210> SEQ ID NO 118
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 118
agtgcctggt actccttttt caggtcctc                                              29

<210> SEQ ID NO 119
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 119
aaaaagcagt accagaaact gcacgatgcc g                                           31

<210> SEQ ID NO 120
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 120
ggcatcgtgc agtttctggt actgcttttt c                                           31

<210> SEQ ID NO 121
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 121
agtaccaggc acgtcacgat gccggtgcg                                              29
```

<210> SEQ ID NO 122
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 122
gcaccggcat cgtgacgtgc ctggtactg                              29

<210> SEQ ID NO 123
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 123
agtaccaggc agagcacgat gccggtgcg                              29

<210> SEQ ID NO 124
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 124
gcaccggcat cgtgctctgc ctggtactg                              29

<210> SEQ ID NO 125
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 125
tggagaagac taatgcctgg ttggac                                 26

<210> SEQ ID NO 126
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 126
tccaaccagg cattagtctt ctccag                                 26

<210> SEQ ID NO 127
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 127
tggagaagac taaagcctgg ttggac                                 26

<210> SEQ ID NO 128
<211> LENGTH: 26
<212> TYPE: DNA
<213> ORGANISM: Artificial Sequence
<220> FEATURE:
<223> OTHER INFORMATION: Artificially Synthesized Primer Sequence

```
<400> SEQUENCE: 128
tccaaccagg ctttagtctt ctccag                                          26

<210> SEQ ID NO 129
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 129
tggagaagac tgctgcctgg ttggac                                          26

<210> SEQ ID NO 130
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 130
tccaaccagg cagcagtctt ctccag                                          26

<210> SEQ ID NO 131
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 131
tggagaagac tcaagcctgg ttggac                                          26

<210> SEQ ID NO 132
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 132
tccaaccagg cttgagtctt ctccag                                          26

<210> SEQ ID NO 133
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 133
tggagaagac tcgtgcctgg ttggac                                          26

<210> SEQ ID NO 134
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 134
tccaaccagg cacgagtctt ctccag                                          26

<210> SEQ ID NO 135
```

```
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 135
aaagcaatat ggggtcaaga tggcggc                                              27

<210> SEQ ID NO 136
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 136
ccgccatctt gacccatat tgctttc                                               27

<210> SEQ ID NO 137
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 137
aaagcaatat ggtatcaaga tggcggc                                              27

<210> SEQ ID NO 138
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 138
ccgccatctt gataccatat tgctttc                                              27

<210> SEQ ID NO 139
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 139
aaagcaatat ggaatcaaga tggcggc                                              27

<210> SEQ ID NO 140
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 140
ccgccatctt gattccatat tgctttc                                              27

<210> SEQ ID NO 141
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 141
```
aaagcaatat ggcagcaaga tggcggc                                              27

<210> SEQ ID NO 142
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 142
ccgccatctt gctgccatat tgctttc                                              27

<210> SEQ ID NO 143
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 143
aaagcaatat gggatcaaga tggcggc                                              27

<210> SEQ ID NO 144
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 144
ccgccatctt gatcccatat tgctttc                                              27

<210> SEQ ID NO 145
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 145
aaagcaatat ggcatcaaga tggcggc                                              27

<210> SEQ ID NO 146
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 146
ccgccatctt gatgccatat tgctttc                                              27

<210> SEQ ID NO 147
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 147
aaagcaatat gggctcaaga tggcggc                                              27

<210> SEQ ID NO 148
<211> LENGTH: 27
<212> TYPE: DNA

-continued

<213> ORGANISM: Artificial Sequence
<220> FEATURE:
<223> OTHER INFORMATION: Artificially Synthesized Primer Sequence

<400> SEQUENCE: 148
ccgccatctt gagcccatat tgctttc        27

<210> SEQ ID NO 149
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 149
aaagcaatat ggtgtcaaga tggcggc        27

<210> SEQ ID NO 150
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 150
ccgccatctt gacaccatat tgctttc        27

<210> SEQ ID NO 151
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 151
agggtgtccc atgtgtgtat aatggcg        27

<210> SEQ ID NO 152
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 152
ccattataca cacatgggac acccttatac        30

<210> SEQ ID NO 153
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 153
agggtgtccc aagtgtgtat aatggcg        27

<210> SEQ ID NO 154
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 154
ccattataca cacttgggac acccttatac        30

<210> SEQ ID NO 155
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 155
tgtcccagtt gtgttaaatg gcgaatttg                                29

<210> SEQ ID NO 156
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 156
aaattcgcca tttaacacaa ctgggacac                                29

<210> SEQ ID NO 157
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 157
tgtcccagtt gtgtttaatg gcgaatttg                                29

<210> SEQ ID NO 158
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 158
aaattcgcca ttaaacacaa ctgggacac                                29

<210> SEQ ID NO 159
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 159
tgtcccagtt gtgtggaatg gcgaatttg                                29

<210> SEQ ID NO 160
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 160
aaattcgcca ttccacacaa ctgggacac                                29

<210> SEQ ID NO 161
<211> LENGTH: 29
<212> TYPE: DNA
<213> ORGANISM: Artificial Sequence
<220> FEATURE:

```
<223> OTHER INFORMATION: Artificially Synthesized Primer Sequence

<400> SEQUENCE: 161
tgtcccagtt gtgaaaaatg gcgaatttg                                          29

<210> SEQ ID NO 162
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 162
aaattcgcca tttttcacaa ctgggacac                                          29

<210> SEQ ID NO 163
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 163
ttgtgtataa taaagaattt ggcttc                                             26

<210> SEQ ID NO 164
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 164
aagccaaatt ctttattata cacaac                                             26

<210> SEQ ID NO 165
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 165
agacactgcg gaccgtgctc tcttgatgtg                                         30

<210> SEQ ID NO 166
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 166
acatcaagag agcacggtcc gcagtgtctg                                         30

<210> SEQ ID NO 167
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 167
agacactgcg gaccatgctc tcttgatgtg                                         30
```

```
<210> SEQ ID NO 168
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 168
acatcaagag agcatggtcc gcagtgtctg                                        30

<210> SEQ ID NO 169
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 169
cgccatatga cgccccgagc caacaccaaa                                        30

<210> SEQ ID NO 170
<211> LENGTH: 33
<212> TYPE: DNA
<213> ORGANISM: Artificial Sequence
<220> FEATURE:
<223> OTHER INFORMATION: Artificially Synthesized Primer Sequence

<400> SEQUENCE: 170
cgcggatccc tacatctttg cctcattcct cca                                    33

<210> SEQ ID NO 171
<211> LENGTH: 1317
<212> TYPE: DNA
<213> ORGANISM: Aspergillus nidulans

<400> SEQUENCE: 171
atgacgcccc gagccaacac caaaatcatt gtcgtcggcg gcggcggcac aatgggctcg       60
tcgacagccc tacacctcct gcgcgccggc tacacgccgt ccaacattac agtgctcgac      120
acgtgcccta tccccctccgc acagtctgca ggctacgacc tgaacaaaat catgagcatc      180
aggctgcgca acaagcctga tttacagctc tctcttgagg cgctggacat gtggaaaaat      240
gatcctctct tcaagccgtt tttccacaat gttggaatga tcgacgtctc ttcaacagag      300
gaaggcatcg agggtcttcg gaagaaatac cagtctcttc tcgacgcagg cattgggctc      360
gagaagacga atttcatgct ggaaagtgaa gacgagatcc tggctaaagc gccgcatttc      420
acgcaggagc agattaaagg ctggaaaggc ctgttctgtg gcgacggcgg ctggctcgct      480
gcagccaaag ccatcaatgc cattgggcag ttcctcaagg aacagggcgt caagtttgga      540
ttcggcggcg ccggcacgtt caaaaagcca ctcttcgccg atgcccacga aagacgtgc       600 atcggcgtcg agactgtaga cggcacaaag tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt ataagaacac tcctgttata      780
tacgacggtg actatgggtt tttctttgag ccgaatgaaa acggcatcat aaaagtctgt      840
gacgaattcc ctggcttcac gcatttcaaa atgcaccagc cgtacggctc gccggcgccc      900
aaacccatct ctgtgcctcg ttcccatgcg aagcacccca cagatacata cccgcacgcg      960
tcggaggtca cgatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
```

```
gagcatccac gctggaaggg gttttatctt gcaacagggg acagtgggca ttcgttcaag    1140
ttgctgccga atattggaaa gcatgttgtc gagttattgg aggagaggct ggaaagtgtg    1200
tttaaggatg cttggaggtg gaggcctggc agtggggatg cattaaaaag tagacgggct    1260
gcgcctgcga aggacctggc ggatatgccg gggtggagga atgaggcaaa gatgtag      1317
```

```
<210> SEQ ID NO 172
<211> LENGTH: 438
<212> TYPE: PRT
<213> ORGANISM: Aspergillus nidulans

<400> SEQUENCE: 172

Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Cys Pro Ile Pro Ser Ala Gln
            35                  40                  45

Ser Ala Gly Tyr Asp Leu Asn Lys Ile Met Ser Ile Arg Leu Arg Asn
        50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Glu Gly Ile Glu Gly Leu Arg Lys Lys Tyr Gln Ser
                100                 105                 110

Leu Leu Asp Ala Gly Ile Gly Leu Glu Lys Thr Asn Phe Met Leu Glu
            115                 120                 125

Ser Glu Asp Glu Ile Leu Ala Lys Ala Pro His Phe Thr Gln Glu Gln
        130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335
```

```
Asn Asp Lys Glu Leu Phe Asn Arg Ala Met Cys Trp Cys Thr Asp Thr
                340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435
```

<210> SEQ ID NO 173
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 173
aacaaaatca tggggatccg tctgcgcaac                                    30

<210> SEQ ID NO 174
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 174
gttgcgcaga cggatcccca tgattttgtt                                    30

<210> SEQ ID NO 175
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 175
aaaggcctgt tcgatggcga cggcggc                                       27

<210> SEQ ID NO 176
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 176
gccgccgtcg ccatcgaaca ggccttt                                       27

<210> SEQ ID NO 177
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 177

-continued aagaacactc ctgctatata cgacggtga                                           29

<210> SEQ ID NO 178
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 178
gtcaccgtcg tatatagcag gagtgttctt                                          30

<210> SEQ ID NO 179
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 179
aagaacactc cttgtatata cgacggtgac                                          30

<210> SEQ ID NO 180
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 180
gtcaccgtcg tatatacaag gagtgttctt                                          30

<210> SEQ ID NO 181
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 181
gttatatacg acaaggacta tgggttttc                                           30

<210> SEQ ID NO 182
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 182
gaaaaaccca tagtccttgt cgtatataac                                          30

<210> SEQ ID NO 183
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 183
gttatatacg accgtgacta tgggttttc                                           30

<210> SEQ ID NO 184
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 184
gaaaaaccca tagtcacggt cgtatataac                                30

<210> SEQ ID NO 185
<211> LENGTH: 33
<212> TYPE: DNA
<213> ORGANISM: Artificial Sequence
<220> FEATURE:
<223> OTHER INFORMATION: Artificially Synthesized Primer Sequence

<400> SEQUENCE: 185
aaaaaacata tggctcattc gcgagaaagc aca                             33

<210> SEQ ID NO 186
<211> LENGTH: 36
<212> TYPE: DNA
<213> ORGANISM: Artificial Sequence
<220> FEATURE:
<223> OTHER INFORMATION: Artificially Synthesized Primer Sequence

<400> SEQUENCE: 186
aaaaaaggat cctcagagct tcgcatcatg cttcca                          36

<210> SEQ ID NO 187
<211> LENGTH: 1314
<212> TYPE: DNA
<213> ORGANISM: Penicillium chrysogenum

<400> SEQUENCE: 187
atggctcatt cgcgagaaag cacaaagatt gtcattgtcg ggggaggtgg cacaatggga      60
tcttcaaccg cgctacacct gatacgctct ggatacaccc cgtcaaacat caccgtcctt     120
gatgtatacc caattccatc cttgcaatcc gcaggatatg atcttaacaa gatcatgagc     180
atccgattac gcaacgggcc tgactggcaa cttttcctgg aggctctcga tatgtggaaa     240
aacgatccgt tgttcaagcc tttctttcac aacgttggca tgctagactg ttcatcgtca     300
caagagggta ttgcaagcct tcgacggaag caccaagacc tcatagacgc gaatatcgga     360
ctagagaaga cgaatatctg gttagagagt gaagatgata ttctggcaaa agccccgcac     420
ttcgcgcggg aacagatcaa ggggtggaag ggcttgtttt cgggcgatgg aggatggctt     480
gctgcagcca aggccatcaa tgcgatcgga acctttctaa aaagtcaagg cgtcaagttc     540
ggatttggaa gtgccgggac tttcaagcga cctttgtttg ctccagatgg ggcgacatgc     600
agcggtgttg agacagtaga tggaacaaaa tacttcgccg acaaggtggt tttggccgct     660
ggtgcttgga gttcgacgtt agtagatttg gaggaccaat gtgtttcgaa ggcctgggtc     720
ttcgctcata tccaactcac gccccaagaa tcggcccagt acaaggacgt gcccgtagta     780
tacgacggtg attatggctt tttcttcgag cccaacgaac acgagtaat caaagtctgc     840
gatgagttcc ccgggttctc ccgcttcaag ctgcatcaac cttacggtgc cacctctcct     900
aagcttatat ccgttcctcg atcacacgcc aagcatccca ccgataccta cccagattct     960
tctgaagaga ccattcgaaa agcgattgcg aggtttatgc cacgcttcaa ggataaggag    1020
cttttaata ggagcatgtg ctggtgcacc gatactgctg atgccaactt gttgatctgc    1080
gagcacccca gtggaagaa ctttatcttg gccacaggag acagcggcca tagtttcaag    1140
gttttgccca atataggaaa acatgtcgtt gagttgatag aaggacgcct accacaagac    1200

```
ctggctggtg cgtggagatg gagaccaggg ggagatgccc ttaagtccaa acgcagtgct   1260
ccggcaaagg accttgctga aatgccgggc tggaagcatg atgcgaagct ctga         1314
```

<210> SEQ ID NO 188
<211> LENGTH: 437
<212> TYPE: PRT
<213> ORGANISM: Penicillium chrysogenum

<400> SEQUENCE: 188

```
Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
    50                  55                  60

Asn Gly Pro Asp Trp Gln Leu Ser Leu Glu Ala Leu Asp Met Trp Lys
65                  70                  75                  80

Asn Asp Pro Leu Phe Lys Pro Phe His Asn Val Gly Met Leu Asp
                85                  90                  95

Cys Ser Ser Gln Glu Gly Ile Ala Ser Leu Arg Arg Lys His Gln
                100                 105                 110

Asp Leu Ile Asp Ala Asn Ile Gly Leu Glu Lys Thr Asn Ile Trp Leu
            115                 120                 125

Glu Ser Glu Asp Ile Leu Ala Lys Ala Pro His Phe Ala Arg Glu
130                 135                 140

Gln Ile Lys Gly Trp Lys Gly Leu Phe Cys Gly Asp Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
        195                 200                 205

Thr Lys Tyr Phe Ala Asp Lys Val Val Leu Ala Ala Gly Ala Trp Ser
    210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Glu Pro Asn
            260                 265                 270

Glu His Gly Val Ile Lys Val Cys Asp Glu Phe Pro Gly Phe Ser Arg
        275                 280                 285

Phe Lys Leu His Gln Pro Tyr Gly Ala Thr Ser Pro Lys Leu Ile Ser
    290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
```

```
                355                 360                 365
Ile Leu Ala Thr Gly Asp Ser Gly His Ser Phe Lys Val Leu Pro Asn
        370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu
        435

<210> SEQ ID NO 189
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 189
aacaagatca tggggatccg attacgc                                         27

<210> SEQ ID NO 190
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 190
gcgtaatcgg atccccatga tcttgtt                                         27

<210> SEQ ID NO 191
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 191
agccttcgac gtcgacacca agacctc                                         27

<210> SEQ ID NO 192
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 192
gaggtcttgg tgtcgacgtc gaaggct                                         27

<210> SEQ ID NO 193
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 193
aagggcttgt ttgacggcga tggagga                                         27

<210> SEQ ID NO 194
```

```
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 194
tcctccatcg ccgtcaaaca agcccgtt                                           27

<210> SEQ ID NO 195
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 195
gtagtatacg acaaggatta tggctttttc                                         30

<210> SEQ ID NO 196
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 196
gaaaaagcca taatccttgt cgtatactac                                         30

<210> SEQ ID NO 197
<211> LENGTH: 443
<212> TYPE: PRT
<213> ORGANISM: Cryptococcus neoformans

<400> SEQUENCE: 197
```

| | | | | | | | | | | | | | | | |
|---|---|---|---|---|---|---|---|---|---|---|---|---|---|---|---|
| Met | Pro | Pro | Ser | Arg | Ala | Ser | Thr | Lys | Val | Ile | Val | Ile | Gly | Gly | Gly |
| 1 | | | | 5 | | | | | 10 | | | | | 15 | |
| Gly | Thr | Leu | Gly | Ser | Ser | Thr | Ala | Leu | His | Leu | Leu | Arg | Ala | Gly | Tyr |
| | | | 20 | | | | | 25 | | | | | 30 | | |
| Thr | Pro | Ser | Asn | Ile | Thr | Val | Leu | Asp | Thr | Tyr | Leu | Ile | Pro | Ser | Ala |
| | | 35 | | | | | 40 | | | | | 45 | | | |
| Gln | Ser | Ala | Gly | Asn | Asp | Leu | Asn | Lys | Ile | Met | Gly | Ile | Arg | Ile | Arg |
| 50 | | | | | 55 | | | | | 60 | | | | | |
| Asn | Pro | Val | Asp | Lys | Gln | Leu | Ser | Leu | Glu | Ala | Arg | Asp | Met | Trp | Arg |
| 65 | | | | | 70 | | | | | 75 | | | | | 80 |
| Asn | Asp | Glu | Val | Phe | Lys | Pro | Tyr | Phe | His | Asn | Thr | Gly | Arg | Leu | Asp |
| | | | | 85 | | | | | 90 | | | | | 95 | |
| Cys | Ala | His | Thr | Pro | Glu | Ser | Ile | Ala | Ser | Leu | Arg | Lys | Ser | Tyr | Glu |
| | | | 100 | | | | | 105 | | | | | 110 | | |
| Ala | Ile | Leu | Lys | Ala | Gly | Ser | Gly | Leu | Glu | Lys | Thr | His | His | Trp | Leu |
| | | 115 | | | | | 120 | | | | | 125 | | | |
| Ser | Thr | Glu | Asp | Glu | Ile | Leu | Ala | Arg | Ala | Pro | Leu | Leu | Asp | Arg | Lys |
| | 130 | | | | | 135 | | | | | 140 | | | | |
| Gln | Ile | Lys | Gly | Trp | Lys | Ala | Ile | Tyr | Ser | Glu | Asp | Gly | Gly | Trp | Leu |
| 145 | | | | | 150 | | | | | 155 | | | | | 160 |
| Ala | Ala | Ala | Lys | Ala | Ile | Asn | Ser | Ile | Gly | Gln | Val | Leu | Lys | Glu | Lys |
| | | | | 165 | | | | | 170 | | | | | 175 | |
| Gly | Val | Thr | Phe | Gly | Phe | Gly | Ser | Ala | Gly | Ser | Phe | Lys | Lys | Pro | Leu |
| | | | 180 | | | | | 185 | | | | | 190 | | |
| Phe | Asp | Glu | Asp | Gly | Thr | Lys | Ala | Ile | Gly | Ile | Glu | Thr | Val | Asp | Gly |

```
                195                 200                 205
Thr Gln Tyr Phe Ala Asp Lys Val Val Leu Ala Ala Gly Ala Trp Ser
    210                 215                 220
Pro Thr Leu Val Asp Leu Glu Gly Gln Cys Cys Ser Lys Ala Trp Val
225                 230                 235                 240
Tyr Ala His Met Gln Leu Thr Pro Glu Glu Ala Ala Glu Tyr Lys Glu
                245                 250                 255
Cys Pro Val Val Tyr Asn Ser Glu Leu Gly Phe Phe Glu Pro Asn
            260                 265                 270
Glu Lys Gly Val Ile Lys Val Cys Asp Glu Phe Pro Gly Phe Thr Arg
            275                 280                 285
Phe Lys Gln His Gln Pro Tyr Gly Ala Ser Ser Thr Lys His Ile Ser
        290                 295                 300
Phe Pro Arg Ser His Ala Lys His Pro Thr Asp Thr Ile Pro Asp Glu
305                 310                 315                 320
Ser Asp Ala Ser Ile Arg Arg Ala Ile Ser Ala Phe Leu Pro Arg Phe
                325                 330                 335
Lys Glu Lys Glu Leu Phe Asn Arg Ala Leu Cys Trp Cys Thr Asp Thr
            340                 345                 350
Ala Asp Ala Asn Leu Leu Ile Cys Glu His Pro Lys Trp Lys Asn Phe
            355                 360                 365
Ile Leu Ala Thr Gly Asp Ser Gly His Ser Phe Lys Ile Leu Pro Asn
        370                 375                 380
Ile Gly Lys His Val Val Glu Leu Ile Glu Gly Thr Leu Ala Glu Asp
385                 390                 395                 400
Leu Ala Glu Ser Trp Arg Trp Arg Pro Gly Ser Gly Asp Pro Leu Ile
                405                 410                 415
Ser Arg Arg Ala Ala Pro Ala Arg Asp Leu Ala Asp Leu Pro Gly Trp
            420                 425                 430
Asn His Asp Glu Pro Ser Asp Asp Met Asp
            435                 440

<210> SEQ ID NO 198
<211> LENGTH: 1332
<212> TYPE: DNA
<213> ORGANISM: Cryptococcus neoformans

<400> SEQUENCE: 198
atgccgccgt cccgtgcttc aacgaaagtg attgtcattg gtggtggtgg tacgctgggc      60
tcctcaaccg ccctgcatct gctgcgcgcg ggctataccc cgagtaacat taccgtgctg     120
gatacgtacc tgatcccgag tgcccagtcc gcaggcaacg acctgaataa aattatgggt     180
attcgtatcc gcaatccggt ggataaacaa ctgagcctgg aagcccgtga tgtgtggcgc     240
aacgacgaag ttttcaaacc gtacttccat aacaccggtc gtctggactg cgctcacacg     300
ccggaatcaa ttgcgtcgct gcgtaaaagc tacgaagcca tcctgaaagc aggctcaggt     360
ctggaaaaaa cccatcactg ctgtcgacg  gaagatgaaa tcctggcacg tgcaccgctg     420
ctggaccgta acagattaa  aggttggaaa gcaatctata gtgaagatgg cggttggctg     480
gcggccgcaa aagctattaa ctccatcggc caagtcctga agaaaaaggg tgtgaccttc     540
ggctttggta gcgcaggctc tttttaaaaaa ccgctgttcg atgaagacgg cacgaaagcc     600
attggtatcg aaaccgttga tggtacgcag tattttgccg acaaagtggt tctggctgca     660
ggtgcatgga gcccgaccct ggttgatctg gaaggccagt gctgttctaa agcttgggtc     720
```

```
tacgcgcaca tgcaactgac gccggaagaa gccgcagaat ataaagaatg cccggtcgtg    780
tacaacagcg aactgggctt tttctttgaa ccgaacgaaa aaggtgtgat caaagtttgt    840
gatgaattcc cgggctttac ccgtttcaaa cagcatcaac cgtacggtgc tagctctacg    900
aaacacatta gctttccgcg ctctcatgcg aaacacccga ccgatacgat cccggatgaa    960
agtgacgcct ccattcgtcg cgctatctct gcgtttctgc cgcgtttcaa agaaaaagaa   1020
ctgtttaacc gcgcgctgtg ctggtgtacc gatacggctg acgcgaacct gctgatttgt   1080
gaacacccga aatggaaaaa tttatcctg gccaccggcg attcaggtca ttcgttcaaa    1140
attctgccga atatcggcaa acacgttgtc gaactgattg aaggtaccct ggccgaagat   1200
ctggcagaaa gctggcgttg gcgtccgggc agtggtgacc cgctgatctc ccgtcgcgct   1260
gcgccggcgc gcgacctggc ggacctgccg ggctggaacc acgacgaacc gagcgacgat   1320
gacatggact ga                                                       1332
```

<210> SEQ ID NO 199
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 199
gactgcgctc accgtccgga atcaattgcg                                      30

<210> SEQ ID NO 200
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 200
cgcaattgat tccggacggt gagcgcagtc                                      30

<210> SEQ ID NO 201
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 201
tcgctgcgta aacgctacga agccatc                                         27

<210> SEQ ID NO 202
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 202
gatggcttcg tagcgtttac gcagcga                                         27

<210> SEQ ID NO 203
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 203

-continued gaaagcaatc tataatgaag atggcggttg                                    30

<210> SEQ ID NO 204
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 204
caaccgccat cttcattata gattgctttc                                    30

<210> SEQ ID NO 205
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 205
ataaagaatg cccggccgtg tacaacagcg                                    30

<210> SEQ ID NO 206
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 206
cgctgttgta cacggccggg cattctttat                                    30

<210> SEQ ID NO 207
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 207
ataaagaatg cccgtgcgtg tacaacagcg                                    30

<210> SEQ ID NO 208
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 208
cgctgttgta cacgcacggg cattctttat                                    30

<210> SEQ ID NO 209
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 209
gtcgtgtaca acaaggaact gggcttttc                                     30

<210> SEQ ID NO 210
<211> LENGTH: 30
<212> TYPE: DNA

```
<213> ORGANISM: Artificial Sequence
<220> FEATURE:
<223> OTHER INFORMATION: Artificially Synthesized Primer Sequence

<400> SEQUENCE: 210
gaaaaagccc agttccttgt tgtacacgac                              30

<210> SEQ ID NO 211
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 211
gtcgtgtaca accgcgaact gggcttttc                               30

<210> SEQ ID NO 212
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 212
gaaaaagccc agttcgcggt tgtacacgac                              30

<210> SEQ ID NO 213
<211> LENGTH: 441
<212> TYPE: PRT
<213> ORGANISM: Neocosmospora vasinfecta

<400> SEQUENCE: 213
```

Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe His Asn Thr Gly Arg Leu Asp
            85                  90                  95

Cys Glu Ser Ser Ala Glu Gly Val Glu Gly Leu Arg Arg Glu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
            165                 170                 175

Gly Val Arg Phe Gly Phe Gly Gly Ala Gly Ser Phe Lys Arg Pro Leu
        180                 185                 190

Phe Ala Asp Asp Gly Thr Thr Cys Ile Gly Val Glu Thr Val Asp Gly
    195                 200                 205

```
Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Glu Pro Asn
                260                 265                 270

Glu Asn Gly Val Ile Lys Val Cys Asp Glu Phe Pro Gly Phe Thr Arg
            275                 280                 285

Phe Lys Gln His Gln Pro Tyr Gly Ala Pro Ala Pro Lys Pro Val Ser
290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
        355                 360                 365

Ile Leu Ala Thr Gly Asp Ser Gly His Ser Phe Lys Leu Leu Pro Ile
370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
        435                 440

<210> SEQ ID NO 214
<211> LENGTH: 1326
<212> TYPE: DNA
<213> ORGANISM: Neocosmospora vasinfecta

<400> SEQUENCE: 214
atgacgaccc cgcgtaaaga aacgacggtc ctgattattg gtggtggtgg cacgattggt      60
agctcgacgg ctctgcatct gctgcgtgcc ggctataccc cgtctaacat taccgtgctg     120
gatacgtacc cgatcccgag tgcccagtcc gcaggcaacg acctgaataa aattatgggt     180
atccgtctgc gcaataaagt tgatctgcaa ctgagcctgg aagcccgtga tatgtggcgc     240
aacgacgcac tgtttcgtcc gttttttccat aataccggcc gcctggactg cgaaagctct     300
gctgaaggcg tggaaggtct cgtcgcgaa tatcagaaac tggtggaagc aggcgttggt     360
ctggaagaaa cgcacgaatg gctggatagc gaagaagcta ttctggaaaa agcgccgctg     420
ctgcaacgtg aagaaattga aggttggaaa gccatctggt ctgaagaagg cggttggctg     480
gcggccgcaa aagctattaa cgcgatcggc gaagaactgc agcgtcaagg cgttcgcttc     540
ggttttggcg gtgccggtag ttttaaacgc ccgctgttcg cagatgacgg caccacgtgt     600
atcggtgtcg aaaccgtgga tgcacgcag tatcatgcgg acaaagtggt tctggctgca     660
ggtgcttggt caccggcgct ggtcgatctg gaagaacagt gctgttcgaa agcctgggtg     720
tacgcacaca tgcaactgac cccggaagaa gccgcagttt ataaaggctg cccggtcgtg     780
```

```
taccacggcg atgtcggctt tttctttgaa ccgaacgaaa atggcgttat taaagtctgt    840
gacgaattcc cgggttttac gcgtttcaaa cagcatcaac cgtatggtgc cccggcaccg    900
aaacctgtga gtgttccgcg ctcccatgcg aaacacccga ccgatacgta cccggacgct    960
tcagaagaat cgatcaaacg tgccgtgagt acctttctgc cgcgcttcaa agataaaccg   1020
ctgtttaacc gtgcactgtg ctggtgtacc gatacggccg actccgcact gctgatttgc   1080
gaacacccgc gctggaaaaa ttttatcctg cgcaccggcg atagcggtca ttctttcaaa   1140
ctgctgccga ttatcggcaa acacgttgtc gaactggttg aaggtcgtct ggcggatgac   1200
ctggctgaag cgtggcgttg gcgtccgggt cagggtgatg cacgtaaaag cattcgcgct   1260
gcgccggcga aagacctggc ggatatgccg ggctggaaac acgaccaaga ctcggaatca   1320
cgctga                                                              1326
```

<210> SEQ ID NO 215
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 215
cgcctggact gccaaagctc tgctgaag                                        28

<210> SEQ ID NO 216
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 216
cttcagcaga gctttggcag tccaggcg                                        28

<210> SEQ ID NO 217
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 217
cgcctggact gccatagctc tgctgaag                                        28

<210> SEQ ID NO 218
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 218
cttcagcaga gctatggcag tccaggcg                                        28

<210> SEQ ID NO 219
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 219
cgcctggact gcaaaagctc tgctgaag                                        28

```
<210> SEQ ID NO 220
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 220
cttcagcaga gcttttgcag tccaggcg                                          28

<210> SEQ ID NO 221
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 221
cgcctggact gccgtagctc tgctgaag                                          28

<210> SEQ ID NO 222
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 222
cttcagcaga gctacggcag tccaggcg                                          28

<210> SEQ ID NO 223
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 223
gaaagctctg ctgaacgcgt ggaaggtctg                                        30

<210> SEQ ID NO 224
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 224
cagaccttcc acgcgttcag cagagctttc                                        30

<210> SEQ ID NO 225
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 225
ggtctgcgtc gccgttatca gaaactg                                           27

<210> SEQ ID NO 226
<211> LENGTH: 27
<212> TYPE: DNA
<213> ORGANISM: Artificial Sequence
<220> FEATURE:
```

<223> OTHER INFORMATION: Artificially Synthesized Primer Sequence

<400> SEQUENCE: 226
cagtttctga taacggcgac gcagacc                                27

<210> SEQ ID NO 227
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 227
ggaaagccat ctggaatgaa gaaggcggt                              29

<210> SEQ ID NO 228
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 228
accgccttct tcattccaga tggctttcc                              29

<210> SEQ ID NO 229
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 229
ggaaagccat ctgggatgaa gaaggcggt                              29

<210> SEQ ID NO 230
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 230
accgccttct tcatcccaga tggctttcc                              29

<210> SEQ ID NO 231
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 231
taaaggctgc ccggccgtgt accacggc                               28

<210> SEQ ID NO 232
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 232
gccgtggtac acggccgggc agcccttta                              28

```
<210> SEQ ID NO 233
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 233
taaaggctgc ccgtgcgtgt accacggc                                              28

<210> SEQ ID NO 234
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 234
gccgtggtac acgcacgggc agccttta                                              28

<210> SEQ ID NO 235
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 235
gtcgtgtacc acaaggatgt cggcttttc                                             30

<210> SEQ ID NO 236
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 236
gaaaaagccg acatccttgt ggtacacgac                                            30

<210> SEQ ID NO 237
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 237
gtcgtgtacc accgcgatgt cggcttttc                                             30

<210> SEQ ID NO 238
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 238
gaaaaagccg acatcgcggt ggtacacgac                                            30

<210> SEQ ID NO 239
<211> LENGTH: 30
<212> TYPE: DNA
<213> ORGANISM: Artificial Sequence
<220> FEATURE:
<223> OTHER INFORMATION: Artificially Synthesized Primer Sequence
```

<400> SEQUENCE: 239
cgtctgcgca atggtcctga tctgcaactg						30

<210> SEQ ID NO 240
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 240
cagttgcaga tcaggaccat tgcgcagacg						30

<210> SEQ ID NO 241
<211> LENGTH: 437
<212> TYPE: PRT
<213> ORGANISM: Eupenicillium terrenum

<400> SEQUENCE: 241

```
Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe His Gln Val Gly Met Ile Asp
                85                  90                  95

Cys Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
```

```
                290                 295                 300
Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
                340                 345                 350

Ala Asp Ala Asn Leu Leu Ile Cys Glu His Pro Lys Trp Lys Asn Phe
                355                 360                 365

Ile Leu Ala Thr Gly Asp Ser Gly His Ser Phe Lys Leu Leu Pro Asn
370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
                420                 425                 430

His Asp Ala His Leu
        435

<210> SEQ ID NO 242
<211> LENGTH: 1314
<212> TYPE: DNA
<213> ORGANISM: Eupenicillium terrenum

<400> SEQUENCE: 242
atggctcatt cgcgtgcaag caccaaagtc gtcgtggttg ggggaggtgg tacgatcggg      60
tcttcgacgg ctctgcactt aatccgctct ggatataccc cctcaaatat caccgtgctt     120
gacgtataca agacccctcc attgcaatct gcaggacatg atttgaacaa gatcatgggc     180
attcgattgc gcaacgggcc tgacttgcag cttttcgctgg aatcactcga catgtggcaa     240
aacgatgagt tgttcaagcc attctttcac caagtgggca tgattgattg ttcgtcatcc     300
aaagagggta ttgaaaatct tcgacgaaaa taccagaccc tcctcgatgc gggcattggg     360
ctggagaaga cgaacgtttg gctggaatct gaagatgaga tcctcgccaa agcgccgaat     420
ttcacgcgtg aacaagtcaa ggggtggaaa ggcttatttt gcactgatgg aggctggctt     480
gctgcagcca aggctatcaa tgcgatcgga atttttcctcc aggacaaagg tgtcaagttt     540
ggctttggag atgctggaac atttcagcaa cctctgttcg ccgctgatgg aaaaaacttgc     600 atcggacttg aaactacaga cggaaccaag tactttgctg acaaggttgt cttggctgct     660
ggtgcgtgga gtcccacctt ggtggatcta aagatcagt gtgtttcaaa ggcctgggtt     720
ttcgctcata ttcaactcac acccaaagaa gcggacgcgt acaagaatgt gcctgtggtc     780
tatgatggtg aatatgggtt ctttttttgag cccgacgagt atggggtgat caaagtctgt     840
gacgagttcc ctggtttctc tcgcttcaaa ctgcatcaac gtacggggc tgcatctccc     900 aagatgatat ccgtaccgcg atcacacgcc aagcatccca cagataccta ccctgatgcc     960
tccgaagtca ccatacgcaa agcgatcgca aggttcctgc cagaatttaa agacaaggag    1020
ctcttcaacc gtaccatgtg ctggtgtaca gatacgcccg atgctaactt attgatttgc    1080
gaacacccga agtggaagaa tttcattctg gccactggag atagcggaca ttccttcaag    1140
ctgttgccaa acatcgggaa atacgttgtt gagcttttag agggatctct atcgcaggaa    1200
atggctggtg cctggagatg gagacccgga ggtgatgctc ttagatctag acgcggtgct    1260
```
ccggcaaagg atcttgctga gatgccggga tggaagcatg atgcacattt gtga         1314

<210> SEQ ID NO 243
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 243
catgattgat tgtgcgtcat ccaaagag                                      28

<210> SEQ ID NO 244
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 244
ctctttggat gacgcacaat caatcatg                                      28

<210> SEQ ID NO 245
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 245
ttcgacgtcg ctaccagacc ctcctc                                        26

<210> SEQ ID NO 246
<211> LENGTH: 25
<212> TYPE: DNA
<213> ORGANISM: Artificial Sequence
<220> FEATURE:
<223> OTHER INFORMATION: Artificially Synthesized Primer Sequence

<400> SEQUENCE: 246
tctggtagcg acgtcgaaga ttttc                                         25

<210> SEQ ID NO 247
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 247
tggaaaggcc tatttaacac tgatggagg                                     29

<210> SEQ ID NO 248
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 248
ccatcagtgt taaataggcc tttccaccc                                     29

<210> SEQ ID NO 249
<211> LENGTH: 29
<212> TYPE: DNA
<213> ORGANISM: Artificial Sequence

```
<220> FEATURE:
<223> OTHER INFORMATION: Artificially Synthesized Primer Sequence

<400> SEQUENCE: 249
caagaatgtg cctgcggtct atgatggtg                                        29

<210> SEQ ID NO 250
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 250
caccatcata gaccgcaggc acattcttg                                        29

<210> SEQ ID NO 251
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 251
caagaatgtg ccttgcgtct atgatggtg                                        29

<210> SEQ ID NO 252
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 252
caccatcata gacgcaaggc acattcttg                                        29

<210> SEQ ID NO 253
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 253
cctgtggtct atgataagga atatgggttc                                       30

<210> SEQ ID NO 254
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 254
gaacccatat tccttatcat agaccacagg                                       30

<210> SEQ ID NO 255
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 255
acacgcctga gcatatcgag gacctg                                           26
```

<210> SEQ ID NO 256
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 256
aggtcctcga tatgctcagg cgtgtg                                        26

<210> SEQ ID NO 257
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 257
ggtctggaga agactctggc ctggttggac                                    30

<210> SEQ ID NO 258
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 258
ggtctggaga agactttgc ctggttggac                                     30

<210> SEQ ID NO 259
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 259
ggtctggaga agacttatgc ctggttggac                                    30

<210> SEQ ID NO 260
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 260
agtcttctcc agacccgcac cggcatc                                       27

<210> SEQ ID NO 261
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 261
ttgtgtataa tcacgaattt ggcttc                                        26

<210> SEQ ID NO 262
<211> LENGTH: 26
<212> TYPE: DNA
<213> ORGANISM: Artificial Sequence
<220> FEATURE:
<223> OTHER INFORMATION: Artificially Synthesized Primer Sequence

```
<400> SEQUENCE: 262
aagccaaatt cgtgattata cacaac                                        26

<210> SEQ ID NO 263
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 263
ttgtgtataa tgatgaattt ggcttc                                        26

<210> SEQ ID NO 264
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 264
aagccaaatt catcattata cacaac                                        26

<210> SEQ ID NO 265
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 265
ttgtgtataa tgaagaattt ggcttc                                        26

<210> SEQ ID NO 266
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 266
aagccaaatt cttcattata cacaac                                        26

<210> SEQ ID NO 267
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 267
agacactgcg gacgatgctc tcttgatgtg                                    30

<210> SEQ ID NO 268
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 268
acatcaagag agcatcgtcc gcagtgtctg                                    30

<210> SEQ ID NO 269
```

```
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 269
agacactgcg gacgaagctc tcttgatgtg                                       30

<210> SEQ ID NO 270
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 270
acatcaagag agcttcgtcc gcagtgtctg                                       30

<210> SEQ ID NO 271
<211> LENGTH: 437
<212> TYPE: PRT
<213> ORGANISM: Coniochaeta sp.

<400> SEQUENCE: 271
```

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Arg Leu Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Ala His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
130                 135                 140

Gln Ile Gln Gly Trp Lys Ala Ile Trp Asn Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Cys Val Tyr Asn Gly Glu Phe Gly Phe Phe Phe Glu Pro Asp

```
                        260                 265                 270
Glu Phe Gly Val Ile Lys Val Cys Asp Glu Phe Pro Gly Phe Ser Arg
                275                 280                 285

Phe Lys Glu His Gln Pro Tyr Gly Ala Pro Ser Pro Lys Arg Ile Ser
        290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 272
<211> LENGTH: 437
<212> TYPE: PRT
<213> ORGANISM: Coniochaeta sp.

<400> SEQUENCE: 272

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Asp Ala Gly Ser Phe Lys Gln Pro Leu
            180                 185                 190
```

```
Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
        210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Glu Tyr Lys Gly
            245                 250                 255

Val Pro Val Val Tyr Asn Gly Glu Leu Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
        290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
            325                 330                 335

Gln Asp Lys Glu Leu Phe Asn Arg Ala Leu Cys Trp Cys Thr Asp Thr
        340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
            405                 410                 415

Arg Arg Ala Ala Pro Pro Lys Asp Leu Ala Asp Met Pro Gly Trp Lys
        420                 425                 430

His Asp Pro Lys Leu
            435

<210> SEQ ID NO 273
<211> LENGTH: 1314
<212> TYPE: DNA
<213> ORGANISM: Coniochaeta sp.

<400> SEQUENCE: 273
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atacgactgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggacct gaaaaagcag taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc      540 ggattcggcg acgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaacccc tggtggacct gaagatcaat gttgctcgaa ggcttgggtg     720
```

```
tatgctcata ttcagttgac gcctgaagag gccgctgagt ataagggtgt cccagttgtg    780
tataatggcg aacttggctt cttcttcgaa cctgatgagt ttggtgtaat aaaggtgtgc    840
gacgagttcc caggattctc gcgcttcaag aacatcaac  cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca aatggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314
```

<210> SEQ ID NO 274
<211> LENGTH: 437
<212> TYPE: PRT
<213> ORGANISM: Coniochaeta sp.

<400> SEQUENCE: 274

```
Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asn
            260                 265                 270
```

-continued

```
Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys His Ile Ser
        290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
370                 375                 380

Val Gly Lys His Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
            435

<210> SEQ ID NO 275
<211> LENGTH: 437
<212> TYPE: PRT
<213> ORGANISM: Eupenicillium terrenum

<400> SEQUENCE: 275

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
                20                  25                  30

Thr Pro Ser Asn Ile Thr Val Leu Asp Val Tyr Lys Thr Pro Ser Leu
            35                  40                  45

Gln Ser Ala Gly His Asp Leu Asn Lys Ile Met Gly Ile Arg Leu Arg
        50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Ala Gly Thr Phe Gln Gln Pro Leu
            180                 185                 190

Phe Ala Ala Asp Gly Lys Thr Cys Ile Gly Leu Glu Thr Thr Asp Gly
```

```
                  195                 200                 205
Thr Lys Tyr Phe Ala Asp Lys Val Val Leu Ala Ala Gly Ala Trp Ser
210                 215                 220
Pro Thr Leu Val Asp Leu Glu Asp Gln Cys Val Ser Lys Ala Trp Val
225                 230                 235                 240
Phe Ala His Ile Gln Leu Thr Pro Lys Glu Ala Asp Ala Tyr Lys Asn
                    245                 250                 255
Val Pro Val Val Tyr Asp Gly Glu Tyr Gly Phe Phe Glu Pro Asn
                260                 265                 270
Glu Tyr Gly Val Ile Lys Val Cys Asp Glu Phe Pro Gly Phe Ser Arg
                275                 280                 285
Phe Lys Leu His Gln Pro Tyr Gly Ala Ala Ser Pro Lys Met Ile Ser
290                 295                 300
Val Pro Arg Ser His Ala Lys His Pro Thr Asp Thr Tyr Pro Asp Ala
305                 310                 315                 320
Ser Glu Val Thr Ile Arg Lys Ala Ile Ala Arg Phe Leu Pro Glu Phe
                    325                 330                 335
Lys Asp Lys Glu Leu Phe Asn Arg Thr Met Cys Trp Cys Thr Asp Thr
                340                 345                 350
Ala Asp Ala Asn Leu Leu Ile Cys Glu His Pro Lys Trp Lys Asn Phe
                355                 360                 365
Ile Leu Ala Thr Gly Asp Ser Gly His Ser Phe Lys Leu Leu Pro Asn
370                 375                 380
Ile Gly Lys His Val Val Glu Leu Leu Glu Gly Ser Leu Ser Gln Glu
385                 390                 395                 400
Met Ala Gly Ala Trp Arg Trp Arg Pro Gly Gly Asp Ala Leu Arg Ser
                    405                 410                 415
Arg Arg Gly Ala Pro Ala Lys Asp Leu Ala Glu Met Pro Gly Trp Lys
                420                 425                 430
His Asp Ala His Leu
            435

<210> SEQ ID NO 276
<211> LENGTH: 440
<212> TYPE: PRT
<213> ORGANISM: Pyrenochaeta sp.

<400> SEQUENCE: 276

Met Ala Ala Ser Arg Ala Lys Thr Thr Val Ile Val Gly Gly Gly
1               5                   10                  15
Gly Thr Ile Gly Ser Ser Thr Ala Leu His Leu Leu Arg Ser Gly Tyr
                20                  25                  30
Thr Pro Ser Asn Ile Thr Val Leu Asp Thr Tyr Pro Ile Pro Ser Leu
            35                  40                  45
Gly Ser Ala Gly Asn Asp Leu Asn Lys Ile Met Gly Ile Arg Leu Arg
        50                  55                  60
Asn Lys Val Asp Leu Gln Leu Ser Leu Glu Ala Arg Glu Met Trp Arg
65                  70                  75                  80
Glu Asp Glu Leu Phe Arg Asp Phe Phe His Asn Thr Gly Arg Leu Asp
                85                  90                  95
Cys Ala His Gly Glu Lys Gly Ile Asn Asp Leu Arg Gln Ala Tyr Gln
                100                 105                 110
Thr Leu Leu Asp Ala Asn Ala Gly Leu Glu Glu Thr Asn Glu Trp Leu
            115                 120                 125
```

```
Asp Ser Glu Asp Glu Ile Leu Ala Arg Met Pro Leu Leu Ser Arg Glu
    130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Ala Gly Ser Phe Gln Gln Pro Leu
            180                 185                 190

Leu Ala Glu Gly Ile Cys Ile Gly Val Glu Thr Thr Asp Gly Thr Arg
            195                 200                 205

Tyr Tyr Ala Asp Lys Val Val Leu Ala Ala Gly Ala Trp Ser Pro Ala
    210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Lys His Gln Pro Phe Gly Ala Arg Ala Pro Lys Arg Ile Ser Val Pro
290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
        355                 360                 365

Ala Thr Gly Asp Ser Gly His Ser Phe Lys Leu Leu Pro Asn Ile Gly
    370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
            420                 425                 430

Asp Glu Ser Pro Arg Ala Lys Leu
        435                 440

<210> SEQ ID NO 277
<211> LENGTH: 452
<212> TYPE: PRT
<213> ORGANISM: Arthrinium sp.

<400> SEQUENCE: 277

Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Ala Thr Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60
```

```
Asn Pro Val Asp Lys Gln Leu Ser Leu Glu Ala Gln Asp Met Trp Cys
 65                  70                  75                  80

His Asp Glu Leu Phe Lys Pro Tyr Phe His Asn Thr Gly Arg Met Asp
                 85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
130                 135                 140

Gln Ile Lys Gly Trp Lys Ala Ile Phe Ser Gln Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Ala Gly Ala Phe Lys Lys Pro Leu
            180                 185                 190

Phe Ala Pro Asp Gly Ser Thr Cys Ile Gly Val Glu Thr Val Asp Gly
        195                 200                 205

Thr Lys Tyr Tyr Gly Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
        275                 280                 285

Phe Leu Glu Gln His Gln Ser Tyr Gly Ala Pro Ala Pro Thr Arg Val
    290                 295                 300

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
                325                 330                 335

Phe Gln Ser Lys Glu Leu Phe Asn Arg Ala Met Cys Trp Cys Thr Asp
            340                 345                 350

Thr Ala Asp Ala Ala Leu Leu Ile Cys Glu His Pro Arg Trp Arg Asn
        355                 360                 365

Phe Ile Leu Ala Thr Gly Asp Ser Gly His Ser Phe Lys Leu Leu Pro
    370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
                405                 410                 415

Lys Ser Arg Arg Ala Ala Pro Ala Lys Asp Leu Ala Asp Met Pro Gly
            420                 425                 430

Trp Asn His Asp Gly Asp Ser Gly Asn Ala Thr Ser Gly Thr Ser Ser
        435                 440                 445

Glu His Lys Leu
    450

<210> SEQ ID NO 278
<211> LENGTH: 440
```

<212> TYPE: PRT
<213> ORGANISM: Curvularia clavata

<400> SEQUENCE: 278

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
                100                 105                 110

Ala Leu Leu Asp Ala Asn Ala Gly Leu Glu Glu Thr Glu Trp Leu
            115                 120                 125

Asp Ser Glu Asp Glu Ile Leu Lys Lys Met Pro Leu Leu Asp Arg Glu
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
            195                 200                 205

Tyr Tyr Ala Asp Lys Val Val Leu Ala Ala Gly Ala Trp Ser Pro Val
    210                 215                 220

Leu Val Asp Leu Glu Asp Gln Cys Val Ser Lys Ala Trp Val Tyr Ala
225                 230                 235                 240

His Ile Gln Leu Thr Pro Glu Glu Ala Glu Tyr Lys Asn Val Pro
                245                 250                 255

Val Val Tyr Asn Gly Asp Val Gly Phe Phe Phe Glu Pro Asp Glu His
            260                 265                 270

Gly Val Ile Lys Val Cys Asp Glu Phe Pro Gly Phe Thr Arg Phe Lys
            275                 280                 285

Gln His Gln Pro Tyr Gly Ala Lys Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
    370                 375                 380

Lys His Val Val Glu Leu Leu Glu Gly Thr Leu Ala Glu Asp Leu Ala
385                 390                 395                 400
```

```
His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
            420                 425                 430

Asp Asp Val Val Lys Ser Lys Leu
        435                 440

<210> SEQ ID NO 279
<211> LENGTH: 477
<212> TYPE: PRT
<213> ORGANISM: Cryptococcus neoformans

<400> SEQUENCE: 279

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
```

-continued

```
                325                 330                 335
Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Ile Leu Pro Asn
            370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
                420                 425                 430

Asn His Asp Glu Pro Ser Asp Asp Met Asp Val Lys Asp Val Ala
                435                 440                 445

Val Ser Leu Ala Ser Val Lys Ile Gly Glu Asn Ile Gly Glu Lys Val
            450                 455                 460

Val Glu Asp Gly Ala Arg Val Gly Val Lys Val Leu Ala
465                 470                 475

<210> SEQ ID NO 280
<211> LENGTH: 437
<212> TYPE: PRT
<213> ORGANISM: Phaeosphaeria nodorum

<400> SEQUENCE: 280

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
            35                  40                  45

Gln Ser Ala Gly Asn Asp Leu Asn Lys Ile Met Gly Val Ser Leu Arg
        50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
            115                 120                 125

Glu Asp Glu Ile Leu Lys Arg Met Pro Leu Leu Ser Arg Asp Gln Ile
        130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
            195                 200                 205

Ala Asp Lys Val Val Leu Ala Ala Gly Ala Trp Ser Pro Thr Leu Val
        210                 215                 220
```

```
Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
            245                 250                 255

Tyr Asn Gly Asp Val Gly Phe Phe Glu Pro Asn Glu His Gly Val
        260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
                340                 345                 350

Leu Leu Ile Cys Glu His Pro Glu Trp Lys Asn Phe Val Leu Ala Thr
            355                 360                 365

Gly Asp Ser Gly His Ser Phe Lys Leu Leu Pro Asn Ile Gly Lys His
370                 375                 380

Val Val Glu Leu Leu Glu Gly Thr Leu Ala Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435

<210> SEQ ID NO 281
<211> LENGTH: 441
<212> TYPE: PRT
<213> ORGANISM: Ulocladium sp.

<400> SEQUENCE: 281

Met Ala Pro Asn Arg Ala Asn Ile Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Glu Asp Gly Gly Trp Leu
145                 150                 155                 160
```

```
Ala Ala Ala Lys Ala Ile Asn Ala Ile Gly Arg Phe Leu Arg Asp Gln
            165                 170                 175

Gly Val Lys Phe Gly Phe Gly Gly Ala Gly Ser Phe Lys Gln Pro Leu
        180                 185                 190

Leu Ala Glu Gly Val Cys Val Gly Val Glu Thr Val Asp Gly Thr Arg
            195                 200                 205

Tyr Tyr Ala Asp Lys Val Val Leu Ala Ala Gly Ala Trp Ser Pro Ala
        210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
                245                 250                 255

Val Val Tyr Asn Gly Asp Val Gly Phe Phe Phe Glu Pro Asp Glu Tyr
            260                 265                 270

Gly Val Ile Lys Val Cys Asp Glu Phe Pro Gly Phe Thr Arg Phe Lys
        275                 280                 285

Gln His Gln Pro Phe Gly Ala Ser Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
                325                 330                 335

Lys Glu Val Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
                405                 410                 415

Arg Ala Ala Arg Ala Lys Asp Leu Ala Asp Met Pro Gly Trp Asn His
            420                 425                 430

Asp Gly Glu Ala Pro Arg Ala Lys Leu
        435                 440

<210> SEQ ID NO 282
<211> LENGTH: 437
<212> TYPE: PRT
<213> ORGANISM: Penicillium janthinellum

<400> SEQUENCE: 282

Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
    50                  55                  60

Asn Gly Pro Asp Leu Gln Leu Ser Leu Glu Ala Leu Asp Met Trp Lys
65                  70                  75                  80

Asn Asp Pro Leu Phe Lys Pro Phe Phe His Asn Val Gly Met Leu Asp
```

```
                    85                  90                  95
Cys Ser Ser Ser Gln Glu Gly Ile Ala Ser Leu Arg Arg Lys His Gln
            100                 105                 110

Asp Leu Ile Asp Ala Asn Ile Gly Leu Glu Lys Thr Asn Ile Trp Leu
            115                 120                 125

Glu Ser Glu Asp Asp Ile Leu Ala Lys Ala Pro His Phe Thr Arg Glu
            130                 135                 140

Gln Ile Lys Gly Trp Lys Gly Leu Phe Cys Gly Asp Gly Gly Trp Leu
145                 150                 155                 160

Ala Ala Ala Lys Ala Ile Asn Ala Ile Gly Thr Phe Leu Lys Ser Gln
            165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
            195                 200                 205

Thr Lys Tyr Phe Ala Asp Lys Val Val Leu Ala Ala Gly Ala Trp Ser
            210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Phe Glu Pro Asn
            260                 265                 270

Glu His Gly Val Ile Lys Val Cys Asp Glu Phe Pro Gly Phe Ser Arg
            275                 280                 285

Phe Lys Leu His Gln Pro Tyr Gly Ala Thr Ser Pro Lys Leu Ile Ser
            290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Val Leu Pro Asn
            370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Gly Asp Ala Leu Lys Ser
            405                 410                 415

Lys Arg Ser Ala Pro Ala Lys Asp Leu Ala Glu Met Pro Gly Trp Lys
            420                 425                 430

His Asp Ala Lys Leu
            435
```

AMADORIASE HAVING ALTERED SUBSTRATE SPECIFICITY

CROSS-REFERENCE TO RELATED APPLICATIONS

This application is a national phase of PCT/JP2011/067898, filed Aug. 4, 2011, which was published as WO 2012/018094 on Feb. 9, 2012, and which claims the benefit of JP Appln No. 2010-176967, filed Aug. 6, 2010, and JP Appln No. 2010-213070, filed Sep. 24, 2010. The respective contents of these documents are incorporated here by reference in their entirety.

TECHNICAL FIELD

The present invention relates to amadoriases having altered substrate specificity, genes and recombinant DNAs thereof, and processes for producing amadoriases having altered substrate specificity.

BACKGROUND ART

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement. Examples of amino groups in proteins include α-amino group of amino terminus and side chain ε-amino groups of lysine residue in proteins. Examples of known glycated proteins generated in vivo include glycated hemoglobin resulting from glycation of hemoglobin and glycated albumin resulting from glycation of albumin in the blood.

Among such glycated proteins generated in vivo, glycated hemoglobin (HbA1c) has drawn attention as a glycemic control marker significant for diagnosis of diabetic patients and control of conditions in the field of clinical diagnosis of diabetes mellitus. The blood HbA1c level reflects the average blood glucose level for a given period of time in the past, and the measured value thereof serves as a significant indicator for diagnosis and control of diabetes conditions.

As a method for quickly and simply measuring HbA1c, an enzymatic method involving the use of amadoriases, wherein HbA1c is decomposed by a protease or other substance and α-fructosyl valyl histidine (hereafter, referred to as α-FVH) or α-fructosyl valine (hereafter, referred to as α-FV) released from the β-chain amino terminus is quantified, has been proposed (e.g., Patent Documents 1 to 6). According to a method in which α-FV is cleaved from HbA1c, in fact, the influence of contaminants is considered to be significant. At present, accordingly, a method in which α-FVH is measured is the major technique.

An amadoriase oxidizes iminodiacetic acid or a derivative thereof (also referred to as an "Amadori compound") in the presence of oxygen to catalyze a reaction to generate glyoxylic acid or α-ketoaldehyde, amino acid or peptide, and hydrogen peroxide.

Amadoriases have been found in bacteria, yeast, and fungi. Examples of known amadoriases having enzyme activity to α-FVH and/or α-FV, which are particularly useful for measurement of HbA1c, include amadoriases derived from the genera *Coniochaeta, Eupenicillium, Arthrinium, Curvularia, Leptosphaeria, Neocosmospora, Ophiobolus, Pleospora, Pyrenochaeta, Cryptococcus, Phaeosphaeria, Aspergillus, Ulocladium,* and *Penicillium* (e.g., Patent Documents 1 and 7 to 11; Non-Patent Documents: 1 to 4). In some of the aforementioned documents, an amadoriase is occasionally referred to as, for example, ketoamine oxidase, fructosyl amino acid oxidase, fructosyl peptide oxidase, or fructosyl amine oxidase.

In the measurement of HbA1c by an enzymatic method, amadoriases are required to have stringent substrate specificity. When HbA1c is measured by quantifying released α-FVH as described above, for example, use of amadoriases that are less likely to react with glycated amino acids or glycated peptides other than α-FVH that are present freely in specimens and/or released in the process of HbA1c treatment using proteases or the like is preferable. In particular, side chain ε-amino groups of lysine residues contained in the hemoglobin molecules are known to undergo glycation, and ε-fructosyl lysine in which an amino group at position ε derived from the glycated lysine residue has been glycated (hereafter, referred to as "ε-FK") is released by treatment with proteases or other substances (e.g., Non-Patent Document 5). Accordingly, amadoriases having high substrate specificity, which are less likely to react with ε-FK, potentially causing measurement errors, are strongly desired. However, the reactivity of most known amadoriases with ε-FK cannot be said to be sufficiently low.

As a general technique, a method of adding mutations to DNAs encoding enzymes, introducing substitutions into the amino acids of enzymes, and selecting enzymes with substrate specificity of interest in order to alter the substrate specificity of the enzymes is known. If an example of improving substrate specificity by amino acid substitution in enzymes with high homology is already known, further, improvement in the substrate specificity can be expected based on such information.

Regarding ketoamine oxidase derived from *Curvularia clavata* YH923 and ketoamine oxidase derived from *Neocosmospora vasinfecta* 474, in fact, modified ketoamine oxidase having altered substrate specificity for α-FVH resulting from substitution of several amino acids has been found (Patent Document 1). In the case of ketoamine oxidase derived from *Curvularia clavata* YH923, for example, substitution of isoleucine at position 58 with valine, arginine at position 62 with histidine, and phenylalanine at position 330 with leucine is found to reduce the ratio of activity (i.e., ε-FZK/α-FVH), which is determined by dividing enzyme activity to ε-fructosyl-(α-benzyloxycarbonyl lysine) (hereafter, referred to as "ε-FZK") by enzyme activity to α-FVH to result in a figure from 0.95 to 0.025.

However, ε-FZK used for evaluation of substrate specificity of a modified ketoamine oxidase in the aforementioned document is very different from ε-FK that is actually generated in the process of treatment of glycated hemoglobin with a protease in terms of molecular weight and structure. Accordingly, it is difficult to conclude that reactivity to ε-FK, which could actually cause measurement errors, is reduced based on reduced reactivity to ε-FZK. In addition, there is no description to the effect that reduction in reactivity to ε-FK was confirmed with the use of the modified ketoamine oxidase in the aforementioned document.

In addition, modified fructosyl amino acid oxidase resulting from introduction of amino acid substitution into fructosyl amino acid oxidase derived from *Aspergillus nidulans* A89 to alter substrate specificity, thereby additionally imparting reactivity to α-FVH thereto, has been reported (e.g., Patent Document 10). For example, substitution of serine at position 59 with glycine and lysine at position 65 with glycine or substitution of lysine at position 109 with glutamine of fructosyl amino acid oxidase derived from *Aspergillus nidulans* A89 is found to additionally impart enzyme activity to α-FVH. However, there is no description to the effect that such amino acid substitution would contribute to a reduction in reactivity to ε-FK.

There is another report regarding a modified fructosyl amino acid oxidase derived from fructosyl amino acid oxidase derived from *Aspergillus nidulans* A89, which is obtained by amino acid substitution to alter substrate specificity, thereby reducing the ratio of activity (i.e., ε-FK/α-FV), which is determined by dividing enzyme activity to ε-FK by enzyme activity to α-FV (e.g., Patent Document 12). However, there is no description regarding the activity of such modified enzyme on α-FVH.

Including naturally-occurring and modified amadoriases, specifically, only a very small number of reports have been made regarding amadoriases having low the ratio of activity (i.e., ε-FK/α-FVH and/or ε-FK/α-FV), which is determined by dividing enzyme activity to ε-FK by enzyme activity to α-FVH. Accordingly, there continues to be a need for amadoriases having sufficiently low reactivity to ε-FK enabling accurate measurement of HbA1c.

PRIOR ART DOCUMENTS

Patent Documents

[Patent Document 1] WO 2004/104203
[Patent Document 2] WO 2005/49857
[Patent Document 3] JP Patent Publication (Kokai) No. 2001-95598 A
[Patent Document 4] JP Patent Publication (Kokoku) No. H05-33997 B (1993)
[Patent Document 5] JP Patent Publication (Kokai) No. H11-127895 A (1999)
[Patent Document 6] WO 97/13872
[Patent Document 7] JP Patent Publication (Kokai) No. 2003-235585 A
[Patent Document 8] JP Patent Publication (Kokai) No. 2004-275013 A
[Patent Document 9] JP Patent Publication (Kokai) No. 2004-275063 A
[Patent Document 10] JP Patent Publication (Kokai) No. 2010-35469 A
[Patent Document 11] JP Patent Publication (Kokai) No. 2010-57474 A
[Patent Document 12] JP Patent Publication (Kokai) No. 2010-104278 A Non-Patent Documents

[Non-Patent Document 1] Biochem. Biophys. Res. Commun., 311, 104-11, 2003
[Non-Patent Document 2] Biotechnol. Bioeng., 106, 358-66, 2010
[Non-Patent Document 3] J. Biosci. Biocng., 102, 241-3, 2006
[Non-Patent Document 4] Eur. J. Biochem., 242, 499-505, 1996
[Non-Patent Document 5] J. Biol. Chem., 279, 27613-20, 2004

SUMMARY OF THE INVENTION

Object to Be Attained by the Invention

It is an object of the present invention to provide amadoriases having low reactivity to ε-FK and, more specifically, amadoriases having a low figure for ε-FK/α-FVH and/or ε-FK/α-FV.

Means for Attaining the Object

The present inventors have conducted concentrated studies in order to attain the above object. As a result, they discovered that such object could be attained by substituting a specific amino acid residue in the amadoriase derived from the genus *Coniochaeta* with another specific amino acid residue, thereby completing the present invention.

Specifically, the present invention is as follows.

(1) An amadoriase having the following properties (a) and/or (b):

(a) an amadoriase comprising an amino acid sequence derived from the amino acid sequence as shown in SEQ ID NO: 1 by deletion, insertion, addition, and/or substitution of one or several amino acids and exhibiting the lowered reactivity to ε-fructosyl lysine relative to the reactivity to α-fructosyl valyl histidine compared with an amadoriase comprising the amino acid sequence as shown in SEQ ID NO: 1; and (b) an amadoriase comprising an amino acid sequence derived from the amino acid sequence as shown in SEQ ID NO: 1 by deletion, insertion, addition, and/or substitution of one or several amino acids and exhibiting the lowered reactivity to ε-fructosyl lysine relative to the reactivity to α-fructosyl valine compared with an amadoriase comprising the amino acid sequence as shown in SEQ ID NO: 1.

(2) An amadoriase having one or more amino acid substitutions at positions corresponding to amino acids selected from the group consisting of the following (c) to (s) in the amino acid sequence as shown in SEQ ID NO: 1 and exhibiting the lowered reactivity to ε-fructosyl lysine relative to the reactivity to α-fructosyl valyl histidine and/or the lowered reactivity to ε-fructosyl lysine relative to the reactivity to α-fructosyl valine compared with an amadoriase prior to such substitution:

(c) glutamic acid at position 98;
(d) valine at position 259;
(e) serine at position 154;
(f) histidine at position 125;
(g) tyrosine at position 261;
(h) glycine at position 263;
(i) aspartic acid at position 106;
(j) glycine at position 103;
(k) alanine at position 355;
(l) aspartic acid at position 96;
(m) lysine at position 66 and/or valine at position 67;
(n) glutamine at position 70;
(o) threonine at position 100;
(p) glutamine at position 110;
(q) alanine at position 113;
(r) leucine at position 114; and
(s) aspartic acid at position 156.

(3) An amadoriase comprising an amino acid sequence derived from the amino acid sequence as shown in SEQ ID NO: 1 by substitution of amino acids at positions corresponding to one or more an amino acids selected from the group consisting of the following (t) to (aj) and exhibiting the lowered reactivity to ε-fructosyl lysine relative to the reactivity to α-fructosyl valyl histidine and/or the lowered reactivity to ε-fructosyl lysine relative to the reactivity to α-fructosyl valine compared with an amadoriase prior to such substitution:

(t) substitution of glutamic acid at position 98 with an amino acid other than proline; that is, glutamine, histidine, lysine, arginine, glycine, alanine, valine, isoleucme, leucine, methionine, cysteine, serine, threonine, asparagine, aspartic acid, phenylalanine, tyrosine, or tryptophan;

(u) substitution of valine at position 259 with alanine, cysteine, or serine;

(v) substitution of serine at position 154 with glycine, tyrosine, asparagine, glutamine, aspartic acid, glutamic acid, histidine, or cysteine;

(w) substitution of histidine at position 125 with alanine, leucine, phenylalanine, tyrosine, asparagine, glutamine, glutamic acid, lysine, or arginine;

(x) substitution of tyrosine at position 261 with alanine, leucine, phenylalanine, tryptophan, or lysine;

(y) substitution of glycine at position 263 with lysine, arginine, histidine, aspartic acid, or glutamic acid;

(z) substitution of aspartic acid at position 106 with an amino acid having a lower molecular weight than aspartic acid; that is, glycine, alanine, serine, valine, threonine, cysteine, leucine, isoleucine, or asparagine;

(aa) substitution of glycine at position 103 with lysine, arginine, or histidine;

(ab) substitution of alanine at position 355 with lysine, arginine, histidine, aspartic acid, or glutamic acid;

(ac) substitution of aspartic acid at position 96 with alanine, asparagine, histidine, or serine;

(ad) substitution of lysine at position 66 with glycine and/or valine at position 67 with proline;

(ae) substitution of glutamine at position 70 with proline;

(af) substitution of threonine at position 100 with arginine;

(ag) substitution of glutamine at position 110 with alanine, leucine, methionine, phenylalanine, tryptophan, asparagine, histidine, lysine, or arginine;

(ah) substitution of alanine at position 113 with glutamic acid or lysine;

(ai) substitution of leucine at position 114 with lysine or arginine; and (aj) substitution of aspartic acid at position 156 with asparagine.

(4) The amadoriase according to (3) comprising an amino acid sequence derived from the amino acid sequence as shown in SEQ ID NO: 1 by amino acid substitution selected from the group consisting of (ba) to (be) below:

(ba) substitution of an amino acid at a position corresponding to glutamic acid at position 98 with alanine, substitution of an amino acid at a position corresponding to serine at position 154 with asparagine, and substitution of an amino acid at a position corresponding to valine at position 259 with cysteine;

(bb) substitution of an amino acid at a position corresponding to glutamic acid at position 98 with arginine and substitution of an amino acid at a position corresponding to serine at position 154 with asparagine;

(bc) substitution of an amino acid at a position corresponding to glutamic acid at position 98 with glutamine and substitution of an amino acid at a position corresponding to valine at position 259 with alanine;

(bd) substitution of an amino acid at a position corresponding to glutamic acid at position 98 with arginine and substitution of an amino acid at a position corresponding to valine at position 259 with cysteine; and (be) substitution of an amino acid at a position corresponding to glutamine at position 110 with arginine, substitution of an amino acid at a position corresponding to serine at position 154 with asparagine, and substitution of an amino acid at a position corresponding to valine at position 259 with alanine.

(5) An amadoriase comprising an amino acid sequence derived from the amino acid sequence as shown in SEQ ID NO: 272 by substitution of an amino acid at a position corresponding to glutamic acid at position 98 with alanine, substitution of an amino acid at a position corresponding to serine at position 154 with asparagine, and substitution of an amino acid at a position corresponding to valine at position 259 with cysteine and exhibiting the lowered reactivity to ε-fructosyl lysine relative to the reactivity to α-fructosyl valyl histidine and the lowered reactivity to ε-fructosyl lysine relative to the reactivity to α-fructosyl valine compared with an amadoriase prior to such substitution.

(6) An amadoriase comprising an amino acid sequence derived from the amino acid sequence as shown in SEQ ID NO: 241 by amino acid substitution selected from the group consisting of (ca) to (cc) below and exhibiting the lowered reactivity to ε-fructosyl lysine relative to the reactivity to α-fructosyl valyl histidine and the lowered reactivity to ε-fructosyl lysine relative to the reactivity to α-fructosyl valine compared with an amadoriase prior to such substitution:

(ca) substitution of an amino acid at a position corresponding to serine at position 98 with alanine, substitution of an amino acid at a position corresponding to lysine at position 110 with arginine, and substitution of an amino acid at a position corresponding to valine at position 259 with cysteine;

(cb) substitution of an amino acid at a position corresponding to serine at position 98 with alanine and substitution of an amino acid at a position corresponding to valine at position 259 with cysteine; and (cc) substitution of an amino acid at a position corresponding to lysine at position 110 with arginine and substitution of an amino acid at a position corresponding to valine at position 259 with cysteine.

(7) An amadoriase gene encoding the amino acid sequence according to any of (1) to (6).

(8) A recombinant vector comprising the amadoriase gene according to (7).

(9) A host cell comprising the recombinant vector according to (8).

(10) A method for producing an amadoriase comprising the following steps:

(ak) culturing the host cell according to (6);

(al) expressing the amadoriase gene contained in the host cell; and (am) isolating the amadoriase from the culture product.

(11) A kit used for measuring glycated hemoglobin comprising the amadoriase according to any of (1) to (6).

This description includes part or all of the content as disclosed in the descriptions and/or drawings of Japanese Patent Application Nos. 2010-176967 and 2010-213070, which are priority documents of the present application.

Effects of the Invention

According to the present invention, an amadoriase having excellent substrate specificity that can be advantageously utilized as an enzyme for diagnosis of diabetes mellitus and a kit for measurement of a diabetes mellitus marker can be provided. More specifically, the present invention can provide an amadoriase having a low figure for ε-FK/α-FVH and/or ε-FK/α-FV.

BRIEF DESCRIPTION OF THE DRAWINGS

FIG. 1 shows amino acid sequence homology examples for various known amadoriases.

EMBODIMENTS FOR CARRYING OUT THE INVENTION

Figure 2:
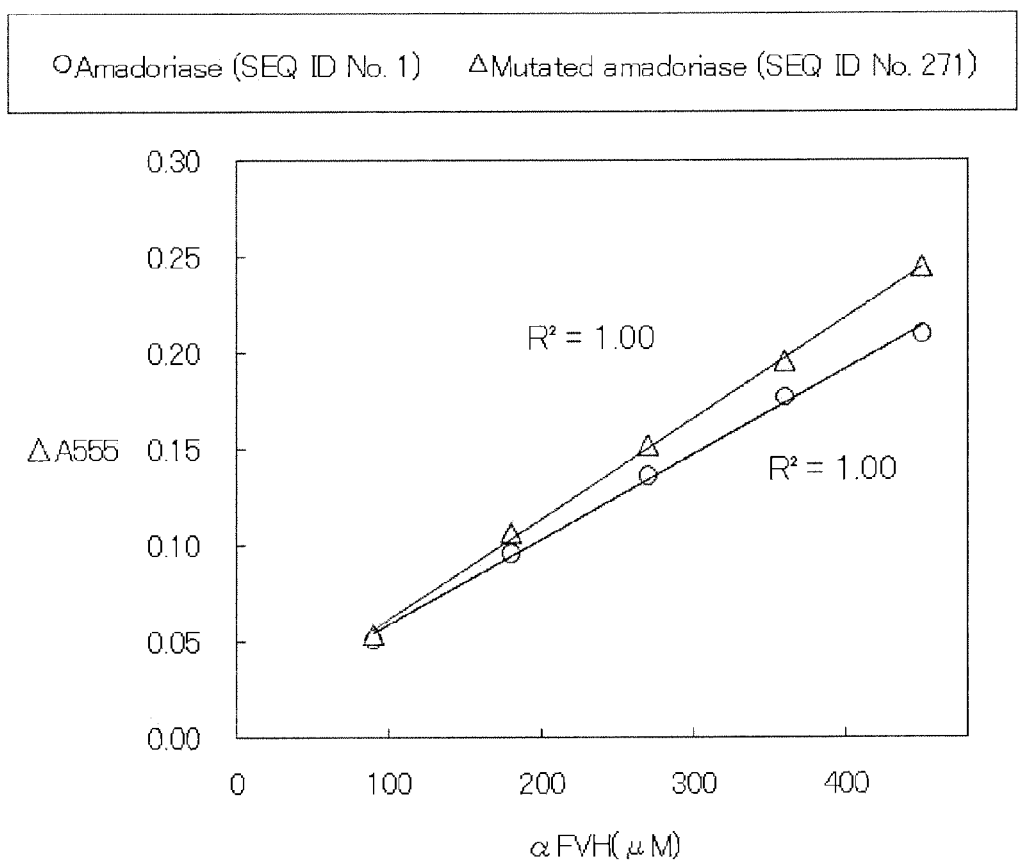
FIG. 2 is a chart showing the capacity of the amadoriase of the present invention for α-FVH quantification.

Hereafter, the present invention is described in detail.
(Amadoriase)

An amadoriase is also referred to as ketoamine oxidase, fructosyl amino acid oxidase, fructosyl peptide oxidase, or fructosyl amine oxidase, and it is an enzyme that oxidizes iminodiacetic acid or a derivative thereof (Amadori compound) in the presence of oxygen to catalyze a reaction to generate glyoxylic acid or α-ketoaldehyde, amino acid or peptide, and hydrogen peroxide. Amadoriases are widely distributed over the natural world and can be obtained by searching for enzymes derived from microorganisms, animals, or plants. In the microorganisms, amadoriases can be obtained from, for example, filamentous fungi, yeast, or bacteria.

The amadoriase according to the present invention is a modified amadoriase having altered substrate specificity, which is produced based on an amadoriase derived from the genus *Coniochaeta* having the amino acid sequence as shown in SEQ ID NO: 1. Examples of such mutants include an amadoriase having an amino acid sequence having sequence identity (for example, 75% or higher, preferably 80% or higher, more preferably 85% or higher, still more preferably 90% or higher, further preferably 95% or higher, still further preferably 97% or higher, and most preferably 99% or higher) with SEQ ID NO: 1 and an amadoriase having an amino acid sequence derived from the amino acid sequence as shown in SEQ ID NO: 1 by modification or mutation, deletion, substitution, addition, and/or insertion of one to several amino acids. As long as the conditions regarding substrate specificity and/or amino acid sequence described in the claims are satisfied, such mutant may be also produced based on an amadoriase derived from another organism species, such as the genus *Eupenicillium*, *Arthrinium*, *Curvularia*, *Leptosphaeria*, *Neocosmospora*, *Ophiobolus*, *Pleospora*, *Pyrenochaeta*, *Aspergillus*, *Cryptococcus*, *Phaeosphaeria*, *Ulocladium*, or *Penicillium*.

A mutant amadoriase having alter substrate specificity can be obtained through substitution of at least one amino acid residue in the amino acid sequence of the amadoriase.

Examples of amino acid substitution that alters substrate specificity include substitutions of amino acids at the positions corresponding to amino acids described below in the amino acid sequence as shown in SEQ ID NO: 1:

(1) substitution of glutamic acid at position 98 with, for example, an amino acid other than proline; that is, glutamine, histidine, lysine, arginine, glycine, alanine, valine, isoleucine, leucine, methionine, cysteine, serine, threonine, asparagine, aspartic acid, phenylalanine, tyrosine, or tryptophan;

(2) substitution of valine at position 259 with, for example, alanine, cysteine, or serine;

(3) substitution of serine at position 154 with, for example, glycine, tyrosine, asparagine, glutamine, aspartic acid, glutamic acid, histidine, or cysteine;

(4) substitution of histidine at position 125 with, for example, alanine, leucine, phenylalanine, tyrosine, asparagine, glutamine, glutamic acid, lysine, or arginine;

(5) substitution of tyrosine at position 261 with, for example, alanine, leucine, phenylalanine, tryptophan, or lysine;

(6) substitution of glycine at position 263 with, for example, lysine, arginine, histidine, aspartic acid, or glutamic acid;

(7) substitution of aspartic acid at position 106 with, for example, an amino acid having a lower molecular weight than aspartic acid; that is, glycine, alanine, serine, valine, threonine, cysteine, leucine, isoleucine, or asparagine;

(8) substitution of glycine at position 103 with, for example, lysine, arginine, or histidine;

(9) substitution of alanine at position 355 with, for example, lysine, arginine, histidine, aspartic acid, or glutamic acid;

(10) substitution of aspartic acid at position 96 with, for example, alanine, asparagine, histidine, or serine;

(11) substitution of lysine at position 66 with, for example, glycine;

(12) substitution of valine at position 67 with, for example, proline;

(13) substitution of glutamine at position 70 with, for example, proline;

(14) substitution of threonine at position 100 with, for example, arginine;

(15) substitution of glutamine at position 110 with, for example, alanine, leucine, methionine, phenylalanine, tryptophan, asparagine, histidine, lysine, or arginine;

(16) substitution of alanine at position 113 with, for example, glutamic acid or lysine;

(17) substitution of leucine at position 114 with, for example, lysine or arginine; and

(18) substitution of aspartic acid at position 156 with, for example, asparagine.

A mutant amadoriase having altered substrate specificity may comprise at least one of the above amino acid substitutions. For example, a mutant amadoriase comprises 1, 2, 3, 4, 5, 6, 7, 8, 9, 10, 11, 12, 13, 14, 15, 16, 17, or 18 amino acid substitutions described above.

Among them, mutants comprising substitution of amino acids corresponding to the amino acid positions described below are preferable. In the present invention, for example, a mutation of glutamine (Q) at position 110 being substituted with arginine (R) is designated as "Q110R."

A mutant comprising substitution of lysine at position 66 and valine at position 67, such as K66G and V67P;

a mutant comprising substitution of lysine at position 66, valine at position 67, and glutamic acid at position 98, such as K66G, V67P, and E98A;

a mutant comprising substitution of lysine at position 66, valine at position 67, and glutamine at position 110, such as K66O, V67P, and Q110R;

a mutant comprising substitution of glutamic acid at position 98 and glutamine at position 110, such as E98A and Q110R;

a mutant comprising substitution of glutamine at position 110 and histidine at position 125, such as Q110R and H125Q;

a mutant comprising substitution of glutamine at position 110 and serine at position 154, such as Q110R and S154G or S154N;

a mutant comprising substitution of glutamine at position 110 and alanine at position 355, such as Q110R and A355K;

a mutant comprising substitution of glutamic acid at position 98 and glycine at position 103, such as E98A and G103R;

a mutant comprising substitution of glutamic acid at position 98 and serine at position 154, such as E98A or E98R and S154N;

a mutant comprising substitution of glutamine at position 110 and serine at position 154, such as Q110R and S154C;

a mutant comprising substitution of glutamic acid at position 98, aspartic acid at position 106, and serine at position 154, such as E98A, D106S, and S154N;

a mutant comprising substitution of glutamic acid at position 98, glutamine at position 110, and serine at position 154, such as E98A, Q110R, and S154N;

a mutant comprising substitution of glutamine at position 110, histidine at position 125, and serine at position 154, such as Q110R, H125Q, and S154N;

a mutant comprising substitution of glutamic acid at position 98 and valine at position 259, such as E98Q and V259A, E98Q and V259C, E98H and V259A, E98H and V259C, E98R and V259C, and E98A and V259C;

a mutant comprising substitution of glutamic acid at position 98 and glycine at position 263, such as E98A and G263R;

a mutant comprising substitution of glutamine at position 110 and valine at position 259, such as Q110R and V259A;

a mutant comprising substitution of serine at position 154 and valine at position 259, such as S154D and V259A;

a mutant comprising substitution of glutamic acid at position 98, serine at position 154, and valine at position 259, such as E98A, S154N, and V259C; and a mutant comprising substitution of glutamine at position 110, scrine at position 154, and valine at position 259, such as Q110R, S154N, and V259A.

Among such combinations of amino acid substitutions, a combination according to any of the following (ba) to (be) is preferable:

(ba) substitution of an amino acid at a position corresponding to glutamic acid at position 98 with alanine, substitution of an amino acid at a position corresponding to serine at position 154 with asparagine, and substitution of an amino acid at a position corresponding to valine at position 259 with cysteine;

(bb) substitution of an amino acid at a position corresponding to glutamic acid at position 98 with arginine and substitution of an amino acid at a position corresponding to scrine at position 154 with asparagine;

(bc) substitution of an amino acid at a position corresponding to glutamic acid at position 98 with glutamine and substitution of an amino acid at a position corresponding to valine at position 259 with alanine;

(bd) substitution of an amino acid at a position corresponding to glutamic acid at position 98 with arginine and substitution of an amino acid at a position corresponding to valine at position 259 with cysteine; and (be) substitution of an amino acid at a position corresponding to glutamine at position 110 with arginine, substitution of an amino acid at a position corresponding to serine at position 154 with asparagine, and substitution of an amino acid at a position corresponding to valine at position 259 with alanine.

The mutant amadoriase having altered substrate specificity of the present invention encompasses a mutant amadoriase having altered substrate specificity, which comprises an amino acid sequence derived from the amino acid sequence as shown in SEQ ID NO: 1 by the above-described amino acid substitution that improves substrate specificity and, at positions other than the above, by deletion, insertion, addition, and/or substitution of one or several (e.g., 1 to 10, preferably 1 to 5, more preferably 1 to 3, and particularly preferably 1) amino acids, and has amadoriase activity. In addition, a mutant amadoriase having altered substrate specificity, which comprises amino acid substitution intended to alter substrate specificity and amino acid substitution intended to improve heat resistance and having sequence identity of 90% or higher, more preferably 95% or higher, still more preferably 97% or higher, and particularly preferably 99% or higher at the amino acid level with a region of the amino acid sequence as shown in SEQ ID NO: 1 excluding the substituted amino acids, and has amadoriase activity, is within the scope of the mutant amadoriase of the present invention.

In the above-described amino acid substitution, amino acid positions indicate positions in the amino acid sequence of an amadoriase derived from the genus *Coniochaeta* shown in SEQ ID NO: 1. In the case of the amino acid sequence of an amadoriase derived from other species, an amino acid at a position corresponding to the position in the amino acid sequence as shown in SEQ ID NO: 1 is substituted. The term "position corresponding to . . . " is defined below.

(Acquisition of Gene Encoding Amadoriase)

A gene cloning method that is generally used is typically used for obtaining genes in accordance with the present invention encoding these amadoriases (hereinafter, also referred to as merely "amadoriase gene"). For example, chromosomal DNA or mRNA can be extracted from a microorganism fungus body or various cells having an ability to produce an amadoriase by a conventional technique, such as a method described in "Current Protocols in Molecular Biology" (WILEY Interscience, 1989). In addition, cDNA can be synthesized using mRNA as a template. A chromosomal DNA or cDNA library can be made using the chromosomal DNA or cDNA obtained in such a manner.

Subsequently, DNA including the full length of a target amadoriase gene can be obtained by a method of synthesizing an appropriate probe DNA on the basis of the amino acid sequence of the aforementioned amadoriase and selecting an amadoriase gene from the chromosomal DNA or cDNA library using the probe DNA. Alternatively, an appropriate primer DNA may be produced on the basis of the aforementioned amino acid sequence, DNA including a target gene fragment encoding the amadoriase gene may be amplified by an appropriate polymerase chain reaction (PCR) technique, such as the 5' RACE or 3' RACE method, and resulting DNA fragments may then be linked.

A preferable example of a gene encoding an amadoriase thus obtained is an amadoriase gene derived from the genus *Coniochaeta* (Patent Document 7).

Such amadoriase genes are preferably linked to various vectors according to a conventional technique from the viewpoint of handleability. For example, DNA encoding an amadoriase gene can be extracted and purified from a recombinant plasmid pKK223-3-CFP (Patent Document 7) including DNA encoding an amadoriase gene derived from a strain of *Coniochaeta* sp. NISL9330 by using QIAGEN (manufactured by Qiagen K.K.).

(Vector)

Vectors that can be used in the present invention are not limited to the aforementioned plasmid vectors but include, for example, any other vectors known in the art, such as bacteriophage or cosmid vectors. Specifically, for example, pBluescriptII SK+ (manufactured by Stratagene Corporation) is preferable.

(Mutation of Amadoriase Gene)

Mutation of an amadoriase gene can be performed by any known method depending on an intended form of mutation. More specifically, a method of bringing a chemical mutagen into contact with and allowing to act on an amadoriase gene or recombinant DNA comprising such gene integrated therein; an ultraviolet irradiation method; a genetic engineering technique; or a method of making full use of a protein engineering technique; or other methods can be widely used.

Examples of chemical mutagens used in the aforementioned mutation include hydroxylamine, N-methyl-N'-nitro-N-nitrosoguanidine, nitrous acid, sulfurous acid, hydrazine, formic acid, and 5-bromouracil.

Various conditions for the contact/reactions may be adopted depending on the type of a drug to be used and are not particularly limited where a desired mutation can be actually induced in an amadoriase gene. Usually, the desired mutation can be induced by contact/reactions under a reaction temperature of 20° C. to 80° C. for 10 minutes or longer, preferably 10 to 180 minutes, preferably at the aforementioned drug concentration of 0.5 to 12 M. The ultraviolet irradiation may be also performed according to a conventional technique as described above (Gendai Kagaku, pp. 24-30, the June 1989).

As the method of making full use of the protein engineering technique, a technique known as site-specific mutagenesis can be generally used, and examples of which include a Kramer method (Nucleic Acids Res., 12, 9441, 1984; Methods Enzymol., 154, 350, 1987; Gene, 37, 73, 1985), an Eckstein method (Nucleic Acids Res., 13, 8749, 1985; Nucleic Acids Res., 13, 8765, 1985; Nucleic Acids Res, 14, 9679, 1986), and a Kunkel method (Proc. Natl. Acid. Sci. U.S.A., 82, 488, 1985; Methods Enzymol., 154, 367, 1987).

A technique known as a general PCR can be also used (Technique, 1, 11, 1989). In addition to the conventional genetic mutation technique, by an organic synthesis method or synthetic method of an enzyme, desired altered amadoriase genes can be also directly synthesized.

The DNA nucleotide sequences of amadoriase genes obtained by the aforementioned methods may be determined or verified by, for example, using a CEQ 2000 multi-capillary DNA analysis system (manufactured by Beckman Coulter, Inc.).

(Transformation/Transduction)

The amadoriase genes obtained as described above are integrated into a vector such as a bacteriophage vector, a cosmid vector, or a plasmid vector used in transformation of a procaryotic or eucaryotic cell by a conventional technique, and a host corresponding to each vector can be transformed or transduced by a conventional technique. For example, a microorganism belonging to the genus *Escherichia*, such as the obtained recombinant DNA, is used as the host to transform a strain of *E. coli* K-12, and preferably a strain of *E. coli* JM109 or *E. coli* DH5α (manufactured by Takara Bio Inc.), or such microorganism is transduced into such strain. Thus, transformed or transduced strains of interest can be obtained.

(Amino Acid Sequence Homology)

The amino acid sequence homology can be calculated by a program such as maximum matching or search homology of GENETYX-Mac (manufactured by Software Development Co., Ltd.) or a program such as maximum matching or multiple alignment of DNA SIS Pro (manufactured by Hitachi Software Engineering Co., Ltd.).

(Identification of Position Corresponding to Amino Acid)

The term "position corresponding to an amino acid" refers to a position in an amino acid sequence of an amadoriase derived from another organism species corresponding to an amino acid at a specific position in the amino acid sequence of an amadoriase derived from the genus *Coniochaeta* as shown in SEQ ID NO: 1.

Figure 1:
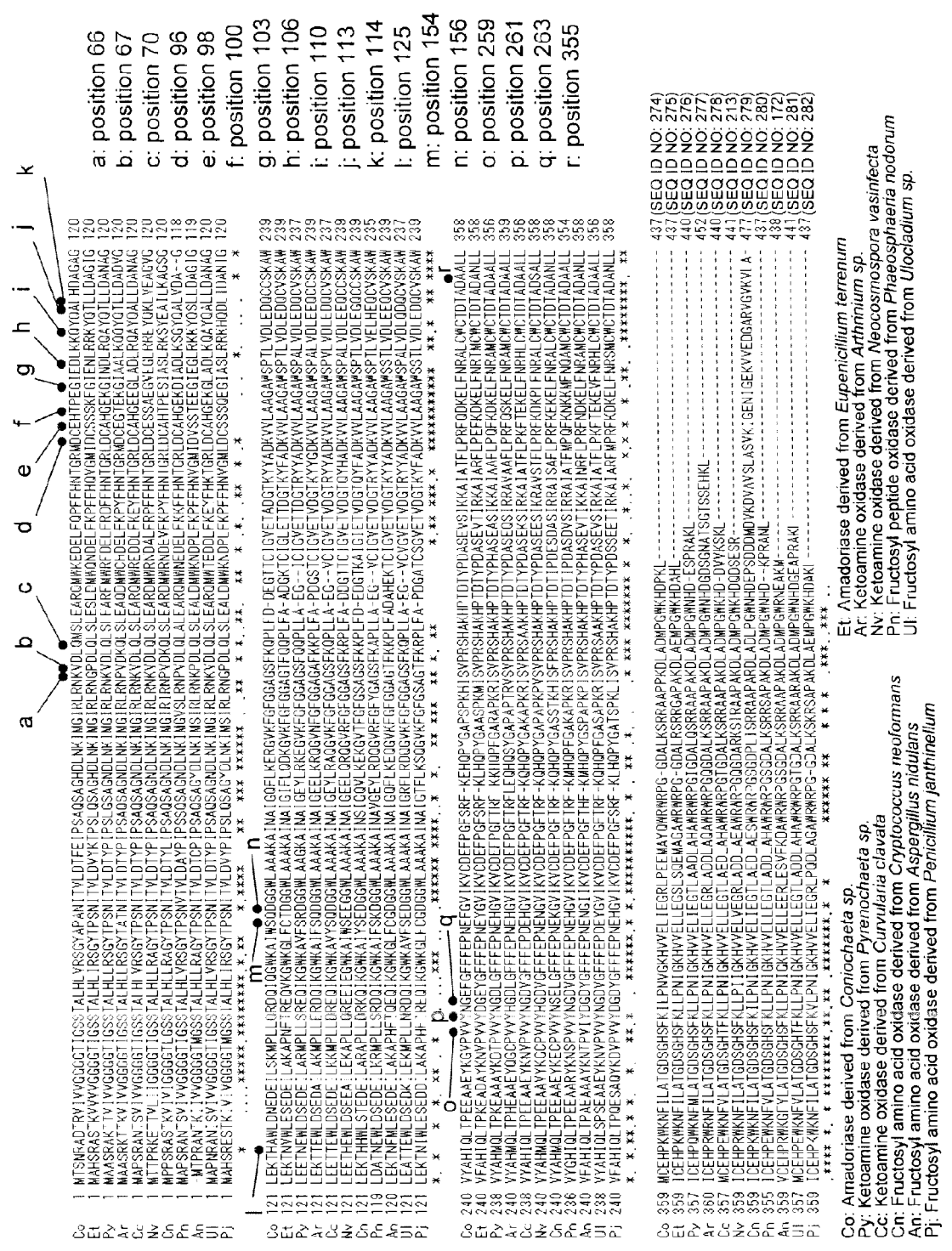

A method of identifying the "position corresponding to an amino acid" may be also performed by comparing amino acid sequences using a known algorithm such as a Lipman-Pearson method to assign maximum homology to conserved amino acid residues present in the amino acid sequence of each amadoriase. The positions of the homologous amino acid residues in each of the amadoriase sequences can be determined, regardless of insertion or deletion of amino acid residue(s) in the amino acid sequences by aligning the amino acid sequences of the amadoriases by such method. The homologous amino acid residues may be located at the same positions in three-dimensional structures, and the target amadoriases may be estimated to have similar effects in terms of specificity functions. FIG. 1 shows alignments of amadoriase sequences derived from various organism species. Based on FIG. 1, a position in an amino acid sequence of an amadoriase derived from another organism species corresponding to an amino acid at a specific position in the amino acid sequence of the amadoriase derived from the genus *Coniochaeta* can be identified. FIG. 1 shows amino acid sequences of an amadoriase derived from the genus *Coniochaeta*, an amadoriase derived from *Eupenicillium terrenum*, ketoamine oxidase derived from *Pyrenochaeta* sp., ketoamine oxidase derived from *Arthrinium* sp., ketoamine oxidase derived from *Curvularia clavata*, ketoamine oxidase derived from *Neocosmospora vasinfecta*, fructosyl amino acid oxidase derived from *Cryptococcus neoformans*, fructosyl peptide oxidase derived from *Phaeosphaeria nodorum*, fructosyl amino acid oxidase derived from *Aspergillus nidulans*, fructosyl amino acid oxidase derived from *Ulocladium* sp., and fructosyl amino acid oxidase derived from *Penicillium janthinellum*.

In the present invention, the term "a position corresponding to lysine at position 66 in the amino acid sequence as shown in SEQ ID NO: 1" refers to an amino acid corresponding to lysine at position 66 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to glycine at position 66 in the amadoriase derived from *Eupenicillium terrenum*, lysine at position 66 in the ketoamine oxidase derived from *Pyrenochaeta* sp., proline at position 66 in the ketoamine oxidase derived from *Arthrinium* sp., lysine at position 66 in the ketoamine oxidase derived from *Curvularia clavata*, lysine at position 66 in the ketoamine oxidase derived from *Neocosmospora vasinfecta*, proline at position 66 in the fructosyl amino acid oxidase derived from *Cryptococcus neoformans*, proline at position 66 in the fructosyl peptide oxidase derived from *Phaeosphaeria nodorum*, lysine at position 65 in the fructosyl amino acid oxidase derived from *Aspergillus nidulans*, lysine at position 66 in the fructosyl amino acid oxidase derived from *Ulocladium* sp., and glycine at position 66 in the fructosyl amino acid oxidase derived from *Penicillium janthinellum*.

In the present invention, the term "a position corresponding to valine at position 67 in the amino acid sequence as shown in SEQ ID NO: 1" refers to an amino acid corresponding to valine at position 67 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to proline at position 67 in the amadoriase derived from *Eupenicillium terrenum*, valine at position 67 in the ketoamine oxidase derived from *Pyrenochaeta* sp., valine at position 67 in the ketoamine oxidase derived from *Arthrinium* sp., valine at position 67 in the ketoamine oxidase derived from *Curvularia clavata*, valine at position 67 in the ketoamine oxidase derived from *Neocosmospora vasinfecta*, valine at position 67 in the fructosyl amino acid oxidase derived from *Cryptococcus neoformans*, valine at position 67 in the fructosyl peptide oxidase derived from *Phaeosphaeria nodorum*, proline at position 66 in the fructosyl amino acid oxidase derived from *Aspergillus nidulans*, valine at position 67 in the fructosyl amino acid oxidase derived from *Ulocladium* sp., and proline at position 67 in the fructosyl amino acid oxidase derived from *Penicillium janthinellum*.

In the present invention, the term "a position corresponding to glutamine at position 70 in the amino acid sequence as shown in SEQ ID NO: 1" refers to an amino acid corresponding to glutamine at position 70 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to glutamine at position 70 in the amadoriase derived from *Eupenicillium terrenum*, glutamine at position 70 in the ketoamine oxidase derived from *Pyrenochaeta* sp., glutamine at position 70 in the ketoamine oxidase derived from *Arthrinium* sp., glutamine at position 70 in the ketoamine oxidase derived from *Curvularia clavata*, glutamine at position 70 in the ketoamine oxidase derived from *Neocosmospora vasinfecta*, glutamine at position 70 in the fructosyl amino acid oxidase derived from *Cryptococcus neoformans*, glutamine at position 70 in the fructosyl peptide oxidase derived from *Phaeosphaeria nodorum*, glutamine at position 69 in the fructosyl amino acid oxidase derived from *Aspergillus nidulans*, glutamine at position 70 in the fructosyl amino acid oxidase derived from *Ulocladium* sp., and glutamine at position 70 in the fructosyl amino acid oxidase derived from *Penicillium janthinellum*.

In the present invention, the term "a position corresponding to aspartic acid at position 96 in the amino acid sequence as shown in SEQ ID NO: 1" refers to an amino acid corresponding to aspartic acid at position 96 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to aspartic acid at position 96 in the amadoriase derived from *Eupenicillium terrenum*, aspartic acid at position 96 in the ketoamine oxidase derived from *Pyrenochaeta* sp., aspartic acid at position 96 in the ketoamine oxidase derived from *Arthrinium* sp., aspartic acid at position 96 in the ketoamine oxidase derived from *Curvularia clavata*, aspartic acid at position 96 in the ketoamine oxidase derived from *Neocosmospora vasinfecta*, aspartic acid at position 96 in the fructosyl amino acid oxidase derived from *Cryptococcus neoformans*, aspartic acid at position 96 in the fructosyl peptide oxidase derived from *Phaeosphaeria nodorum*, aspartic acid at position 95 in the fructosyl amino acid oxidase derived from *Aspergillus nidulans*, aspartic acid at position 96 in the fructosyl amino acid oxidase derived from *Ulocladium* sp., and aspartic acid at position 96 in the fructosyl amino acid oxidase derived from *Penicillium janthinellum*.

In the present invention, the term "a position corresponding to glutamic acid at position 98 in the amino acid sequence as shown in SEQ ID NO: 1" refers to an amino acid corresponding to glutamic acid at position 98 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to serine at position 98 in the amadoriase derived from *Eupenicillium terrenum*, alanine at position 98 in the ketoamine oxidase derived from *Pyrenochaeta* sp., glutamic acid at position 98 in the ketoamine oxidase derived from *Arthrinium* sp., alanine at position 98 in the ketoamine oxidase derived from *Curvularia clavata*, glutamic acid at position 98 in the ketoamine oxidase derived from *Neocosmospora vasinfecta*, alanine at position 98 in the fructosyl amino acid oxidase derived from *Cryptococcus neoformans*, alanine at position 98 in the fructosyl peptide oxidase derived from *Phaeosphaeria nodorum*, serine at position 97 in the fructosyl amino acid oxidase derived from *Aspergillus nidulans*, alanine at position 98 in the fructosyl amino acid oxidase derived from *Ulocladium* sp., and serine at position 98 in the fructosyl amino acid oxidase derived from *Penicillium janthinellutn*.

In the present invention, the term "a position corresponding to threonine at position 100 in the amino acid sequence as shown in SEQ ID NO: 1" refers to an amino acid corresponding to threonine at position 100 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to serine at position 100 in the amadoriase derived from *Eupenicillium terrenum*, glycine at position 100 in the ketoamine oxidase derived from *Pyrenochaeta* sp., threonine at position 100 in the ketoamine oxidase derived from *Arthrinium* sp., glycine at position 100 in the ketoamine oxidase derived from *Curvularia clavata*, serine at position 100 in the ketoamine oxidase derived from *Neocosmospora vasinfecta*, threonine at position 100 in the fructosyl amino acid oxidase derived from *Cryptococcus neoformans*, glycine at position 100 in the fructosyl peptide oxidase derived from *Phaeosphaeria nodorum*, threonine at position 99 in the fructosyl amino acid oxidase derived from *Aspergillus nidulans*, glycine at position 100 in the fructosyl amino acid oxidase derived from *Ulocladium* sp., and serine at position 100 in the fructosyl amino acid oxidase derived from *Penicillium janthinellum*.

In the present invention, the term "a position corresponding to glycine at position 103 in the amino acid sequence as shown in SEQ ID NO: 1" refers to an amino acid corresponding to glycine at position 103 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to glycine at position 103 in the amadoriase derived from *Eupenicillium terrenum*, glycine at position 103 in the ketoamine oxidase derived from *Pyrenochaeta* sp., glycine at position 103 in the ketoamine oxidase derived from *Arthrinium* sp., glycine at position 103 in the ketoamine oxidase derived from *Curvularia clavata*, glycine at position 103 in the ketoamine oxidase derived from *Neocosmospora vasinfecta*, serine at position 103 in the fructosyl amino acid oxidase derived from *Cryptococcus neoformans*, aspartic acid at position 103 in the fructosyl peptide oxidase derived from *Phaeosphaeria nodorum*, glycine at position 102 in the fructosyl amino acid oxidase derived from *Aspergillus nidulans*, glycine at position 103 in the fructosyl amino acid oxidase derived from *Ulocladium* sp., and glycine at position 103 in the fructosyl amino acid oxidase derived from *Penicillium janthinellum*.

In the present invention, the term "a position corresponding to aspartic acid at position 106 in the amino acid sequence as shown in SEQ ID NO: 1" refers to an amino acid corresponding to aspartic acid at position 106 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to asparagine at position 106 in the amadoriase derived from *Eupenicillium terrenum*, aspartic acid at position 106 in the ketoamine oxidase derived from *Pyrenochaeta* sp., alanine at position 106 in the ketoamine oxidase derived from *Arthrinium* sp., aspartic acid at position 106 in the ketoamine oxidase derived from *Curvularia clavata*, glycine at position 106 in the ketoamine oxidase derived from *Neocosmospora vasinfecta*, serine at position 106 in the fructosyl amino acid oxidase derived from *Cryptococcus neoformans*, aspartic acid at position 106 in the fructosyl peptide oxidase derived from *Phaeosphaeria nodorum*, glycine at position 105 in the fructosyl amino acid oxidase derived from *Aspergillus nidulans*, aspartic acid at position 106 in the fructosyl amino acid oxidase derived from *Ulocladium* sp., and serine at position 106 in the fructosyl amino acid oxidase derived from *Penicillium janthinellum*.

In the present invention, the term "a position corresponding to glutamine at position 110 in the amino acid sequence as shown in SEQ ID NO: 1" refers to an amino acid corresponding to glutamine at position 110 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to lysine at position 110 in the amadoriase derived from *Eupenicillium terrenum*, alanine at position 110 in the ketoamine oxidase derived from *Pyrenochaeta* sp., glutamine at position 110 in the ketoamine oxidase derived from *Arthrinium* sp., alanine at position 110 in the ketoamine oxidase derived from *Curvularia clavata*, glutamic acid at position 110 in the ketoamine oxidase derived from *Neocosmospora vasinfecta*, serine at position 110 in the fructosyl amino acid oxidase derived from *Cryptococcus neoformans*, glycine at position 110 in the fructosyl peptide oxidase derived from *Phaeosphaeria nodorum*, lysine at position 109 in the fructosyl amino acid oxidase derived from *Aspergillus nidulans*, alanine at position 110 in the fructosyl amino acid oxidase derived from *Ulocladium* sp., and lysine at position 110 in the fructosyl amino acid oxidase derived from *Penicillium janthinellum*.

In the present invention, the term "a position corresponding to alanine at position 113 in the amino acid sequence as shown in SEQ ID NO: 1" refers to an amino acid corresponding to alanine at position 113 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to threonine at position 113 in the amadoriase derived from *Eupenicillium terrenum*, threonine at position 113 in the ketoamine oxidase derived from *Pyrenochaeta* sp., threonine at position 113 in the ketoamine oxidase derived from *Arthrinium* sp., alanine at position 113 in the ketoamine oxidase derived from *Curvularia clavata*, lysine at position 113 in the ketoamine oxidase derived from *Neocosmospora vasinfecta*, alanine at position 113 in the fructosyl amino acid oxidase derived from *Cryptococcus neoformans*, alanine at position 113 in the fructosyl peptide oxidase derived from *Phaeosphaeria nodorum*, serine at position 112 in the fructosyl amino acid oxidase derived from *Aspergillus nidulans*, alanine at position 113 in the fructosyl amino acid oxidase derived from *Ulocladiuin* sp., and aspartic acid at position 113 in the fructosyl amino acid oxidase derived from *Penicillium janthinellum*.

In the present invention, the term "a position corresponding to leucine at position 114 in the amino acid sequence as shown in SEQ ID NO: 1" refers to an amino acid corresponding to leucine at position 114 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to leucine at position 114 in the amadoriase derived from *Eupenicillium terrenum*, leucine at position 114 in the ketoamine oxidase derived from *Pyrenochaeta* sp., leucine at position 114 in the ketoamine oxidase derived from *Arthrinium* sp., leucine at position 114 in the ketoamine oxidase derived from *Curvularia clavata*, leucine at position 114 in the ketoamine oxidase derived from *Neocosmospora vasinfecta*, isoleucine at position 114 in the fructosyl amino acid oxidase derived from *Cryptococcus neoformans*, leucine at position 114 in the fructosyl peptide oxidase derived from *Phaeosphaeria nodorum*, leucine at position 113 in the fructosyl amino acid oxidase derived from *Aspergillus nidulans*, leucine at position 114 in the fructosyl amino acid oxidase derived from *Ulocladium* sp., and leucine at position 114 in the fructosyl amino acid oxidase derived from *Penicillium janthinellum*.

The term "a position corresponding to histidine at position 125 in the amino acid sequence as shown in SEQ ID NO: 1" refers to an amino acid corresponding to histidine at position 125 in the amino acid sequence as shown in SEQ ID NO: 1, when the identified amino acid sequence of amadoriase is compared with the amino acid sequence of the amadoriase derived from the genus *Coniochaeta* as shown in SEQ ID NO: 1. It can also be identified by aligning the amino acid sequences by the aforementioned method.

Specifically, the amino acid corresponds to asparagine at position 125 in the amadoriase derived from *Eupenicillium terrenum*, asparagine at position 125 in the ketoamine oxidase derived from *Pyrenochaeta* sp., threonine at position 125 in the ketoamine oxidase derived from *Arthrinium* sp., threonine at position 125 in the ketoamine oxidase derived from *Curvularia clavata*, histidine at position 125 in the ketoamine oxidase derived from *Neocosmospora vasinfecta*, histidine at position 125 in the fructosyl amino acid oxidase derived from *Cryptococcus neoformans*, asparagine at position 123 in the fructosyl peptide oxidase derived from *Phaeosphaeria* nodorum, asparagine at position 124 in the fructosyl amino acid oxidase derived from *Aspergillus nidulans*, threonine at position 125 in the fructosyl amino acid oxidase derived from *Ulocladium* sp., and asparagine at position 125 in the fructosyl amino acid oxidase derived from *Penicillium janthinellum*.

Further, the term "a position corresponding to serine at position 154 in the amino acid sequence as shown in SEQ ID NO: 1" refers to an amino acid corresponding to serine at position 154 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. It can also be identified by aligning the amino acid sequences by the aforementioned method.

Specifically, the amino acid corresponds to cysteine at position 154 in the amadoriase derived from *Eupenicillium terrenum*, serine at position 154 in the ketoamine oxidase derived from *Pyrenochaeta* sp., serine at position 154 in the ketoamine oxidase derived from *Arthrinium* sp., serine at position 154 in the ketoamine oxidase derived from *Curvularia clavata*, serine at position 154 in the ketoamine oxidase derived from *Neocosmospora vasinfecta*, serine at position 154 in the fructosyl amino acid oxidase derived from *Cryptococcus neoformans*, serine at position 152 in the fructosyl peptide oxidase derived from *Phaeosphaeria nodorum*, cysteine at position 153 in the fructosyl amino acid oxidase derived from *Aspergillus nidulans*, serine at position 154 in the fructosyl amino acid oxidase derived from *Ulocladium* sp., and cysteine at position 154 in the fructosyl amino acid oxidase derived from *Penicillium janthinellum*.

In the present invention, further, the term "a position corresponding to aspartic acid at position 156 in the amino acid sequence as shown in SEQ ID NO: 1" refers to an amino acid corresponding to aspartic acid at position 156 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to aspartic acid at position 156 in the amadoriase derived from *Eupenicillium terrenum*, aspartic acid at position 156 in the ketoamine oxidase derived from *Pyrenochaeta* sp., aspartic acid at position 156 in the ketoamine oxidase derived from *Arthrinium* sp., aspartic acid at position 156 in the ketoamine oxidase derived from *Curvularia clavata*, glutamic acid at position 156 in the ketoamine oxidase derived from *Neocosmospora vasinfecta*, aspartic acid at position 156 in the fructosyl amino acid oxidase derived from *Cryptococcus neoformans*, aspartic acid at position 154 in the fructosyl peptide oxidase derived from *Phaeosphaeria nodorum*, aspartic acid at position 155 in the fructosyl amino acid oxidase derived from *Aspergillus nidulans*, aspartic acid at position 156 in the fructosyl amino acid oxidase derived from *Ulocladium* sp., and aspartic acid at position 156 in the fructosyl amino acid oxidase derived from *Penicillium janthinellum*.

Further, the "a position corresponding to valine at position 259 in the amino acid sequence as shown in SEQ ID NO: 1" refers to an amino acid corresponding to valine at position 259 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. It can also be identified by aligning the amino acid sequences by the aforementioned method.

Specifically, the amino acid corresponds to valine at position 259 in the amadoriase derived from *Eupenicillium terrenum*, valine at position 257 in the ketoamine oxidase derived from *Pyrenochaeta* sp., valine at position 259 in the ketoamine oxidase derived from *Arthrinium* sp., valine at position 257 in the ketoamine oxidase derived from *Curvularia clavata*, valine at position 259 in the ketoamine oxidase derived from *Neocosmospora vasinfecta*, valine at position 259 in the fructosyl amino acid oxidase derived from *Cryptococcus neoformans*, valine at position 255 in the fructosyl peptide oxidase derived from *Phaeosphaeria nodorum*, valine at position 259 in the fructosyl amino acid oxidase derived from *Aspergillus nidulans*, valine at position 257 in the fructosyl amino acid oxidase derived from *Ulocladium* sp., and valine at position 259 in the fructosyl amino acid oxidase derived from *Penicillium janthinellum*.

Further, the term "a position corresponding to tyrosine at position 261 in the amino acid sequence as shown in SEQ ID NO: 1" refers to an amino acid corresponding to tyrosine at position 261 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. It can also be identified by aligning the amino acid sequences by the aforementioned method.

Specifically, the amino acid corresponds to tyrosine at position 261 in the amadoriase derived from *Eupenicillium terrenum*, tyrosine at position 259 in the ketoamine oxidase derived from *Pyrenochaeta* sp., tyrosine at position 261 in the ketoamine oxidase derived from *Arthrinium* sp., tyrosine at position 259 in the ketoamine oxidase derived from *Curvularia clavata*, tyrosine at position 261 in the ketoamine oxidase derived from *Neocosmospora vasinfecta*, tyrosine at position 261 in the fructosyl amino acid oxidase derived from *Cryptococcus neoformans*, tyrosine at position 257 in the fructosyl peptide oxidase derived from *Phaeosphaeria nodorum*, tyrosine at position 261 in the fructosyl amino acid oxidase derived from *Aspergillus nidulans*, tyrosine at position 259 in the fructosyl peptide oxidase derived from *Ulocladium* sp., and tyrosine at position 261 in the fructosyl amino acid oxidase derived from *Penicillium janthinellum*.

In the present invention, the term "a position corresponding to glycine at position 263 in the amino acid sequence as shown in SEQ ID NO: 1" refers to an amino acid corresponding to glycine at position 263 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. Thus, the amino acid sequences can be aligned and identified by the aforementioned method of identifying "an amino acid at a position corresponding to an amino acid".

Specifically, the amino acid corresponds to glycine at position 263 in the amadoriase derived from *Eupenicillium terrenum*, glycine at position 261 in the ketoamine oxidase derived from *Pyrenochaeta* sp., glycine at position 263 in the ketoamine oxidase derived from *Arthriniurn* sp., glycine at position 261 in the ketoamine oxidase derived from *Curvularia clavata*, glycine at position 263 in the ketoamine oxidase derived from *Neocosmospora vasinfecta*, serine at position 263 in the fructosyl amino acid oxidase derived from *Cryptococcus neoformans*, glycine at position 259 in the fructosyl peptide oxidase derived from *Phaeosphaeria nodorum*, glycine at position 263 in the fructosyl amino acid oxidase derived from *Aspergillus nidulans*, glycine at position 261 in the fructosyl amino acid oxidase derived from *Ulocladium* sp., and glycine at position 263 in the fructosyl amino acid oxidase derived from *Penicillium janthinellum*.

Further, the term "a position corresponding to alanine at position 355 in the amino acid sequence as shown in SEQ ID NO: 1" refers to an amino acid corresponding to alanine at position 355 in the amadoriase sequence as shown in SEQ ID NO: 1, when the identified amino acid sequence of amadoriase is compared with the amino acid sequence of the amadoriase derived from the genus *Coniochaeta* as shown in SEQ ID NO: 1. It can also be identified by aligning the amino acid sequences by the aforementioned method.

Specifically, the amino acid corresponds to alanine at position 355 in the amadoriase derived from *Eupenicillium terrenum*, alanine at position 353 in the ketoamine oxidase derived from *Pyrenochaeta* sp., alanine at position 356 in the ketoamine oxidase derived from *Arthrinium* sp., alanine at position 353 in the ketoamine oxidase derived from *Curvularia clavata*, serine at position 355 in the ketoamine oxidase derived from *Neocosmospora vasinfecta*, alanine at position 355 in the fructosyl amino acid oxidase derived from *Cryptococcus neoformans*, alanine at position 351 in the fructosyl peptide oxidase derived from *Phaeosphaeria nodorum*, alanine at position 355 in the fructosyl amino acid oxidase derived from *Aspergillus nidulans*, alanine at position 353 in the fructosyl amino acid oxidase derived from *Ulocladium* sp., and alanine at position 355 in the fructosyl amino acid oxidase derived from *Penicillium janthinellum*.

(Production of the Amadoriase of the Present Invention)

In order to produce an amadoriase having improved substrate specificity with the use of the strain having an ability to produce such amadoriase obtained as described above, the strain may be cultured by a general solid culture method, although liquid culture is more preferable wherever possible.

Examples of media that can be used to culture the aforementioned strains include media prepared by adding one or more of inorganic salts, such as sodium chloride, monopotassium phosphate, dipotassium phosphate, magnesium sulfate, magnesium chloride, ferric chloride, ferric sulfate, and manganese sulfate, to one or more nitrogen sources, such as a yeast extract, tryptone, peptone, a meat extract, a corn steep liquor, and a leaching solution of soybean or wheat bran, and further adding saccharine materials, vitamins, and the like thereto, according to need.

It is appropriate to adjust the initial pH of the media to 7 to 9.

In addition, culture is preferably performed at 20° C. to 42° C., and more preferably at about 37° C. for 4 to 24 hours, and further preferably at about 37° C. for 4 to 8 hours, by, for example, aeration spinner submerged culture, shake culture, or stationary culture.

Following the completion of culture, amadoriases may be collected from the culture products with enzyme collecting means that are generally employed. For example, a strain may be subjected to ultrasonic disintegration treatment or grinding treatment by a usual method, the enzyme may be extracted using a lytic enzyme such as lysozyme, or bacteriolysis may be effected on shaking or still standing in the presence of toluene to exhaust the enzyme from the fungus body to the outside. The solution is filtrated or centrifuged to remove a solid content, according to need, nucleic acid is removed with the aid of streptomycin sulfate, protamine sulfate, or manganese sulfate, ammonium sulfate, alcohol, or acetone is added to the solution so as to fractionate the solution, and sediments are then collected to obtain the crude enzymes of the amadoriases.

The purified amadoriase enzyme preparation can be obtained from: the crude enzyme of the aforementioned amadoriase by a method appropriately selected from gel filtration methods using Sephadex, Superdex, or Ultrogel; adsorption-elution methods using ion exchangers; electrophoretic methods using polyacrylamide gels, etc.; adsorption-elution methods using hydroxyapatite; sedimentation methods such as sucrose density-gradient centrifugation; affinity chromatographic methods; and fractionation methods using a molecular sieve membrane, a hollow-fiber membrane, etc., or by a combination thereof. Thus, an amadoriase having improved substrate specificity as desired can be obtained.

(Lowered Reactivity of the Amadoriase of the Present Invention to ε-FK)

The amadoriase of the present invention obtained by the means described above have improved substrate specificity as a result of mutation in the amino acid sequence caused by genetic modification or other means. Specifically, the ratio of "reactivity to ε-FK"/"reactivity to α-FVH" or the ratio of "reactivity to ε-FK"/"reactivity to α-FV" is lowered compared with that before modification. Alternatively, both the ratio of "reactivity to ε-FK"/"reactivity to α-FVH" and the ratio of "reactivity to ε-FK"/"reactivity to α-FV" are lowered compared with those before modification.

When glycated hemoglobin levels are measured, high reactivity to ε-FK may cause measurement errors. Accordingly, a lower reactivity to ε-FK is preferable. Specifically, the value represented by ε-FK/α-FVH, which indicates the ratio of reactivity of the amadoriase of the present invention to ε-FK relative to the reactivity thereof to α-FVH is preferably reduced by at least 10%, preferably at least 20%, more preferably at least 30%, and more preferably at least 40% compared with that before modification.

Also, the value represented by ε-FK/α-FV, which indicates the ratio of reactivity of the amadoriase of the present invention to ε-FK relative to the reactivity thereof to α-FV, is preferably reduced by at least 10%, more preferably at least 20%, further preferably at least 30%, and still further preferably at least 40% compared with that before modification.

The ratio of the reactivity to ε-FK relative to the reactivity to α-FVH or the ratio of the reactivity to ε-FK relative to the reactivity to α-FV can be measured under arbitrary conditions via known techniques of amadoriase measurement, and the measurement results can then be compared with the values before modification. For example, the activity value measured with the addition of 5 mM ε-FK at pH 7.0 may be divided by the activity value measured with the addition of 5 mM α-FVH, the ratio of the reactivity to ε-FK relative to the reactivity to α-FVH may be determined based thereon, and the obtained value may then be compared with that before modification. Also, the activity value measured with the addition of 5 mM ε-FK at pH 7.0 may be divided by the activity value measured with the addition of 5 mM α-FV, the ratio of the reactivity to ε-FK relative to the reactivity to α-FV may be determined based thereon, and the obtained value may then be compared with that before modification.

An example of the amadoriase of the present invention having improved substrate specificity compared with that before modification is an amadoriase produced by a strain of *E. coli* JM109 (pKK223-3-CFP-T7-Y261W). In the case of such amadoriases having improved substrate specificity as described above, a degree of ε-FK measured as a noise is satisfactorily reduced. Since α-FVH, which is a glycated amino acid released from the β-chain amino terminus in HbA1c, or α-FV, which is a glycated amino acid released from the β-chain amino terminus in HbA1c, can be selectively measured, accurate measurement can be carried out, and such amadoriase of the present invention is very useful at an industrial level.

(Method of Measuring Activity of Amadoriase)

The activity of an amadoriase can be measured by various methods. An example of the method of measuring the activity of an amadoriase as used herein is described below.

Examples of major methods for measuring the enzyme activity of the amadoriase of the present invention include a method of measuring the amount of hydrogen peroxide generated by enzyme reactions and a method of measuring the amount of oxygen consumed in enzyme reactions. An example of the method of measuring the amount of hydrogen peroxide is described below.

For measurement of the activity of the amadoriase of the present invention, α-FVH, ε-FK, or α-FV is used as a substrate, unless otherwise specified. Regarding an enzyme titer, the amount of enzyme used to generate 1 μmol of hydrogen peroxide per minute is defined as 1 U, when measurement is carried out using α-FVH, ε-FK, or α-FV as a substrate.

Glycated amino acids such as ε-FK and glycated peptides such as α-FVH synthesized and purified in accordance with, for example, the method of Sakaue et al. (see JP Patent Publication (Kokai) No. 2001-95598 A) can be used.

A: Preparation of Reagent (1) Reagent 1: Peroxidase-4-Amino Antipyrine Solution

Peroxidase (5.0 kU, manufactured by Kikkoman Corporation) and 100 mg of 4-amino antipyrine (manufactured by Tokyo Chemical Industry Co., Ltd.) are dissolved in a 0.1 M potassium phosphate buffer (pH 7.0, 7.5, or 8.0), and the volume of the solution is fixed at 1,000 ml.

(2) Reagent 2: TOOS Solution

TOOS (500 mg, manufactured by Dojindo Laboratories) is dissolved in ion-exchange water, and the volume of the solution is fixed at 100 ml.

(3) Reagent 3: Substrate Solution (150 mM; Final Concentration: 5 mM)

α-FVH (625 mg), 462 mg of ε-FK, or 419 mg of α-FV is dissolved in ion-exchange water, and the volume of the solution is fixed at 10 ml.

B. Method for Measuring Activity

Reagent 1 (2.7 ml), 100 μl of Reagent 2, and 100 μl of enzyme solution are mixed, and the mixture is preliminarily heated at 37° C. for 5 minutes. Subsequently, 100 μl of Reagent 3 is added, the resultant is thoroughly mixed, and the absorbance at 555 nm is then measured using a spectrophotometer (U-3010A, manufactured by Hitachi High-Technologies). The measurement values are based on the change in absorbance per minute from 1 to 2 minutes at 555 nm. A control solution was made by the same method except that 100 μl of ion-exchange water was added as a substitute for 100 μl of Reagent 3. A graph, in which relationships with the amounts of generated chromogen were examined, was prepared using a standard solution of hydrogen peroxide made beforehand as a substitute for Reagent 3 and ion-exchange water as a substitute for the enzyme solution. The number of micromoles of hydrogen peroxide generated per minute at 37° C. was calculated using the graph, and the unit of activity in the enzyme solution was based on the calculated value.

Hereafter, the present invention is described in greater detail with reference to the examples, although the technical scope of the present invention is not limited thereto.

EXAMPLE 1

(1) Preparation of DNA of Recombinant Plasmid pKK223-3-CFP-T7

A strain of E. coli JM109 (pKK223-3-CFP-T7) having the recombinant plasmid of an amadoriase gene (SEQ ID NO: 2) derived from the genus Coniochaeta (see WO 2007/125779) was inoculated into 3 ml of LB-amp media (1% (w/v) bactotrypton, 0.5% (w/v) peptone, 0.5% (w/v) NaCl, and 50 μg/ml ampicillin) and shake culture was conducted at 37° C. for 16 hours to obtain a culture product.

The culture product was centrifuged at 10,000×g for 1 minute to collect strains. A recombinant plasmid pKK223-3-CFP-T7 was extracted and purified therefrom using the GenElute Plasmid Mini-Prep Kit (manufactured by Sigma-Aldrich Corporation), and 2.5 μg of DNA of the recombinant plasmid pKK223-3-CFP-T7 was obtained.

(2) Site-Directed Modification Operation of DNA Recombinant Plasmid pKK223-3-CFP-T7

PCR was carried out under conditions described below using DNA of the recombinant plasmid pKK223-3-CFP-T7 as a template, synthetic oligonucleotides of SEQ ID NOs: 3 and 4, and KOD-Plus-(Toyobo Co., Ltd.).

Specifically, 5 μl of 10×KOD-Plus-buffer, 5 μl of a dNTPs mixture in which each dNTP is adjusted at 2 mM, 2 μl of a 25 mM MgSO$_4$ solution, 50 ng of DNA of pKK223-3-CFP-T7 as a template, 15 pmol each of the synthetic oligonucleotides, and 1 unit of KOD-Plus were mixed, and sterilized water was added thereto in order to bring the total amount of the solution to 50 μl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 30 times.

A part of the reaction solution was electrophoresed on 1.0% agarose gel, and specific amplification of about 6,000 bp DNA was confirmed. The DNAs obtained in such a manner were treated with a restriction enzyme DpnI (manufactured by New England Biolabs), the remaining template DNAs were cleaved, E. coli JM109 strains were transformed, and the transformants were then spread on LB-amp agar media. The grown colonies were inoculated into LB-amp media and shake-cultured therein, and plasmid DNAs were isolated in the same manner as in (1) above. A DNA nucleotide sequence encoding an amadoriase in the plasmid was determined using a CEQ 2000 multi-capillary DNA analysis system (manufactured by Beckman Coulter, Inc.). Thus, the recombinant plasmid encoding the modified amadoriase resulting from substitution of lysine at position 66 with glycine was obtained (pKK223-3-CFP-T7-K66G).

In order to substitute valine at position 67 in the amino acid sequence as shown in SEQ ID NO: 1 with proline, PCR was carried out using DNA of the recombinant plasmid pKK223-3-CFP-T7 as a template, the synthetic oligonucleotides of SEQ ID NOs: 5 and 6, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of valine at position 67 with proline was obtained (pKK223-3-CFP-T7-V67P).

In order to substitute lysine at position 66 and valine at position 67 in the amino acid sequence as shown in SEQ ID NO: 1 with glycine and proline, respectively, PCR was carried out using DNA of the recombinant plasmid pKK223-3-CFP-T7 as a template, the synthetic oligonucleotides of SEQ ID NOs: 7 and 8, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, the recombinant plasmids encoding the modified amadoriase resulting from substitution of lysine at position 66 and valine at position 67 with glycine and proline, respectively, were obtained (pKK223-3-CFP-T7-K66GV67P).

In order to substitute glutamine at position 70 in the amino acid sequence as shown in SEQ ID NO: 1 with proline, PCR was carried out using DNA of the recombinant plasmid pKK223-3-CFP-T7 as a template, the synthetic oligonucleotides of SEQ ID NOs: 9 and 10, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of glutamine at position 70 with proline was obtained (pKK223-3-CFP-T7-Q70P).

In order to substitute aspartic acid at position 96 in the amino acid sequence as shown in SEQ ID NO: 1 with alanine, PCR was carried out using DNA of the recombinant plasmid pKK223-3-CFP-T7 as a template, the synthetic oligonucleotides of SEQ ID NOs: 11 and 12, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of aspartic acid at position 96 with alanine was obtained (pKK223-3-CFP-T7-D96A).

In order to substitute glutamic acid at position 98 in the amino acid sequence as shown in SEQ ID NO: 1 with glutamine, PCR was carried out using DNA of the recombinant plasmid pKK223-3-CFP-T7 as a template, the synthetic oligonucleotides of SEQ ID NOs: 13 and 14, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of glutamic acid at position 98 with glutamine was obtained (pKK223-3-CFP-T7-E98Q).

In order to substitute threonine at position 100 in the amino acid sequence as shown in SEQ ID NO: 1 with arginine, PCR was carried out using DNA of the recombinant plasmid pKK223-3-CFP-T7 as a template, the synthetic oligonucleotides of SEQ ID NOs: 15 and 16, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of threonine at position 100 with arginine was obtained (pKK223-3-CFP-T7-T100R).

In order to substitute glycine at position 103 in the amino acid sequence as shown in SEQ ID NO: 1 with arginine, PCR was carried out using DNA of the recombinant plasmid pKK223-3-CFP-T7 as a template, the synthetic oligonucleotides of SEQ ID NOs: 17 and 18, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of glycine at position 103 with arginine was obtained (pKK223-3-CFP-T7-G103R).

In order to substitute aspartic acid at position 106 in the amino acid sequence as shown in SEQ ID NO: 1 with alanine, PCR was carried out using DNA of the recombinant plasmid pKK223-3-CFP-T7 as a template, the synthetic oligonucleotides of SEQ ID NOs: 19 and 20, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of aspartic acid at position 106 with alanine was obtained (pKK223-3-CFP-T7-D106A).

In order to substitute glutamine at position 110 in the amino acid sequence as shown in SEQ ID NO: 1 with alanine, PCR was carried out using DNA of the recombinant plasmid pKK223-3-CFP-T7 as a template, the synthetic oligonucleotides of SEQ ID NOs: 21 and 22, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of glutamine at position 110 with alanine was obtained (pKK223-3-CFP-T7-Q110A).

In order to substitute alanine at position 113 in the amino acid sequence as shown in SEQ ID NO: 1 with glutamic acid, PCR was carried out using DNA of the recombinant plasmid pKK223-3-CFP-T7 as a template, the synthetic oligonucleotides of SEQ ID NOs: 23 and 24, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of alanine at position 113 with glutamic acid was obtained (pKK223-3-CFP-T7-A113E).

In order to substitute leucine at position 114 in the amino acid sequence as shown in SEQ ID NO: 1 with lysine, PCR was carried out using DNA of the recombinant plasmid pKK223-3-CFP-T7 as a template, the synthetic oligonucleotides of SEQ ID NOs: 25 and 26, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriasc resulting from substitution of leucine at position 114 with lysine was obtained (pKK223-3-CFP-T7-L114K).

In order to substitute histidine at position 125 in the amino acid sequence as shown in SEQ ID NO: 1 with glutamic acid, PCR was carried out using DNA of the recombinant plasmid pKK223-3-CFP-T7 as a template, the synthetic oligonucleotides of SEQ ID NOs: 27 and 28, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of histidine at position 125 with glutamic acid was obtained (pKK223-3-CFP-T7-H125E).

In order to substitute serine at position 154 in the amino acid sequence as shown in SEQ ID NO: 1 with glutamic acid, PCR was carried out using DNA of the recombinant plasmid pKK223-3-CFP-T7 as a template, the synthetic oligonucleotides of SEQ ID NOs: 29 and 30, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of serine at position 154 with glutamic acid was obtained (pKK223-3-CFP-T7-S154E).

In order to substitute aspartic acid at position 156 in the amino acid sequence as shown in SEQ ID NO: 1 with asparagine, PCR was carried out using DNA of the recombinant plasmid pKK223-3-CFP-T7 as a template, the synthetic oligonucleotides of SEQ ID NOs: 31 and 32, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of aspartic acid at position 156 with asparagine was obtained (pKK223-3-CFP-T7-D156N).

In order to substitute valine at position 259 in the amino acid sequence as shown in SEQ ID NO: 1 with alanine, PCR was carried out using DNA of the recombinant plasmid pKK223-3-CFP-'f7 as a template, the synthetic oligonucleotides of SEQ ID NOs: 33 and 34, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of valine at position 259 with alanine was obtained (pKK223-3-CFP-T7-V259A).

In order to substitute tyrosine at position 261 in the amino acid sequence as shown in SEQ ID NO: 1 with alanine, PCR was carried out using DNA of the recombinant plasmid pKK223-3-CFP-T7 as a template, the synthetic oligonucleotides of SEQ ID NOs: 35 and 36, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of tyrosine at position 261 with alanine was obtained (pKK223-3-CFP-T7-Y261A).

In order to substitute glycine at position 263 in the amino acid sequence as shown in SEQ ID NO: 1 with arginine, PCR was carried out using DNA of the recombinant plasmid pKK223-3-CFP-T7 as a template, the synthetic oligonucleotides of SEQ ID NOs: 37 and 38, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of glycine at position 263 with arginine was obtained (pKK223-3-CFP-T7-G263R).

In order to substitute alanine at position 355 in the amino acid sequence as shown in SEQ ID NO: 1 with lysine, PCR was carried out using DNA of the recombinant plasmid pKK223-3-CFP-T7 as a template, the synthetic oligonucleotides of SEQ ID NOs: 39 and 40, and KOD-Plus-(Toyobo Co., Ltd.) under the conditions as described above, E. coli JM109 strains were transformed, and the nucleotide sequences of DNAs encoding amadoriases in plasmid DNAs of the grown colonies were determined. As a result, a recombinant plasmid encoding the modified amadoriase resulting from substitution of alanine at position 355 with lysine was obtained (pKK223-3-CFP-T7-A355K).

(3) Production of Various Types of Modified Amadoriases

The E. coli JM109 strains carrying the recombinant plasmids obtained by the above-described procedures were cultured in 3 ml of LB-amp media supplemented with 0.1 mM IPTG at 30° C. for 16 hours. The resulting cultured strains were washed with 20 mM HEPES-NaOH buffer (pH 7.0), the washed strains were suspended therein, the resulting suspension was ultrasonically disintegrated, and the resultant was centrifuged at 20,000×g for 10 minutes to prepare 0.6 ml of an enzyme solution used for confirmation of substrate specificity.

(4) Measurement of ε-FK/α-PVH and ε-FK/α-FV

The enzyme solutions thus obtained were subjected to measurement of enzyme activity to α-FVH, α-FV, and ε-FK by the method described in the "B: Method of activity measurement" above. For the purpose of comparison, the amadoriase before modification that had been produced from the E. coli JM109 strain (pKK223-3-CFP-T7) was subjected to measurement in the same manner. In this case, Reagent 1 (i.e., a peroxidase-4-amino antipyrinc solution) with a pH adjusted to 7.0 was used.

As a result, the ε-FK/α-FVH value of the amadoriase before modification that is produced by the E. coli JM109 strain (pKK223-3-CFP-T7) obtained based on the result of the measurement or enzyme activity was found to be 0.316 and the ε-FK/α-FV was found to be 0.093.

The ε-FK/α-FVH and the ε-FK/α-FV values of various amadoriases after modification resulting from site-directed mutagenesis and the ratio of ε-FK/α-FVH and the ratio of ε-FK/α-FV of the amadoriases after modification determined based on the ε-FK/α-FVH and ε-FK/α-FV values of amadoriases before modification designated as 100% are as shown in Table 1.

TABLE 1

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV(%) |
|---|---|---|---|---|---|---|
| pKK223-3-CFP-T7 | None | None | 0.316 | 100 | 0.093 | 100 |
| pKK223-3-CFP-T7-K66G | K66G | 3 and 4 | 0.255 | 81 | 0.080 | 86 |
| pKK223-3-CFP-T7-V67P | V67P | 5 and 6 | 0.239 | 76 | 0.072 | 77 |
| pKK223-3-CFP-T7-K66GV67P | K66G, V67P | 7 and 8 | 0.185 | 59 | 0.071 | 76 |
| pKK223-3-CFP-T7-Q70P | Q70P | 9 and 10 | 0.147 | 47 | 0.050 | 54 |
| pKK223-3-CFP-T7-D96A | D96A | 11 and 12 | 0.078 | 25 | 0.018 | 19 |
| pKK223-3-CFP-T7-E98Q | E98Q | 13 and 14 | 0.087 | 28 | 0.037 | 40 |
| pKK223-3-CFP-T7-T100R | T100R | 15 and 16 | 0.175 | 55 | 0.069 | 74 |

TABLE 1-continued

| Plasmid | Amino acid mutation | SEQ ID NO: of oligonucleotide | ε-FK/ α-FVH | Ratio of ε-FK/ α-FVH (%) | ε-FK/ α-FV | Ratio of ε-FK/ α-FV(%) |
|---|---|---|---|---|---|---|
| pKK223-3-CFP-T7-G103R | G103R | 17 and 18 | 0.110 | 35 | 0.050 | 54 |
| pKK223-3-CFP-T7-D106A | D106A | 19 and 20 | 0.164 | 52 | 0.066 | 71 |
| pKK223-3-CFP-T7-Q110A | Q110A | 21 and 22 | 0.248 | 78 | 0.081 | 87 |
| pKK223-3-CFP-T7-A113E | A113E | 23 and 24 | 0.279 | 88 | Not measured | |
| pKK223-3-CFP-T7-L114K | L114K | 25 and 26 | 0.095 | 30 | 0.036 | 39 |
| pKK223-3-CFP-T7-H125E | H125E | 27 and 28 | 0.216 | 68 | Not measured | |
| pKK223-3-CFP-T7-S154E | S154E | 29 and 30 | 0.162 | 51 | 0.047 | 51 |
| pKK223-CFP-T7-D156N | D156N | 31 and 32 | 0.171 | 54 | 0.074 | 80 |
| pKK223-3-CFP-T7-V259A | V259A | 33 and 34 | 0.080 | 25 | 0.029 | 31 |
| pKK223-3-CFP-T7-Y261A | Y261A | 35 and 36 | 0.145 | 46 | Not measured | |
| pKK223-3-CFP-T7-G263R | G263R | 37 and 38 | 0.123 | 39 | 0.055 | 59 |
| pKK223-3-CFP-T7-A355K | A355K | 39 and 40 | 0.177 | 56 | 0.048 | 52 |

As shown in Table 1, specifically, all of the modified amadoriases have improved substrate specificity.

EXAMPLE 2

(Test for Point Mutation of Aspartic Acid at Position 96)

Aspartic acid at position 96 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 2 (SEQ ID NOs: 41 to 46), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of aspartic acid at position 96 in the amino acid sequence as shown in SEQ ID NO: 1 with any of various types of amino acids were obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV and ε-FK by the method described in the "B: Method of activity measurement" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 2.

serine, asparagine, or histidine was lower than the value before modification (i.e., 0.316), and the ε-FK/α-FV value was lower than the value before modification (i.e., 0.093). Such amino acid substitution was found to be effective for production of an amadoriase having improved substrate specificity.

EXAMPLE 3

(Test for Point Mutation of Glutamic Acid at Position 98)

Glutamic acid at position 98 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 3 (SEQ ID NOs: 47 to 82), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of glutamic acid at position 98 in the amino acid sequence as shown in SEQ ID NO: 1 with any of various types of amino acids were obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activ-

TABLE 2

| Plasmid | Amino acid mutation | SEQ ID NO: of oligonucleotide | ε-FK/ α-FVH | Ratio of ε-FK/α-FVH (%) | ε-FK/ α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-D96A | D96A | 11 and 12 | 0.078 | 25 | 0.018 | 19 |
| pKK223-3-CFP-T7-D96S | D96S | 41 and 42 | 0.100 | 32 | 0.021 | 23 |
| pKK223-3-CFP-T7-D96N | D96N | 43 and 44 | 0.221 | 70 | 0.025 | 27 |
| pKK223-3-CFP-T7-D96H | D96H | 45 and 46 | 0.095 | 30 | 0.023 | 25 |

As shown in Table 2, the ε-FK/α-FVH value of the modified amadoriase comprising an amino acid sequence derived from the amino acid sequence as shown in SEQ ID NO: 1 by substitution of aspartic acid at position 96 with alanine, ity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 3.

TABLE 3

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-E98Q | E98Q | 13 and 14 | 0.087 | 28 | 0.037 | 40 |
| pKK223-3-CFP-T7-E98H | E98H | 47 and 48 | 0.107 | 34 | 0.041 | 44 |
| pKK223-3-CFP-T7-E98K | E98K | 49 and 50 | 0.051 | 16 | 0.021 | 23 |
| pKK223-3-CFP-T7-E98R | E98R | 51 and 52 | 0.039 | 12 | 0.015 | 16 |
| pKK223-3-CFP-T7-E98G | E98G | 53 and 54 | 0.120 | 38 | 0.044 | 47 |
| pKK223-3-CFP-T7-E98A | E98A | 55 and 56 | 0.122 | 39 | 0.048 | 52 |
| pKK223-3-CFP-T7-E98V | E98V | 57 and 58 | 0.113 | 36 | 0.046 | 49 |
| pKK223-3-CFP-T7-E98I | E98I | 59 and 60 | 0.121 | 38 | 0.042 | 45 |
| pKK223-3-CFP-T7-E98L | E98L | 61 and 62 | 0.064 | 20 | 0.023 | 25 |
| pKK223-3-CFP-T7-E98M | E98M | 63 and 64 | 0.083 | 26 | 0.034 | 37 |
| pKK223-3-CFP-T7-E98C | E98C | 65 and 66 | 0.111 | 35 | 0.043 | 46 |
| pKK223-3-CFP-T7-E98S | E98S | 67 and 68 | 0.122 | 39 | 0.046 | 49 |
| pKK223-3-CFP-T7-E98T | E98T | 69 and 70 | 0.118 | 37 | 0.047 | 51 |
| pKK223-3-CFP-T7-E98N | E98N | 71 and 72 | 0.105 | 33 | 0.039 | 42 |
| pKK223-3-CFP-T7-E98D | E98D | 73 and 74 | 0.207 | 66 | 0.077 | 83 |
| pKK223-3-CFP-T7-E98F | E98F | 75 and 76 | 0.080 | 25 | 0.039 | 42 |
| pKK223-3-CFP-T7-E98Y | E98Y | 77 and 78 | 0.104 | 33 | 0.045 | 48 |
| pKK223-3-CFP-T7-E98W | E98W | 79 and 80 | 0.082 | 26 | 0.035 | 38 |
| pKK223-3-CFP-T7-E98P | E98P | 81 and 82 | Unmeasurable | | Unmeasurable | |

As shown in Table 3, the ε-FK/α-FVH value of the modified amadoriase resulting from substitution of glutamic acid at position 98 in the amino acid sequence as shown in SEQ ID NO: 1 with another amino acid other than proline; that is, any of glutamine, histidine, lysine, arginine, glycine, alanine, valine, isoleucine, leucine, methionine, cysteine, serine, threonine, asparagine, aspartic acid, phenylalanine, tyrosine, or tryptophan, was lower than the value before modification (i.e., 0.316) and the ε-FK/α-FV value thereof was lower than the value before modification (i.e., 0.093). Such amino acid substitution was found to be effective for production of an amadoriase having improved substrate specificity. When glutamic acid at position 98 in the amino acid sequence as shown in SEQ ID NO: 1 was substituted with proline, enzyme expression was not observed.

sequence as shown in SEQ ID NO: 1 with any of various types of amino acids were obtained.

The *E. coli* JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 4.

TABLE 4

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-G103R | G103R | 17 and 18 | 0.110 | 35 | 0.050 | 54 |
| pKK223-3-CFP-T7-G103K | G103K | 83 and 84 | 0.134 | 42 | 0.055 | 59 |
| pKK223-3-CFP-T7-G103H | G103H | 255 and 256 | 0.181 | 57 | 0.070 | 75 |

EXAMPLE 4

(Test for Point Mutation of Glycine at Position 103)

Glycine at position 103 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 4 (SEQ ID NOs: 83, 84, 255, and 256), and KOD-Plus-(Toyobo Co., Ltd.), *E. coli* JM109 strains were transformed, and the nucleotide sequences of DNAs encoding amadoriases in plasmid DNAs of the grown colonies were determined. As a result, *E. coli* JM109 strains producing modified amadoriases resulting from substitution of glycine at position 103 in the amino acid As shown in Table 4, the ε-FK/α-FVH value of the modified amadoriase resulting from substitution of glycine at position 103 in the amino acid sequence as shown in SEQ ID NO: 1 with arginine, lysine, or histidine was lower than the value before modification (i.e., 0.316), and the ε-FK/α-FV value was lower than the value before modification (i.e., 0.093). Such amino acid substitution was found to be effective for production of an amadoriase having improved substrate specificity.

EXAMPLE 5

(Test for Point Mutation of Aspartic Acid at Position 106)

Aspartic acid at position 106 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 5 (SEQ ID NOs: 85 to 100), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of aspartic acid at position 106 in the amino acid sequence as shown in SEQ ID NO: 1 with any of various types of amino acids were obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 5.

TABLE 5

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-D106A | D106A | 19 and 20 | 0.164 | 52 | 0.066 | 71 |
| pKK223-3-CFP-T7-D106G | D106G | 85 and 86 | 0.163 | 52 | 0.065 | 70 |
| pKK223-3-CFP-T7-D106S | D106S | 87 and 88 | 0.173 | 55 | 0.071 | 76 |
| pKK223-3-CFP-T7-D106T | D106T | 89 and 90 | 0.171 | 54 | 0.073 | 78 |
| pKK223-3-CFP-T7-D106N | D106N | 91 and 92 | 0.152 | 48 | 0.068 | 73 |
| pKK223-3-CFP-T7-D106C | D106C | 93 and 94 | 0.180 | 57 | 0.070 | 75 |
| pKK223-3-CFP-T7-D106V | D106V | 95 and 96 | 0.182 | 58 | 0.079 | 85 |
| pKK223-3-CFP-T7-D106L | D106L | 97 and 98 | 0.158 | 50 | 0.074 | 80 |
| pKK223-3-CFP-T7-D106I | D106I | 99 and 100 | 0.163 | 52 | 0.072 | 77 |

As shown in Table 5, the ε-FK/α-FVH value of the modified amadoriase resulting from substitution of aspartic acid at position 106 in the amino acid sequence as shown in SEQ ID NO: 1 with an amino acid having a molecular weight smaller than that of aspartic acid; that is, glycine, alanine, serine, valine, threonine, cysteine, leucine, isoleucine, or asparagine, was lower than the value before modification (i.e., 0.316), and the ε-FK/α-FV value was lower than the value before modification (i.e., 0.093). Such amino acid substitution was found to be effective for production of an amadoriase having improved substrate specificity.

EXAMPLE 6

(Test for Point Mutation of Glutamine at Position 110)

Glutamine at position 110 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 6 (SEQ ID NOs: 101 to 118), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of glutamine at position 110 in the amino acid sequence as shown in SEQ ID NO: 1 with any of various types of amino acids were obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 6.

TABLE 6

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-Q110A | Q110A | 21 and 22 | 0.248 | 78 | 0.081 | 87 |
| pKK223-3-CFP-T7-Q110L | Q110L | 101 and 102 | 0.255 | 81 | 0.104 | 112 |
| pKK223-3-CFP-T7-Q110M | Q110M | 103 and 104 | 0.247 | 78 | 0.101 | 109 |
| pKK223-3-CFP-T7-Q110F | Q110F | 105 and 106 | 0.187 | 59 | 0.086 | 92 |
| pKK223-3-CFP-T7-Q110W | Q110W | 107 and 108 | 0.251 | 79 | 0.075 | 81 |
| pKK223-3-CFP-T7-Q110N | Q110N | 109 and 110 | 0.235 | 74 | 0.085 | 91 |
| pKK223-3-CFP-T7-Q110H | Q110H | 111 and 112 | 0.199 | 63 | 0.069 | 74 |
| pKK223-3-CFP-T7-Q110K | Q110K | 113 and 114 | 0.142 | 45 | 0.064 | 69 |
| pKK223-3-CFP-T7-Q110R | Q110R | 115 and 116 | 0.105 | 33 | 0.048 | 52 |
| pKK223-3-CFP-T7-Q110E | Q110E | 117 and 118 | 0.595 | 188 | 0.193 | 208 |

As shown in Table 6, the ε-FK/α-FVH value of the modified amadoriase resulting from substitution of glutamine at position 110 in the amino acid sequence as shown in SEQ ID NO: 1 with alanine, leucine, methionine, phenylalanine, tryptophan, asparagine, histidine, lysine, or arginine was lower than the value before modification (i.e., 0.316), and the ε-FK/α-FV value of the modified amadoriase resulting from substitution of glutamine at position 110 with alanine, phenylalanine, tryptophan, asparagine, histidine, lysine, or arginine was lower than the value before modification (i.e., 0.093). Such amino acid substitution was found to be effective for production of an amadoriase having improved substrate specificity. In contrast, the ε-FK/α-FVH value and the ε-FK/α-FV value of the modified amadoriase resulting from substitution of glutamine at position 110 in the amino acid sequence as shown in SEQ ID NO: 1 with glutamic acid were higher than the values before modification (i.e. 0.316 and 0.093).

EXAMPLE 7

(Test for Point Mutation of Alanine at Position 113)

Alanine at position 113 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 7 (SEQ ID NOs: 119 and 120), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of alanine at position 113 in the amino acid sequence as shown in SEQ ID NO: 1 with lysine was obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH and ε-FK by the method described in "B. Method of measuring activity" above, and ε-FK/α-FVH was determined. In this case, Reagent 1 (i.e., a peroxidase-4-amino antipyrine solution) with a pH adjusted to 7.0 was used. The results are shown in Table 7.

TABLE 7

| Plasmid | Amino acid mutation | SEQ ID NO: of oligonucleotide | ε-FK/α-FVH | Ratio of ε-FK/α-FVH (%) |
|---|---|---|---|---|
| pKK223-3-CFP-T7 | None | None | 0.316 | 100 |
| pKK223-3-CFP-T7-A113E | A113E | 23 and 24 | 0.279 | 88 |
| pKK223-3-CFP-T7-A113K | A113K | 119 and 120 | 0.279 | 88 |

As shown in Table 7, the ε-FK/α-FVH value of the modified amadoriase resulting from substitution of alanine at position 113 in the amino acid sequence as shown in SEQ ID NO: 1 with glutamic acid or lysine was lower than the value before modification (i.e., 0.316). Such amino acid substitution was found to be effective for production of an amadoriase having improved substrate specificity.

EXAMPLE 8

(Test for Point Mutation of Leucine at Position 114)

Leucine at position 114 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 8 (SEQ ID NOs: 121 to 124), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of leucine at position 114 in the amino acid sequence as shown in SEQ ID NO: 1 with any of various types of amino acids were obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 8.

TABLE 8

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-L114K | L114K | 25 and 26 | 0.095 | 30 | 0.036 | 39 |
| pKK223-3-CFP-T7-L114R | L114R | 121 and 122 | 0.132 | 42 | 0.049 | 53 |
| pKK223-3-CFP-T7-L114E | L114E | 123 and 124 | 0.332 | 105 | Not measured | |

As shown in Table 8, the ε-FK/α-FVH value of the modified amadoriase resulting from substitution of leucine at position 114 in the amino acid sequence as shown in SEQ ID NO: 1 with lysine or arginine was lower than the value before modification (i.e., 0.316), and the ε-FK/α-FV value was lower than the value before modification (i.e., 0.093). Such amino acid substitution was found to be effective for production of an amadoriase having improved substrate specificity. In contrast, the ε-FK/α-FVH value of the modified amadoriase resulting from substitution of leucine at position 114 in the amino acid sequence as shown in SEQ ID NO: 1 with glutamic acid was higher than the value before modification (i.e., 0.316).

EXAMPLE 9

(Test for Point Mutation of Histidine at Position 125)

Histidine at position 125 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 9 (SEQ Ill NOs: 125 to 134 and 257 to 260), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of histidine at position 125 in the amino acid sequence as shown in SEQ ID NO: 1 with any of various types of amino acids were obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-F/α-FV were determined. In this case, Reagent 1 (i.e., a peroxidase-4-amino antipyrine solution) with a pH adjusted to 7.0 was used. The results are shown in Table 9.

As shown in Table 9, the ε-FK/α-FVH value of the modified amadoriase resulting from substitution of histidine at position 125 in the amino acid sequence as shown in SEQ ID NO: 1 with glutamic acid, asparagine, lysine, alanine, glutamine, arginine, leucine, phenylalanine, or tyrosine was lower than the value before modification (i.e., 0.316), and the ε-FK/α-FV value of the modified amadoriase resulting from substitution of histidine at position 125 with asparagine, lysine, glutamine, arginine, leucine, phenylalanine, or tyrosine was lower than the value before modification (i.e., 0.093). Such amino acid substitution was found to be effective for production of an amadoriase having improved substrate specificity.

EXAMPLE 10

(Test for Point Mutation of Serine at Position 154)

Serine at position 154 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 10 (SEQ ID NOs: 135 to 150), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of serine at position 154 in the amino acid sequence as shown in SEQ ID NO: 1 with any of various types of amino acids were obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 10.

TABLE 9

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-H125E | H125E | 27 and 28 | 0.216 | 68 | Not measured | |
| pKK223-3-CFP-T7-H125N | H125N | 125 and 126 | 0.240 | 76 | 0.081 | 87 |
| pKK223-3-CFP-T7-H125K | H125K | 127 and 128 | 0.090 | 28 | 0.033 | 35 |
| pKK223-3-CFP-T7-H125A | H125A | 129 and 130 | 0.199 | 63 | 0.102 | 110 |
| pKK223-3-CFP-T7-H125Q | H125Q | 131 and 132 | 0.169 | 53 | 0.044 | 47 |
| pKK223-3-CFP-T7-H125R | H125R | 133 and 134 | 0.088 | 28 | 0.025 | 27 |
| pKK223-3-CFP-T7-H125L | H125L | 257 and 260 | 0.121 | 38 | 0.038 | 41 |
| pKK223-3-CFP-T7-H125F | H125F | 258 and 260 | 0.186 | 59 | 0.077 | 83 |
| pKK223-3-CFP-T7-H125Y | H125Y | 259 and 260 | 0.177 | 56 | 0.088 | 95 |

TABLE 10

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-S154E | S154E | 29 and 30 | 0.162 | 51 | 0.047 | 51 |
| pKK223-3-CFP-T7-S154G | S154G | 135 and 136 | 0.186 | 59 | 0.054 | 58 |
| pKK223-3-CFP-T7-S154Y | S154Y | 137 and 138 | 0.188 | 59 | 0.058 | 62 |
| pKK223-3-CFP-T7-S154N | S154N | 139 and 140 | 0.146 | 46 | 0.050 | 54 |
| pKK223-3-CFP-T7-S154Q | S154Q | 141 and 142 | 0.150 | 47 | 0.049 | 53 |
| pKK223-3-CFP-T7-S154D | S154D | 143 and 144 | 0.212 | 67 | 0.066 | 71 |
| pKK223-3-CFP-T7-S154H | S154H | 145 and 146 | 0.127 | 40 | 0.040 | 43 |
| pKK223-3-CFP-T7-S154A | S154A | 147 and 148 | 0.318 | 101 | 0.098 | 105 |
| pKK223-3-CFP-T7-S154C | S154C | 149 and 150 | 0.151 | 48 | 0.059 | 63 |

As shown in Table 10, the ε-FK/α-FVH value of the modified amadoriase resulting from substitution of serine at position 154 in the amino acid sequence as shown in SEQ ID NO: 1 with glutamic acid, glycine, tyrosine, asparagine, glutamine, aspartic acid, histidine, or cysteine was lower than the value before modification (i.e., 0.316), and the ε-FK/α-FV value was lower than the value before modification (i.e., 0.093). Such amino acid substitution was found to be effective for production of an amadoriase having improved substrate specificity. In contrast, the ε-FK/α-FVH value of the modified amadoriase resulting from substitution of serine at position 154 in the amino acid sequence as shown in SEQ ID NO: 1 with alanine was substantially the same as the value before modification (i.e., 0.316), and no reduction was observed in the ε-FK/α-FVH value.

EXAMPLE 11

(Test for Point Mutation of Valine at Position 259)

Valine at position 259 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 11 (SEQ ID NOs: 151 to 154), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of valine at position 259 in the amino acid sequence as shown in SEQ ID NO: 1 with any of various types of amino acids were obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 11.

TABLE 11

| Plasmid | Amino acid mutation | SEQ ID NO: of oligonucleotide | ε-FK/α-FVH | Ratio of ε-FK/α-FVH (%) | ε-FK α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-V259A | V259A | 33 and 34 | 0.080 | 25 | 0.029 | 31 |
| pKK223-3-CFP-T7-V259C | V259C | 151 and 152 | 0.099 | 31 | 0.037 | 40 |
| pKK223-3-CFP-T7-V259S | V259S | 153 and 154 | 0.094 | 30 | 0.033 | 35 |

As shown in Table 11, the ε-FK/α-FVH value of the modified amadoriase resulting from substitution of valine at position 259 in the amino acid sequence as shown in SEQ ID NO: 1 with alanine, cysteine, or serine was lower than the value before modification (i.e., 0.316), and the ε-FK/α-FV value was lower than the value before modification (i.e., 0.093). Such amino acid substitution was found to be effective for production of an amadoriase having improved substrate specificity.

EXAMPLE 12

(Test for Point Mutation of Tyrosine at Position 261)

Tyrosine at position 261 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 12 (SEQ ID NOs: 155 to 162), and KOD-Plus-(Toyobo Co., Ltd.), E. coli JM109 strains were transformed, and the nucleotide sequences of DNAs encoding amadoriases in plasmid DNAs of the grown colonies were determined. As a result, E. coli JM109 strains producing modified amadoriases resulting from substitution of tyrosine at position 261 in the amino acid sequence as shown in SEQ ID NO: 1 with any of various types of amino acids were obtained.

The E. coli JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 12.

of the grown colonies were determined. As a result, E. coli JM109 strains producing modified amadoriases resulting from substitution of glycine at position 263 in the amino acid sequence as shown in SEQ ID NO: 1 with any of various types of amino acids were obtained.

The E. coli JM109 strains capable of producing modified amadoriases thus obtained were cultured by the method

TABLE 12

| Plasmid | Amino acid mutation | SEQ ID NO: of oligonucleotide | ε-FK/ α-FVH | Ratio of ε-FK/α-FVH (%) | ε-FK/ α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-Y261A | Y261A | 35 and 36 | 0.145 | 46 | Not measured | |
| pKK223-3-CFP-T7-Y261L | Y261L | 155 and 156 | 0.087 | 28 | Not measured | |
| pKK223-3-CFP-T7-Y261F | Y261F | 157 and 158 | 0.039 | 12 | 0.032 | 34 |
| pKK223-3-CFP-T7-Y261W | Y261W | 159 and 160 | 0.018 | 6 | 0.015 | 16 |
| pKK223-3-CFP-T7-Y261K | Y261K | 161 and 162 | 0.020 | 6 | Not measured | |

As shown in Table 12, the ε-FK/α-FVH value of the modified amadoriase resulting from substitution of tyrosine at position 261 in the amino acid sequence as shown in SEQ ID NO: 1 with alanine, leucine, phenylalanine, tryptophan, or lysine was lower than the value before modification (i.e., 0.316), and the ε-FK/α-FV value of the modified amadoriase resulting from substitution of tyrosine at position 261 with phenylalanine or tryptophan was lower than the value before modification (i.e., 0.093). Such amino acid substitution was described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 13.

TABLE 13

| Plasmid | Amino acid mutation | SEQ ID NO: of oligonucleotide | ε-FK/ α-FVH | Ratio of ε-FK/α-FVH (%) | ε-FK/ α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-G263R | G263R | 37 and 38 | 0.123 | 39 | 0.055 | 59 |
| pKK223-3-CFP-T7-G263K | G263K | 163 and 164 | 0.107 | 34 | 0.046 | 49 |
| pKK223-3-CFP-T7-G263H | G263H | 261 and 262 | 0.121 | 38 | 0.056 | 60 |
| pKK223-3-CFP-T7-G263D | G263D | 263 and 264 | 0.195 | 62 | 0.080 | 86 |
| pKK223-3-CFP-T7-G263E | G263E | 265 and 266 | 0.211 | 67 | 0.074 | 80 | found to be effective for production of an amadoriase having improved substrate specificity.

EXAMPLE 13

(Test for Point Mutation of Glycine at Position 263)

Glycine at position 263 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 13 (SEQ ID NOs: 163, 164, and 261 to 266), and KOD-Plus-(Toyobo Co., Ltd.), E. coli JM109 strains were transformed, and the nucleotide sequences of DNAs encoding amadoriases in plasmid DNAs As shown in Table 13, the ε-FK/α-FVH value of the modified amadoriase resulting from substitution of glycine at position 263 in the amino acid sequence as shown in SEQ ID NO: 1 with arginine, lysine, histidine, aspartic acid, or glutamic acid was lower than the value before modification (i.e., 0.316), and the ε-FK/α-FV value was lower than the value before modification (i.e., 0.093). Such amino acid substitution was found to be effective for production of an amadoriase having improved substrate specificity.

EXAMPLE 14

(Test for Point Mutation of Alanine at Position 355)

Alanine at position 355 in the amino acid sequence as shown in SEQ ID NO: 1 having high potentials for improving substrate specificity was substituted with another amino acid in an attempt to search for a modified amadoriase having excellent substrate specificity. Under the conditions as described in (2) above, PCR was carried out using DNA of the recombinant plasmid pKK223-3-CFP-T7 as a template, the synthetic oligonucleotides shown in Table 14 (SEQ ID NOs: 165 to 168 and 267 to 270), and KOD-Plus-(Toyobo Co., Ltd.), *E. coli* JM109 strains were transformed, and the nucleotide sequences of DNAs encoding amadoriases in plasmid DNAs of the grown colonies were determined. As a result, *E. coli* JM109 strains producing modified amadoriases resulting from substitution of alanine at position 355 in the amino acid sequence as shown in SEQ ID NO: 1 with any of various types of amino acids were obtained.

The *E. coli* JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 14.

tion was found to be effective for production of an amadoriase having improved substrate specificity.

EXAMPLE 15

(Accumulation of Mutations Effective for Improving Substrate Specificity)

Under the conditions as described in (2) above, PCR was carried out using DNAs of various recombinant plasmids shown in Table 15 as templates, synthetic oligonucleotides (SEQ ID NOs: 7, 8, 17, 18, 39, 40, 51, 52, 55, 56, 87, 88, 115, 116, 131, 132, 135, 136, 139, and 140), and KOD-Plus-(Toyobo Co., Ltd.), *E. coli* JM109 strains were transformed, and the nucleotide sequences of DNAs encoding amadoriases in plasmid DNAs of the grown colonies were determined. As a result, *E. coli* JM109 strains producing modified amadoriases resulting from introduction of a multiple amino acid substitutions described in the "Amino acid mutation" column in Table 15 into the amino acid sequence as shown in SEQ ID NO: 1 were obtained.

The *E. coli* JM109 strains capable of producing modified amadoriases thus obtained were cultured by the method

TABLE 14

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pKK223-3-CFP-T7 | None | None | 0.316 | 100 | 0.093 | 100 |
| pKK223-3-CFP-T7-A355K | A355K | 39 and 40 | 0.177 | 56 | 0.048 | 52 |
| pKK223-3-CFP-T7-A355R | A355R | 165 and 166 | 0.121 | 38 | 0.062 | 67 |
| pKK223-3-CFP-T7-A355H | A355H | 167 and 168 | 0.190 | 60 | 0.115 | 124 |
| pKK223-3-CFP-T7-A355D | A355D | 267 and 268 | 0.201 | 64 | 0.122 | 131 |
| pKK223-3-CFP-T7-A355E | A355E | 269 and 270 | 0.218 | 69 | 0.068 | 73 |

As shown in Table 14, the ε-FK/α-FVH value of the modified amadoriase resulting from substitution of alanine at position 355 in the amino acid sequence as shown in SEQ ID NO: 1 with lysine, arginine, histidine, aspartic acid, or glutamic acid was lower than the value before modification (i.e., 0.316), and the ε-FK/α-FV value of the modified amadoriase resulting from substitution of alanine at position 355 with lysine, arginine, or glutamic acid was lower than the value before modification (i.e., 0.093). Such amino acid substitudescribed in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 15.

TABLE 15

| Plasmid | Amino acid mutation | Template plasmid | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|---|
| pKK223-3-CFP-T7 | None | None | None | 0.316 | 100 | 0.093 | 100 |
| pKK223-3-CFP-T7-K66G V67P/E98A | K66G, V67P, E98A | pKK223-3-CFP-T7-K66GV67P | 55 and 56 | 0.069 | 22 | 0.027 | 29 |
| pKK223-3-CFP-T7-K66G V67P/Q110R | K66G, V67P, Q110R | pKK223-3-CFP-T7-Q110R | 7 and 8 | 0.085 | 27 | 0.034 | 37 |
| pKK223-3-CFP-T7-E98A/Q110R | E98A, Q110R | | 55 and 56 | 0.072 | 23 | 0.032 | 34 |
| pKK223-3-CFP-T7-Q110R/H125Q | Q110R, H125Q | | 131 and 132 | 0.073 | 23 | 0.027 | 29 |
| pKK223-3-CFP-T7-Q110R/S154G | Q110R, S154G | | 135 and 136 | 0.090 | 28 | 0.029 | 31 |
| pKK223-3-CFP-T7-Q110R/S154N | Q110R, S154N | | 139 and 140 | 0.064 | 20 | 0.022 | 24 |

TABLE 15-continued

| Plasmid | Amino acid mutation | Template plasmid | SEQ ID NO: of oligonucleotide | ε-FK/ α-FVH | Ratio of ε-FK/α-FVH (%) | ε-FK/ α-FV | Ratio of ε-FK/α-FV (%) |
|---|---|---|---|---|---|---|---|
| pKK223-3-CFP-T7-Q110R/A355K | Q110R, A355K | | 39 and 40 | 0.094 | 30 | 0.042 | 45 |
| pKK223-3-CFP-T7-E98A/G103R | E98A, G103R | pKK223-3-CFP-T7-E98A | 17 and 18 | 0.062 | 20 | 0.029 | 31 |
| pKK223-3-CFP-T7-E98A/S154N | E98A, S154N | pKK223-3-CFP-T7-S154N | 55 and 56 | 0.062 | 20 | 0.023 | 25 |
| pKK223-3-CFP-T7-E98R/S154N | E98R, S154N | pKK223-3-CFP-T7-S154N | 51 and 52 | 0.030 | 9 | 0.011 | 12 |
| pKK223-3-CFP-T7-Q110R/S154C | Q110R, S154C | pKK223-3-CFP-T7-S154C | 115 and 116 | 0.083 | 26 | 0.032 | 34 |
| pKK223-3-CFP-T7-E98A/D106S/S154N | E98A, D106S, S154N | pKK223-3-CFP-T7-E98A/S154N | 87 and 88 | 0.045 | 14 | 0.019 | 20 |
| pKK223-3-CFP-T7-E98A/Q110R/S154N | E98A, Q110R, S154N | pKK223-3-CFP-T7-Q110R/S154N | 55 and 56 | 0.063 | 20 | 0.021 | 23 |
| pKK223-3-CFP-T7-Q110R/H125Q/S154N | Q110R, H125Q, S154N | | 131 and 132 | 0.044 | 14 | 0.019 | 20 |

The modified amadoriases resulting from introduction of multiple amino acid substitutions shown in Table 15 exhibited the ε-FK/α-FVH value and the ε-FK/α-FV value lower than the values attained by introduction of a single amino acid substitution. This demonstrates that combination of introduction of single mutations effective for improving substrate specificity of the amadoriase comprising the amino acid sequence as shown in SEQ ID NO: 1 can further improve substrate specificity.

EXAMPLE 16

(Accumulation of Mutations Effective for Improving Substrate Specificity)

The plasmids L and S shown in Table 16 were double-digested with restriction enzymes KpnI and HindIII. By agarose gel electrophoresis, DNA fragments of about 5.3 kbp and DNA fragments of about 0.8 kbp were separated from the plasmids L and S, respectively, and the DNA fragments were extracted and purified from gels using NucleoSpin Extract II (manufactured by Macherey-Nagel). Subsequently, the DNA fragments were ligated to each other using Ligation high Ver. 2 (Toyobo Co., Ltd.), the *E. coli* JM109 strains were transformed using the ligated plasmid DNA, and the nucleotide sequences of DNAs encoding amadoriases in plasmid DNAs of the grown colonies were determined. As a result, *E. coli* JM109 strains producing modified amadoriases resulting from introduction of a multiple amino acid substitutions described in the "Amino acid mutation" column in Table 16 into the amino acid sequence as shown in SEQ ID NO: 1 were obtained.

The *E. coli* JM109 strains capable of producing modified amadoriases thus obtained were cultured by the method described in (3) above to prepare 0.6 ml each of crude enzyme solutions of various types of modified amadoriases.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. In this case, Reagent 1 (i.e., a peroxidase-4-amino antipyrine solution) with a pH adjusted to 7.0 was used. The results are shown in Table 16.

TABLE 16

| Plasmid | Amino acid mutation | Plasmid L used | Plasmid S used | ε-FK/ α-FVH | Ratio of ε-FK/α-FVH (%) | ε-FK/ α-FV | Ratio of ε-FK/α-FV (%) |
|---|---|---|---|---|---|---|---|
| pKK223-3-CFP-T7 | None | None | None | 0.316 | 100 | 0.093 | 100 |
| pKK223-3-CFP-T7-E98Q/V259A | E98Q, V259A | pKK223-3-CFP-T7-E98Q | pKK223-3-CFP-T7-V259A | 0.020 | 6 | 0.009 | 10 |
| pKK223-3-CFP-T7-E98Q/V259C | E98Q, V259C | | pKK223-3-CFP-T7-V259C | 0.034 | 11 | 0.014 | 15 |
| pKK223-3-CFP-T7-E98H/V259A | E98H, V259A | pKK223-3-CFP-T7-E98H | pKK223-3-CFP-T7-V259A | 0.037 | 12 | 0.015 | 16 |
| pKK223-3-CFP-T7-E98H/V259C | E98H, V259C | | pKK223-3-CFP-T7-V259C | 0.036 | 11 | 0.014 | 15 |
| pKK223-3-CFP-T7-E98R/V259C | E98R, V259C | pKK223-3-CFP-T7-E98R | pKK223-3-CFP-T7-V259C | 0.022 | 7 | 0.008 | 9 |
| pKK223-3-CFP-T7-E98A/V259C | E98A, V259C | pKK223-3-CFP-T7-E98A | pKK223-3-CFP-T7-V259C | 0.044 | 14 | 0.018 | 19 |
| pKK223-3-CFP-T7-E98A/G263R | E98A, G263R | | pKK223-3-CFP-T7-G263R | 0.064 | 20 | 0.030 | 32 |
| pKK223-3-CFP-T7-Q110R/V259A | Q110R, V259A | pKK223-3-CFP-T7-Q110R | pKK223-3-CFP-T7-V259A | 0.035 | 11 | 0.014 | 15 |

TABLE 16-continued

| Plasmid | Amino acid mutation | Plasmid L used | Plasmid S used | ε-FK/ α-FVH | Ratio of ε-FK/α-FVH (%) | ε-FK/ α-FV | Ratio of ε-FK/α-FV (%) |
|---|---|---|---|---|---|---|---|
| pKK223-3-CFP-T7-S154D/V259A | S154D, V259A | pKK223-3-CFP-T7-S154D | pKK223-3-CFP-T7-V259A | 0.054 | 17 | 0.023 | 25 |
| pKK223-3-CFP-T7-E98A/S154N/V259C | E98A, S154N, V259C | pKK223-3-CFP-T7-E98A/S154N | pKK223-3-CFP-T7-V259C | 0.016 | 5 | 0.006 | 6 |
| pKK223-3-CFP-T7-Q110R/S154N/V259A | Q110R, S154N, V259A | pKK223-3-CFP-T7-Q110R/S154N | pKK223-3-CFP-T7-V259A | 0.017 | 5 | 0.007 | 8 |

The modified amadoriases resulting from introduction of multiple amino acid substitutions shown in Table 16 exhibited the ε-FK/α-FVH value and the ε-FK/α-FV value lower than the values attained upon introduction of a single amino acid substitution. This demonstrates that combination of introduction of single mutations effective for improving substrate specificity of the amadoriase comprising the amino acid sequence as shown in SEQ ID NO: 1 can further improve substrate specificity.

EXAMPLE 17

(Production and Purification of Modified Amadoriases)

Wild-type amadoriases, the transformants producing modified amadoriases obtained in the manner described above, the *E. coli* JM109 strain (pKK223-3-CFP-T7-Q110R), the *E. coli* JM109 strain (pKK223-3-CFP-T7-Q110K), the *E. coli* JM109 strain (pKK223-3-CFP-T7-Y261F), the *E. coli* JM109 strain (pKK223-3-CFP-T7-Y261W), the *E. coli* JM109 strain (pKK223-3-CFP-T7-E98A/V259C), and the *E. coli* JM109 strain (pKK223-3-CFP-T7-E98A/S154N/V259C) were inoculated into 40 ml of LB-amp media supplemented with 0.1 mM IPTG, and culture was conducted at 30° C. for 16 hours. The resulting cultured strains were washed with 20 mM HEPES-NaOH buffer (pH 7.0), the washed strains were suspended therein, the resulting suspension was ultrasonically disintegrated, and the resultant was centrifuged at 20,000×g for 10 minutes to prepare 8 ml of a crude enzyme solution.

The prepared crude enzyme solution was allowed to adsorb to 4 ml of Q Sepharose Fast Flow resin (GE Healthcare) equilibrated with 20 mM HEPES-NaOH buffer (pH 7.0), the resin was washed with 80 ml of the same buffer, and proteins adsorbed to the resin were eluted with the aid of 20 mM HEPES-NaOH buffer (pH 7.0) containing 100 mM NaCl to collect fractions exhibiting amadoriase activity.

The obtained fragments exhibiting activity of amadoriases were concentrated using Amicon Ultra-15 (NMWL: 30 K, Millipore). Thereafter, the resultants were applied to HiLoad 26/60 Superdex 200 pg (GE Healthcare) equilibrated with 20 mM HEPES-NaOH buffer (pH 7.0) containing 150 mM NaCl and were then eluted with the same buffer. The fractions exhibiting amadoriase activity were collected to obtain purified samples of wild-type and modified amadoriases. The obtained purified samples were analyzed via SDS-PAGE and found to have been purified to single bands.

With the use of the purified samples of wild-type and modified amadoriases, enzyme activity when α-FVH, ε-FK, and α-FV were used as substrates were measured. In this case, Reagent 1 (i.e., a peroxidase-4-amino antipyrine solution) with a pH adjusted to 7.0 was used. The results are shown in Table 17 and in Table 18. Protein concentration employed for determining the specific activity were measured via the Bradford colorimetric method or via ultraviolet absorption spectrometry utilizing the absorbance at 280 nm. Specific activities determined based on protein concentrations measured by relevant quantification methods were indicated as U/mg and U/$A_{280}$, respectively.

TABLE 17

| Amino acid mutation | Specific activity (α-FVH) (U/mg) | Specific activity (ε-FK) (U/mg) | Specific activity (α-FV) (U/mg) | ε-FK/ α-FVH | Ratio of ε-FK/α-FVH (%) | ε-FK/ α-FV | Ratio of ε-FK/α-FV (%) |
|---|---|---|---|---|---|---|---|
| None | 22.6 | 7.0 | 76.2 | 0.310 | 100 | 0.092 | 100 |
| Q110R | 20.3 | 2.7 | 48.1 | 0.133 | 43 | 0.056 | 61 |
| Q110K | 21.2 | 3.4 | 37.0 | 0.160 | 52 | 0.092 | 100 |

TABLE 18

| Amino acid mutation | Specific activity (α-FVH) (U/$A_{280}$) | Specific activity (ε-FK) (U/$A_{280}$) | Specific activity (α-FV) (U/$A_{280}$) | ε-FK/ α-FVH | Ratio of ε-FK/α-FVH (%) | ε-FK/ α-FV | Ratio of ε-FK/α-FV (%) |
|---|---|---|---|---|---|---|---|
| None | 12.6 | 3.90 | 42.5 | 0.310 | 100 | 0.092 | 100 |
| Y261F | 5.80 | 0.305 | 7.08 | 0.053 | 17 | 0.043 | 47 |
| Y261W | 2.85 | 0.0599 | 3.22 | 0.021 | 7 | 0.019 | 21 |
| E98A, V259C | 12.7 | 0.585 | 31.3 | 0.046 | 15 | 0.019 | 21 |
| E98A, S154N, V259C | 11.4 | 0.197 | 26.4 | 0.017 | 5 | 0.007 | 8 |

As shown in Table 17, the ε-FK/α-FVH value of the modified amadoriase resulting from substitution of glutamine at position 110 in the amino acid sequence as shown in SEQ ID NO: 1 with arginine or lysine was lower than the value before modification (i.e., 0.310), and the ε-FK/α-FV value of the modified amadoriase resulting from substitution of glutamine at position 110 with arginine was lower than the value before modification (i.e., 0.092). As shown in Table 18, the ε-FK/α-FVH value of the modified amadoriase resulting from substitution of tyrosine at position 261 in the amino acid sequence as shown in SEQ ID NO: 1 with phenylalanine or tryptophan, the modified amadoriase resulting from substitution of glutamic acid at position 98 with alanine, and valine at position 259 with cysteine in the amino acid sequence as shown in SEQ ID NO: 1, and the modified amadoriase resulting from substitution of glutamic acid at position 98 with alanine, serine at position 154 with asparagine, and valine at position 259 with cysteine in the amino acid sequence as shown in SEQ ID NO: 1 were lower than the value before modification (i.e., 0.310), and the ε-FK/α-FV value thereof was lower than the value before modification (i.e., 0.092). Such amino acid substitution was found to be effective for production of an amadoriase having improved substrate specificity.

In addition, the ε-FK/α-FVH value and the ε-FK/α-FV value determined by measuring enzyme activity using purified samples of wild-type amadoriase and various types of modified amadoriases were not significantly deviated from the ε-FK/α-FVH value and the ε-FK/α-FV value determined by measuring enzyme activity using crude enzyme solutions of wild-type amadoriase and various types of modified amadoriases. If improvement is observed in substrate specificity when enzyme activity is measured using a crude enzyme solution of modified amadoriases, accordingly, improvement in substrate specificity would also be observed when enzyme activity is measured using a purified sample of a modified amadoriase.

EXAMPLE 18

(Quantification of α-FVH Using Modified Amadoriase)

When α-FVH released from the β-chain amino terminus in HbA1c by a protease or the like is quantified using modified amadoriases, the influence imposed on the measured values by coexisting ε-FK was evaluated.
C: Preparation of Reagent
(4) Reagent 4: Peroxidase-4-Amino Antipyrine Solution Peroxidase (7.5 kU, manufactured by Kikkoman Corporation) and 150 mg of 4-amino antipyrine (manufactured by Tokyo Chemical Industry Co., Ltd.) are dissolved in a 0.15 M potassium phosphate buffer (pH 6.5), and the volume of the solution is fixed at 1,000 ml.
(5) Reagent 5: TOOS Solution TOOS (500 mg, manufactured by Dojindo Laboratories) is dissolved in ion-exchange water, and the volume of the solution is fixed at 100 ml.
(6) Reagent 6: Amadoriase Solution The purified amadoriase comprising the amino acid sequence as shown in SEQ ID NO: 1 and the modified amadoriase resulting from substitution of glutamic acid at position 98, serine at position 154, and valine at position 259 in the amadoriase comprising the amino acid sequence as shown in SEQ ID NO: 1 with alanine, asparagine, and cysteine, respectively, (SEQ ID NO: 271) were dissolved in 0.01 M potassium phosphate buffer (pH 6.5) to adjust the amadoriase concentration at 1.0 U/ml and 2.3 U/ml, respectively, in the solutions.

(7) Reagent 7: α-FVH Solution

α-FVH (625 mg) was dissolved in ion-exchange water, and the volume of the solution is fixed at 10 ml to prepare a 150 mM α-FVH solution. Subsequently, the 150 mM α-FVH solution was diluted with ion-exchange water to prepare 90 μM, 180 μM, 270 μM, 360 μM, and 450 μM α-FVH solutions.
(8) Reagent 8: Model Blood Sample A 150 mM ε-FK solution prepared by dissolving 462 mg of ε-FK in ion-exchange water and fixing the volume of the solution at 10 ml and the α-FVH solution prepared in (7) above were diluted with ion-exchange water. Thus, four types of model blood samples described below were prepared.
Reagent 8-1: 215 μM α-FVH
Reagent 8-2: 215 μM α-FVH and 215 μM ε-FK
Reagent 8-3: 215 μM α-FVH and 1,075 μM ε-FK
Reagent 8-4: 215 μM α-FVH and 2,150 μM ε-FK In the case of a blood sample with a hemoglobin level of 15 g/dl and an HbA1c level of 6.1% (JDS value; 6.5% in terms of NGSP; 46.5 mmol/mol in terms of IFCC), the concentration of α-FVH released from the β-chain amino terminus in HbA1c is 215 μM if the molecular weight of hemoglobin is 65 kDa.
(Confirmation of Capacity for α-FVH Quantification Using Modified Amadoriase)

Reagent 4 (1.8 ml), 100 μl of Reagent 5, and 100 μl of Reagent 6 were mixed, and the resulting mixture was preliminarily heated at 37° C. for 5 minutes. Subsequently, 1,000 μl of Reagent 7 that had been preliminarily heated at 37° C. for 5 minutes was added, the resultant was thoroughly mixed, and the absorbance at 555 nm was then measured using a spectrophotometer (U-3010A, manufactured by Hitachi High-Technologies). The change in absorbance per minute (ΔA555) was determined. A control solution was prepared in the manner as described above, except that 1,000 μl of ion-exchange water was added as a substitute for 1,000 μl of Reagent 7. The results are shown in FIG. 2. As is apparent from FIG. 2, there was a correlation between the α-FVH level and the change in absorbance (ΔA555). Accordingly, the amadoriase comprising the amino acid sequence as shown in SEQ ID NO: 1 and the modified amadoriase comprising the amino acid sequence as shown in SEQ ID NO: 271 were found to be applicable to quantification of α-FVH in a range from 90 μM to 450 μM.
(Quantification of Model Blood Sample Using Modified Amadoriase)

Reagent 4 (1.8 ml), 100 μl of Reagent 5, and 100 μl of Reagent 6 were mixed, and the resulting mixture was preliminarily heated at 37° C. for 5 minutes. Subsequently, 1,000 μl of any of Reagents 8-1 to 8-4 that had been preliminarily heated at 37° C. for 5 minutes was added, the resultant was thoroughly mixed, the absorbance at 555 nm was then measured using a spectrophotometer (U-3010A, manufactured by Hitachi High-Technologies), and the change in absorbance per minute (ΔA555) was determined. A control solution was prepared in the manner as described above, except that 1,000 μl of ion-exchange water was added as a substitute for 1,000 μl of any of Reagent 8-1 to Reagent 8-4. The results are shown in Table 19. As is apparent from Table 19, when measurement was carried out using the amadoriase comprising the amino acid sequence as shown in SEQ ID NO: 1, the observed value was deviated from the true value by a little less than 3% in the presence of α-FVH and ε-FK at the same concentration. The observed value was deviated from the actual value by 8% and 17%, respectively, in the presence of ε-FK at concentration 5 times and 10 times greater than α-FVH, respectively. In contrast, when the modified amadoriase comprising the amino acid sequence as shown in SEQ ID NO: 271 was used, the observed value was deviated from the true value by up to 1% even in the presence of ε-FK at concentration equal to or 5 times greater than α-FVH. Further, the observed value was deviated from the true value by up to 2% in the presence of ε-FK at concentration 10 times greater than α-FVH. With the use of the modified amadoriase comprising the amino acid sequence as shown in SEQ ID NO: 271, accordingly, α-FVH can be accurately and selectively quantified in a sample containing both α-FVH and ε-FK.

vector (manufactured by Novagen, Inc.). Thus, the recombinant plasmid pET22b-AnFX' was obtained.

In order to impart fructosyl peptide oxidase activity to the fructosyl amino acid oxidase derived from *Aspergillus nidulans*, PCR was carried out using the recombinant plasmid pET22b-AnFX' as a template, the synthetic oligonucleotides as shown in SEQ ID NOs: 173 and 174, and KOD-Plus-(Toyobo Co., Ltd.) under the conditions as described above, *E. coli* strains were transformed, and the nucleotide

TABLE 19

| | Amadoriase of SEQ ID NO: 1 | | | | Amadoriase of SEQ ID NO: 271 | | | |
|---|---|---|---|---|---|---|---|---|
| | ΔA555 | | | Ratio of | ΔA555 | | | Ratio of |
| Model blood sample | First measurement | Second measurement | Average | ΔA555 (%) | First measurement | Second measurement | Average | ΔA555 (%) |
| 8-1 | 0.111 | 0.111 | 0.111 | 100.0 | 0.124 | 0.124 | 0.124 | 100.0 |
| 8-2 | 0.115 | 0.113 | 0.114 | 102.7 | 0.123 | 0.122 | 0.123 | 99.2 |
| 8-3 | 0.120 | 0.120 | 0.120 | 108.1 | 0.125 | 0.125 | 0.125 | 100.8 |
| 8-4 | 0.129 | 0.131 | 0.130 | 117.1 | 0.127 | 0.125 | 0.126 | 101.6 |

EXAMPLE 19

(Cloning of Fructosyl Amino Acid Oxidase Gene Derived from *Aspergillus nidulans* and Expression Thereof in *E. Coli*)
(a) Extraction of Total RNA from *Aspergillus nidulans* FGSC A26 Strain

*Aspergillus nidulans* FGSC A26 strains were cultured in liquid media (0.4% yeast extract, 1.0% malt extract, 0.1% tryptone, 0.1% potassium dihydrogen phosphate, 0.05% magnesium sulfate, and 2.0% glucose, pH 6.5) at 30° C. for 24 hours. Thereafter, the recovered strains were disintegrated with liquid nitrogen, and total RNA was prepared using Isogen (manufactured by Nippon Gene Co., Ltd.) in accordance with the instructions. Also, total RNA prepared was treated with DNaseI (manufactured by Invitrogen) to prevent contamination of DNA.
(b) Cloning of cDNA of Fructosyl Amino Acid Oxidase Derived from *Aspergillus nidulans*

Total RNA obtained (1 μg) was subjected to RT-PCR using the PrimeScript RT-PCR kit (manufactured by Takara Bio Inc.) in accordance with the attached protocols. In this case, reverse transcription was carried out using the oligo dT primers included in the kit, and subsequent PCR was carried out using the synthetic oligonucleotides as shown in SEQ ID NOs: 169 and 170. As a result, a cDNA fragment of about 1,300 bp was specifically amplified. Subsequently, the amplified cDNA fragment was subjected to sequence analysis, and this fragment was consequently found to be a nucleotide sequence of 1,317 bp as shown in SEQ ID NO: 171. Also, the amino acid sequence (SEQ ID NO: 172) deduced based on SEQ ID NO: 171 was consistent with the sequence of the fructosyl amino acid oxidase derived from *Aspergillus nidulans* as shown in FIG. 1.
(c) Expression of Fructosyl Amino Acid Oxidase Derived from *Aspergillus nidulans* in *E. Coli*

In order to express fructosyl amino acid oxidase derived from *Aspergillus nidulans* in *E. coli*, subsequently, the following procedures were performed. Since the cDNA fragment cloned above comprised at the 5' terminus and the 3' terminus the NdeI site and the BamHI site derived from the synthetic nucleotides shown in SEQ ID NOs: 169 and 170, the cloned cDNA fragment was treated with two types of restriction enzymes NdeI and BamHI (manufactured by Takara Bio Inc.) and inserted into the NdeI-BamHI site of the pET-22b(+)

sequences of DNAs encoding fructosyl amino acid oxidases in plasmid DNAs of the grown colonies were determined. As a result, the recombinant plasmid encoding the fructosyl amino acid oxidase gene derived from *Aspergillus nidulans* through substitution of serine at position 59 in the amino acid sequence as shown in SEQ ID NO: 172 with glycine was obtained (pET22b-AnFX). The recombinant plasmid pET22b-AnFX was transformed into the *E. coli* BL21 (DE3) strain (manufactured by Nippon Gene Co., Ltd.) to obtain the *E. coli* strain producing fructosyl amino acid oxidase derived from *Aspergillus nidulans*.

The *E. coli* BL21 (DE3) strains producing fructosyl amino acid oxidase derived from *Aspergillus nidulans* obtained above were shake-cultured in LB-amp media supplemented with a reagent for the Overnight Express Autoinduction System 1 (manufactured by Novagen, Inc.) at 30° C. for 18 hours. The resulting cultured strains were suspended in 10 mM potassium phosphate buffer (pH 7.5), the resulting suspension was ultrasonically disintegrated, and the resultant was centrifuged at 20,000×g for 10 minutes to prepare a crude enzyme solution. The crude enzyme solution was subjected to measurement of enzyme activity to α-FV by the method described in the "B: Method of activity measurement" above, and the enzyme activity was found to be 2.2 U/ml. In this case, activity was measured using Reagent 1 with a pH adjusted to 7.5.

EXAMPLE 20

Introduction of Point Mutation into Fructosyl Amino Acid Oxidase Gene Derived from *Aspergillus nidulans*)

For the purpose of introduction of point mutation aimed at improvement of substrate specificity, PCR was carried out using the recombinant plasmid pET22b-AnFX as a template, the synthetic oligonucleotides as shown in SEQ ID NOs: 175 and 176, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmid encoding the fructosyl amino acid oxidase gene derived from *Aspergillus nidulans* through substitution of cysteine at position 153 in the amino acid sequence as shown in SEQ ID NO: 172 with aspartic acid was obtained (pET22b-AnFX-C153D).

For the purpose of introduction of point mutation aimed at improvement of substrate specificity, PCR was carried out using the recombinant plasmid pET22b-AnFX as a template, the synthetic oligonucleotides as shown in SEQ ID NOs: 177 and 178 and those as shown in SEQ ID NOs: 179 and 180, and KOD-Plus-(Toyobo Co., Ltd.) under the conditions as described above, E. coli BL21 (DE3) strains were transformed, and the nucleotide sequences of DNAs encoding fructosyl amino acid oxidases in plasmid DNAs of the grown colonies were determined. As a result, the recombinant plasmids encoding the fructosyl amino acid oxidase gene derived from Aspergillus nidulans through substitution of valine at position 259 in the amino acid sequence as shown in SEQ ID NO: 172 with alanine and cysteine, respectively, were obtained (pET22b-AnFX-V259A and pET22b-AnFX-V259C).

For the purpose of introduction of point mutation aimed at improvement of substrate specificity, PCR was carried out using the recombinant plasmid pET22b-AnFX as a template, the synthetic oligonucleotides as shown in SEQ ID NOs: 181 and 182 and those as shown in SEQ ID NOs: 183 and 184, and KOD-Plus-(Toyobo Co., Ltd.) under the conditions as described above, E. coli BL21 (DE3) strains were transformed, and the nucleotide sequences of DNAs encoding fructosyl amino acid oxidases in plasmid DNAs of the grown colonies were determined. As a result, the recombinant plasmids encoding the fructosyl amino acid oxidase gene derived from Aspergillus nidulans through substitution of glycine at position 263 in the amino acid sequence as shown in SEQ ID NO: 172 with lysine and arginine, respectively, were obtained (pET22b-AnFX-G263K and pET22b-AnFX-G263R).

EXAMPLE 21

(Evaluation of Effects of Improving Substrate Specificity of Fructosyl Amino Acid Oxidase Derived from Aspergillus nidulans into which Point Mutation has been Introduced)

The E. coli BL21 (DE3) strains carrying the recombinant plasmids obtained above (i.e., pET22b-AnFX, pET22b-AnFX-C153D, pET22b-AnFX-V259A, pET22b-AnFX-V259C, pET22b-AnFX-G263K, and pET22b-AnFX-G263R, respectively) were shake-cultured in LB-amp media supplemented with a reagent for the Overnight Express Autoinduction System 1 (manufactured by Novagen, Inc.) at 30° C. for 18 hours. The resulting cultured strains were suspended in 10 mM potassium phosphate buffer (pH 7.5), the resulting suspension was ultrasonically disintegrated, and the resultant was centrifuged at 20,000×g for 10 minutes to prepare a crude enzyme solution. The crude enzyme solution was subjected to measurement of enzyme activity to α-FV, α-FVH, and ε-FK by the method described in the "B: Method of activity measurement" above, and ε-FK/α-FVH and ε-FK/α-FV were determined. In this case, activity was measured using Reagent 1 with a pH adjusted to 7.5. The results are shown in Table 20.

Through substitution of cysteine at position 153 with aspartic acid, valine at position 259 with alanine or cysteine, and glycine at position 263 with lysine or arginine in the amino acid sequence as shown in SEQ ID NO: 172, the ε-FK/α-FVH value and the ε-FK/α-FV value of the fructosyl amino acid oxidase derived from Aspergillus nidulans became lower than those before substitution, as shown in Table 20. Thus, such amino acid substitution was found to be effective for production of an amadoriase having improved substrate specificity.

EXAMPLE 22

(Cloning of Fructosyl Amino Acid Oxidase Gene Derived from Penicillium chrysogenum and Expression Thereof in E. Coli)

(a) Extraction of Total RNA from Penicillium chrysogenum NBRC9251 Strain

Penicillium chrysogenum NBRC9251 strains were cultured in liquid media (0.4% yeast extract, 1.0% malt extract, 0.1% tryptone, 0.1% potassium dihydrogen phosphate, 0.05% magnesium sulfate, and 2.0% glucose, pH 6.5) at 30° C. for 24 hours. Total RNA was thus prepared in the manner as described above.

(b) Cloning of cDNA of Fructosyl Amino Acid Oxidase Derived from Penicillium chrysogenum Total RNA obtained (1 μg) was subjected to RT-PCR in the manner as described above. In this case, reverse transcription was carried out using the oligo dT primers included in the kit, and subsequent PCR was carried out using the synthetic oligonucleotides as shown in SEQ ID NOs: 185 and 186. As a result, a cDNA fragment of about 1,300 bp was specifically amplified. Subsequently, the amplified cDNA fragment was subjected to sequence analysis, and this fragment was consequently found to be a nucleotide sequence of 1,317 bp as shown in SEQ ID NO: 187. Also, the amino acid sequence (SEQ ID NO: 188) deduced based on SEQ ID NO: 187 was consistent with a sequence resulting from substitution of leucine at position 69 with tryptophane and threonine at position 142 with alanine in the sequence of Penicillium janthinellum shown in FIG. 1.

(c) Expression of Fructosyl Amino Acid Oxidase Derived from Penicillium chrysogenum in E. coli In order to express fructosyl amino acid oxidase derived from Penicillium chrysogenum in E. coli, subsequently, the following procedures were performed. Since the cDNA fragment cloned above comprised at the 5' terminus and the 3' terminus the NdeI site and the BamHI site derived from the synthetic nucleotides shown in SEQ ID NOs: 185 and 186, the cloned cDNA fragment was treated with two types of restriction enzymes NdeI and BamHI (manufactured by Takara Bio Inc.) and inserted into the NdeI-BamHI site of the pET-22b(+) vector (manufactured by Novagen, Inc.). Thus, the recombinant plasmid pET22b-PcFX' was obtained.

TABLE 20

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pET22b-AnFX | None | None | 0.124 | 100 | 0.0255 | 100 |
| pET22b-AnFX-C153D | C153D | 175 and 176 | 0.0882 | 71 | 0.0142 | 56 |
| pET22b-AnFX-V259A | V259A | 177 and 178 | 0.0208 | 17 | 0.0051 | 20 |
| pET226-AnFX-V259C | V259C | 179 and 180 | 0.0444 | 36 | 0.0092 | 36 |
| pET22b-AnFX-G263K | G263K | 181 and 182 | 0.0714 | 57 | 0.0175 | 69 |
| pET22b-AnFX-G263R | G263R | 183 and 184 | 0.0684 | 55 | 0.0153 | 60 |

In order to impart fructosyl peptide oxidase activity to the fructosyl amino acid oxidase derived from *Penicillium chrysogenum*, PCR was carried out using the recombinant plasmid pET22b-PcFX' as a template, the synthetic oligonucleotides as shown in SEQ ID NOs: 189 and 190, and KOD-Plus-(Toyobo Co., Ltd.) under the conditions as described above, *E. coli* strains were transformed, and the nucleotide sequences of DNAs encoding fructosyl amino acid oxidases in plasmid DNAs of the grown colonies were determined. As a result, the recombinant plasmid encoding the fructosyl amino acid oxidase gene derived from *Penicillium chrysogenum* through substitution of serine at position 60 in the amino acid sequence as shown in SEQ ID NO: 188 with glycine was obtained (pET22b-PcFX). The resulting recombinant plasmid pET22b-PcFX was transformed into *E. coli* BL21 (DE3), so as to obtain *E. coli* strains producing *Penicillium chrysogenum*-derived fructosyl amino acid oxidase.

The *E. coli* BL21 (DE3) strains producing fructosyl amino acid oxidase derived from *Penicillium chrysogenum* obtained above were shake-cultured in LB-amp media supplemented with a reagent for the Overnight Express Autoinduction System 1 (manufactured by Novagen, Inc.) at 30° C. for 18 hours. The resulting cultured strains were subjected to bacteriolysis using a BugBuster Protein Extraction Reagent (manufactured by Novagen, Inc.), and the resultant was centrifuged at 20,000×g for 10 minutes to prepare a crude enzyme solution. The crude enzyme solution was subjected to measurement of enzyme activity to α-FV by the method described in the "B: Method of activity measurement" above, and the enzyme activity was found to be 0.090 U/ml. In this case, activity was measured using Reagent 1 with a pH adjusted to 7.5.

EXAMPLE 23

(Introduction of Point Mutation into Fructosyl Amino Acid Oxidase Gene Derived from *Penicillium chrysogenum*)

For the purpose of introduction of point mutation aimed at improvement of substrate specificity, PCR was carried out using the recombinant plasmid pET22b-PcFX as a template, the synthetic oligonucleotides as shown in SEQ ID NOs: 191 and 192, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmid encoding the fructosyl amino acid oxidase gene derived from *Penicillium chrysogenum* through substitution of lysine at position 110 in the amino acid sequence as shown in SEQ ID NO: 188 with arginine was obtained (pET22b-PcFX-K110R).

For the purpose of introduction of point mutation aimed at improvement of substrate specificity, PCR was carried out using the recombinant plasmid pET22b-PcFX as a template, the synthetic oligonucleotides as shown in SEQ ID NOs: 193 and 194, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmid encoding the fructosyl amino acid oxidase gene derived from *Penicillium chrysogenum* through substitution of cysteine at position 154 in the amino acid sequence as shown in SEQ ID NO: 188 with aspartic acid was obtained (pET22b-PcFX-C154D).

For the purpose of introduction of point mutation aimed at improvement of substrate specificity, PCR was carried out using the recombinant plasmid pET22b-PcFX as a template, the synthetic oligonucleotides as shown in SEQ ID NOs: 195 and 196, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmid encoding the fructosyl amino acid oxidase gene derived from *Penicillium chrysogenum* through substitution of glycine at position 263 in the amino acid sequence as shown in SEQ ID NO: 188 with lysine was obtained (pET22b-PcFX-G263K).

EXAMPLE 24

(Evaluation of Properties of Fructosyl Amino Acid Oxidase Derived from *Penicillium chrysogenum* into Which Point Mutation has been Introduced)

The *E. coli* BL21 (DE3) strains carrying the recombinant plasmids obtained above (i.e., pET22b-PcFX, pET22b-PcFX-K110R, pET22b-PcFX-C154D, and pET22b-PcFX-G263K, respectively) were shake-cultured in LB-amp media supplemented with a reagent for the Overnight Express Autoinduction System 1 (manufactured by Novagen, Inc.) at 30° C. for 18 hours. The resulting cultured strains were subjected to bacteriolysis using a BugBuster Protein Extraction Reagent (manufactured by Novagen, Inc.), and the resultant was centrifuged at 20,000×g for 10 minutes to prepare a crude enzyme solution. The crude enzyme solution was subjected to measurement of enzyme activity to α-FV, α-FVH, and ε-FK by the method described in the "B: Method of activity measurement" above, and ε-FK/α-FVH and ε-FK/α-FV were determined. In this case, activity was measured using Reagent 1 with a pH adjusted to 7.5. The results are shown in Table 21.

TABLE 21

| Plasmid | Amino acid mutation | SEQ ID NO: of oligonucleotide | ε-FK/ α-FVH | Ratio of ε-FK/α-FVH (%) | ε-FK/ α-FV | Ratio of ε-FK/α-FV (%) |
|---|---|---|---|---|---|---|
| pET22b-PcFX | None | None | 0.0833 | 100 | 0.0085 | 100 |
| pET22b-PcFX-K110R | K110R | 191 and 192 | 0.0353 | 42 | 0.0051 | 59 |
| pET22b-PcFX-C154D | C154D | 193 and 194 | 0.0645 | 77 | 0.0079 | 93 |
| pET22b-PcFX-G263K | G263K | 195 and 196 | 0.0711 | 85 | — | — |

Through substitution of lysine at position 110 with arginine and cysteine at position 154 with aspartic acid in the amino acid sequence as shown in SEQ ID NO: 188, the ε-FK/α-FVH value and the ε-FK/α-FV value of the fructosyl amino acid oxidase derived from *Penicillium chrysogenum* became lower than those before substitution, as shown in Table 21. Through substitution of glycine at position 263 in the amino acid sequence as shown in SEQ ID NO: 188 with lysine, further, the ε-FK/α-FVH value of the fructosyl amino acid oxidase derived from *Penicillium chrysogenum* became lower than that before substitution. Thus, such amino acid substitution was found to be effective for production of an amadoriase having improved substrate specificity.

EXAMPLE 25

(Expression of Fructosyl Amino Acid Oxidase Derived from *Cryptococcus neoformans* in *E. coli*)

Regarding fructosyl amino acid oxidase derived from *Cryptococcus neoformans* (*Cryptococcus neoformans* B-3501A: GENE ID: 4934641 CNBB5450 hypothetical protein) obtained by searching for the genome database (http://www.genome.jp/tools/blast/) on the basis of the amino acid sequence of known fructosyl amino acid oxidase, an attempt was made so as to express a sequence comprising 443 amino acid residues as shown in SEQ ID NO: 197 from which 34 C-terminal amino acid residues have been removed in *E. coli*. The gene comprising a 1,332-bp sequence as shown in SEQ ID NO: 198 (including a termination codon "TGA") encoding the amino acid sequence as shown in SEQ ID NO: 197 and having codons optimized for expression in *E. coli* was obtained by a conventional technique comprising total synthesis of cDNA via PCR of a gene fragment. In this case, the NdeI site and the BamHI site were added to the 5' terminus and the 3' terminus of the sequence as shown in SEQ ID NO: 1. The amino acid sequence deduced based on the cloned gene sequence was found to be consistent with a sequence of the fructosyl amino acid oxidase derived from *Cryptococcus neoformans* shown in FIG. 1 from which 34 C-terminal amino acid residues have been removed.

In order to express the gene comprising a sequence as shown in SEQ ID NO: 198 in *E. coli*, subsequently, the following procedures were performed. Since the gene subjected to total synthesis above was treated with two types of restriction enzymes NdeI and BamHI (manufactured by Takara Bio Inc.) and inserted into the NdeI-BamHI site of the pET-22b(+) vector (manufactured by Novagen, Inc.), the recombinant plasmid pET22b-CnFX was obtained, and the resultant was transformed into *E. coli* BL21 (DE3). Subsequently, the *E. coli* BL21 (DE3) strains carrying the recombinant plasmid pET22b-CnFX were shake-cultured in LB-amp media supplemented with a reagent for the Overnight Express Autoinduction System 1 (manufactured by Novagen, Inc.) at 30° C. for 18 hours. The resulting cultured strains were suspended in 10 mM potassium phosphate buffer (pH 7.5), the resulting suspension was ultrasonically disintegrated, and the resultant was centrifuged at 20,000×g for 10 minutes to prepare a crude enzyme solution. The crude enzyme solution was subjected to measurement of enzyme activity to α-FV by the method described in "B. Method of measuring activity" above, and the enzyme activity was found to be 2.2 U/ml, respectively. In this case, activity was measured using Reagent 1 with a pH adjusted to 7.5.

EXAMPLE 26

(Introduction of Point Mutation into Fructosyl Amino Acid Oxidase Gene Derived from *Cryptococcus neoformans*)

For the purpose of introduction of point mutation aimed at improvement of substrate specificity, PCR was carried out using the recombinant plasmid pET22b-CnFX as a template, the synthetic oligonucleotides as shown in SEQ ID NOs: 199 and 200, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmid encoding the fructosyl amino acid oxidase gene derived from *Cryptococcus neoformans* through substitution of threonine at position 100 in the amino acid sequence as shown in SEQ ID NO: 197 with arginine was obtained (pET22b-CnFX-T100R).

For the purpose of introduction of point mutation aimed at improvement of substrate specificity, PCR was carried out using the recombinant plasmid pET22b-CnFX as a template, the synthetic oligonucleotides as shown in SEQ ID NOs: 201 and 202, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmid encoding the fructosyl amino acid oxidase gene derived from *Cryptococcus neoformans* through substitution of serine at position 110 in the amino acid sequence as shown in SEQ ID NO: 197 with arginine was obtained (pET22b-CnFX-S110R).

For the purpose of introduction of point mutation aimed at improvement of substrate specificity, PCR was carried out using the recombinant plasmid pET22b-CnFX as a template, the synthetic oligonucleotides as shown in SEQ ID NOs: 203 and 204, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmid encoding the fructosyl amino acid oxidase gene derived from *Cryptococcus neoformans* through substitution of serine at position 154 in the amino acid sequence as shown in SEQ ID NO: 197 with asparagine was obtained (pET22b-CnFX-S154N).

For the purpose of introduction of point mutation aimed at improvement of substrate specificity, PCR was carried out using the recombinant plasmid pET22b-CnFX as a template, the synthetic oligonucleotides as shown in SEQ ID NOs: 205 and 206 and those as shown in SEQ ID NOs: 207 and 208, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmids encoding the fructosyl amino acid oxidase gene derived from *Cryptococcus neoformans* through substitution of valine at position 259 in the amino acid sequence as shown in SEQ ID NO: 197 with alanine and cysteine, respectively, were obtained (pET22b-CnFX-V259A and pET22b-CnFX-V259C).

For the purpose of introduction of point mutation aimed at improvement of substrate specificity, PCR was carried out using the recombinant plasmid pET22b-CnFX as a template, the synthetic oligonucleotides as shown in SEQ ID NOs: 209 and 210 and those as shown in SEQ ID NOs: 211 and 212, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmids encoding the fructosyl amino acid oxidase gene derived from *Cryptococcus neoformans* through substitution of serine at position 263 in the amino acid sequence as shown in SEQ ID NO: 197 with lysine and arginine, respectively, were obtained (pET22b-CnFX-S263K and pET22b-CnFX-S263R).

EXAMPLE 27

(Evaluation of Properties of Fructosyl Amino Acid Oxidase Derived from *Cryptococcus neoformans* into Which Point Mutation has been Introduced)

The *E. coli* BL21 (DE3) strains carrying the recombinant plasmids obtained above (i.e., pET22b-CnFX-T100R, pET22b-CnFX-S110R, pET22b-CnFX-S154N, pET22b-CnFX-V259A, pET22b-CnFX-V259C, pET22b-CnFX-S263K, and pET22b-CnFX-S263R, respectively) were shake-cultured in LB-amp media supplemented with a reagent for the Overnight Express Autoinduction System 1 (manufactured by Novagen, Inc.) at 30° C. for 18 hours. The resulting cultured strains were suspended in 10 mM potassium phosphate buffer (pH 7.5), the resulting suspension was ultrasonically disintegrated, and the resultant was centrifuged at 20,000×g for 10 minutes to prepare a crude enzyme solution. The crude enzyme solution was subjected to measurement of enzyme activity to α-FV, α-FVH and ε-FK by the method described in "B. Method of measuring activity" above, and ε-FK/α-FVH and ε-FK/α-FV were determined. In this case, activity was measured using Reagent 1 with a pH adjusted to 7.5. The results are shown in Table 22.

TABLE 22

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pET22b-CnFX | None | None | 0.0647 | 100 | 0.0197 | 100 |
| pET22b-CnFX-T100R | T100R | 199 and 200 | 0.0584 | 90 | 0.0168 | 85 |
| pET22b-CnFX-S110R | S110R | 201 and 202 | 0.0468 | 72 | 0.0136 | 69 |
| pET22b-CnFX-S154N | S154N | 203 and 204 | 0.0552 | 85 | 0.0180 | 91 |
| pET22b-CnFX-V259A | V259A | 205 and 206 | 0.0353 | 55 | 0.0116 | 59 |
| pET22b-CnFX-V259C | V259C | 207 and 208 | 0.0284 | 44 | 0.0085 | 43 |
| pET22b-CnFX-S263K | S263K | 209 and 210 | 0.0583 | 90 | 0.0171 | 87 |
| pET22b-CnFX-S263R | S263R | 211 and 212 | 0.0543 | 84 | 0.0156 | 79 |

Through substitution of threonine at position 100 with arginine, serine at position 110 with arginine, serine at position 154 with asparagine, valine at position 259 with alanine or cysteine, and serine at position 263 with lysine or arginine in the amino acid sequence as shown in SEQ ID NO: 197, the ε-FK/α-FVH value and the ε-FK/α-FV value of the fructosyl amino acid oxidase derived from *Cryptococcus neoformans* became lower than those before substitution, as shown in Table 22. Thus, such amino acid substitution was found to be effective for production of an amadoriase having improved substrate specificity.

EXAMPLE 28

(Expression of Ketoamine Oxidase Derived from *Neocosmospora vasinfecta* in *E. coli*)

An attempt was made so as to express ketoamine oxidase derived from *Neocosmospora vasinfecta* in *E. coli*. The amino acid sequence of ketoamine oxidase derived from *Neocosmospora vasinfecta*, which has already been revealed, is shown in SEQ ID NO: 213 (see Patent Document 1). The gene comprising a 1,326-bp sequence as shown in SEQ ID NO: 214 (including a termination codon "TGA") encoding a sequence comprising 441 amino acid residues as shown in SEQ ID NO: 213 and having codons optimized for expression in *E. coli* was obtained by a conventional technique comprising total synthesis of cDNA via PCR of a gene fragment. In this case, the NdeI site and the BamHI site were added to the 5' terminus and the 3' terminus of the sequence as shown in SEQ ID NO: 1. A full-length amino acid sequence deduced based on the cloned gene sequence was found to be consistent with a sequence of the ketoamine oxidase derived from *Neocosmospora vasinfecta* shown in FIG. 1.

In order to express the gene comprising a sequence as shown in SEQ ID NO: 214 in *E. coli*, subsequently, the following procedures were performed. Since the gene subjected to total synthesis above was treated with two types of restriction enzymes NdeI and BamHI (manufactured by Takara Bio Inc.) and inserted into the NdeI-BamHI site of the pET-22b(+) vector (manufactured by Novagen, Inc.), the recombinant plasmid pET22b-NvFX was obtained, and the resultant was transformed into *E. coli* BL21 (DE3). Subsequently, the *E. coli* BL21 (DE3) strains carrying the recombinant plasmid pET22b-NvFX were shake-cultured in LB-amp media supplemented with a reagent for the Overnight Express Autoinduction System 1 (manufactured by Novagen, Inc.) at 30° C. for 18 hours. The resulting cultured strains were suspended in 10 mM potassium phosphate buffer (pH 7.5), the resulting suspension was ultrasonically disintegrated, and the resultant was centrifuged at 20,000×g for 10 minutes to prepare a crude enzyme solution. The crude enzyme solution was subjected to measurement of enzyme activity to α-FV by the method described in "B. Method of measuring activity" above, and the enzyme activity was found to be 19.3 U/ml. In this case, activity was measured using Reagent 1 with a pH adjusted to 7.5.

EXAMPLE 29

(Introduction of Point Mutation into Ketoamine Oxidase Gene Derived from *Neocosmospora vasinfecta*)

For the purpose of introduction of point mutation aimed at improvement of substrate specificity, PCR was carried out using the recombinant plasmid pET22b-NvFX as a template, the synthetic oligonucleotides as shown in SEQ ID NOs: 215 and 216, those as shown in SEQ ID NOs: 217 and 218, those as shown in SEQ ID NOs: 219 and 220, and those as shown in SEQ ID NOs: 221 and 222, and KOD-Plus-(Toyobo Co., Ltd.) under the conditions as described above, *E. coli* BL21 (DE3) strains were transformed, and the nucleotide sequences of DNAs encoding fructosyl amino acid oxidases in plasmid DNAs of the grown colonies were determined. As a result, the recombinant plasmids encoding the ketoamine oxidase gene derived from *Neocosmospora vasinfecta* through substitution of glutamic acid at position 98 in the amino acid sequence as shown in SEQ ID NO: 213 with glutamine, histidine, lysine, and arginine, respectively, were obtained (pET22b-NvFX-E98Q, pET22b-NvFX-E98H, pET22b-NvFX-E98K, and pET22b-NvFX-E98R).

For the purpose of introduction of point mutation aimed at improvement of substrate specificity, PCR was carried out using the recombinant plasmid pET22b-NvFX as a template, the synthetic oligonucleotides as shown in SEQ ID NOs: 223 and 224, and KOD-Plus-(Toyobo Co., Ltd.) under the conditions as described above, *E. coli* BL21 (DE3) strains were transformed, and the nucleotide sequences of DNAs encoding ketoamine oxidases in plasmid DNAs of the grown colonies were determined. As a result, the recombinant plasmid encoding the ketoamine oxidase gene derived from *Neocosmospora vasinfecta* through substitution of glycine at position 103 in the amino acid sequence as shown in SEQ ID NO: 213 with arginine was obtained (pET22b-NvFX-G103R).

For the purpose of introduction of point mutation aimed at improvement of substrate specificity, PCR was carried out using the recombinant plasmid pET22b-NvFX as a template, the synthetic oligonucleotides as shown in SEQ ID NOs: 225 and 226, and KOD-Plus-(Toyobo Co., Ltd.) under the conditions as described above, *E. coli* BL21 (DE3) strains were transformed, and the nucleotide sequences of DNAs encoding ketoamine oxidases in plasmid DNAs of the grown colonies were determined. As a result, the recombinant plasmid encoding the ketoamine oxidase gene derived from *Neocosmospora vasinfecta* through substitution of glutamic acid at position 110 in the amino acid sequence as shown in SEQ ID NO: 213 with arginine was obtained (pET22b-NvFX-E110R).

For the purpose of introduction of point mutation aimed at improvement of substrate specificity, PCR was carried out using the recombinant plasmid pET22b-NvFX as a template, the synthetic oligonucleotides as shown in SEQ ID NOs: 227 and 228 and those as shown in SEQ ID NOs: 229 and 230, and KOD-Plus-(Toyobo Co., Ltd.) under the conditions as described above, *E. coli* BL21 (DE3) strains were transformed, and the nucleotide sequences of DNAs encoding ketoamine oxidases in plasmid DNAs of the grown colonies were determined. As a result, the recombinant plasmids encoding the ketoamine oxidase gene derived from *Neocosmospora vasinfecta* through substitution of serine at position 154 in the amino acid sequence as shown in SEQ ID NO: 213 with asparagine and aspartic acid, respectively, were obtained (pET22b-NvFX-S154N and pET22b-NvFX-S154D).

For the purpose of introduction of point mutation aimed at improvement of substrate specificity, PCR was carried out using the recombinant plasmid pET22b-NvFX as a template, the synthetic oligonucleotides as shown in SEQ ID NOs: 231 and 232 and those as shown in SEQ ID NOs: 233 and 234, and KOD-Plus-(Toyobo Co., Ltd.) under the conditions as described above, *E. coli* BL21 (DE3) strains were transformed, and the nucleotide sequences of DNAs encoding ketoamine oxidases in plasmid DNAs of the grown colonies were determined. As a result, the recombinant plasmids encoding the ketoamine oxidase gene derived from *Neocosmospora vasinfecta* through substitution of valine at position 259 in the amino acid sequence as shown in SEQ ID NO: 213 with alanine and cysteine, respectively, were obtained (pET22b-NvFX-V259A and pET22b-NvFX-V259C).

For the purpose of introduction of point mutation aimed at improvement of substrate specificity, PCR was carried out using the recombinant plasmid pET22b-NvFX as a template, the synthetic oligonucleotides as shown in SEQ ID NOs: 235 and 236 and those as shown in SEQ ID NOs: 237 and 238, and KOD-Plus-(Toyobo Co., Ltd.) under the conditions as described above, *E. coli* BL21 (DE3) strains were transformed, and the nucleotide sequences of DNAs encoding ketoamine oxidases in plasmid DNAs of the grown colonies were determined. As a result, the recombinant plasmids encoding the ketoamine oxidase gene derived from *Neocosmospora vasinfecta* through substitution of glycine at position 263 in the amino acid sequence as shown in SEQ ID NO: 213 with lysine and arginine, respectively, were obtained (pET22b-NvFX-G263K and pET22b-NvFX-G263R).

For the purpose of introduction of point mutation aimed at improvement of substrate specificity, PCR was carried out using the recombinant plasmid pET22b-NvFX as a template, the synthetic oligonucleotides as shown in SEQ ID NOs: 239 and 240, and KOD-Plus-(Toyobo Co., Ltd.) under the conditions as described above, *E. coli* BL21 (DE3) strains were transformed, and the nucleotide sequences of DNAs encoding ketoamine oxidases in plasmid DNAs of the grown colonies were determined. As a result, the recombinant plasmids encoding the ketoamine oxidase gene derived from *Neocosmospora vasinfecta* through substitution of lysine at position 66 and valine at position 67 in the amino acid sequence as shown in SEQ ID NO: 213 with glycine and proline, respectively, were obtained (pET22b-NvFX-K66GV67P).

EXAMPLE 30

(Evaluation of Properties of Ketoamine Oxidase Derived from *Neocosmospora vasinfecta* into Which Point Mutation has been Introduced)

The *E. coli* BL21 (DE3) strains carrying the recombinant plasmids obtained above (i.e., pET22b-NvFX-E98Q, pET22b-NvFX-E98H, pET22b-NvFX-E98K, pET22b-NvFX-E98R, pET22b-NvFX-E110R, pET22b-NvFX-S154N, pET22b-NvFX-S154D, pET22b-NvFX-V259A, pET22b-NvFX-V259C, pET22b-NvFX-G263K, pET22b-NvFX-G263R, and pET22b-NvFX-K66GV67P, respectively) were shake-cultured in LB-amp media supplemented with a reagent for the Overnight Express Autoinduction System 1 (manufactured by Novagen, Inc.) at 30° C. for 18 hours. The resulting cultured strains were suspended in 10 mM potassium phosphate buffer (pH 7.5), the resulting suspension was ultrasonically disintegrated, and the resultant was centrifuged at 20,000×g for 10 minutes to prepare a crude enzyme solution. The crude enzyme solution was subjected to measurement of enzyme activity to α-FV, α-FVH, and ε-FK by the method described in "B. Method of measuring activity" above, and ε-FK/α-FVH and ε-FK/α-FV were determined. In this case, activity was measured using Reagent 1 with a pH adjusted to 7.5. The results are shown in Table 23.

TABLE 23

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pET22b-NvFX | None | None | 2.32 | 100 | 0.707 | 100 |
| pET22b-NvFX-E98Q | E98Q | 215 and 216 | 1.45 | 63 | 0.585 | 83 |
| pET22b-NvFX-E98H | E98H | 217 and 218 | 1.41 | 61 | 0.601 | 85 |
| pET22b-NvFX-E98K | E98K | 219 and 220 | 0.691 | 30 | 0.239 | 34 |
| pET22b-NvFX-E98R | E98R | 221 and 222 | 0.840 | 36 | 0.237 | 33 |
| pET22b-NvFX-G103R | G103R | 223 and 224 | 1.65 | 71 | 0.579 | 82 |
| pET22b-NvFX-E110R | E110R | 225 and 226 | 0.474 | 20 | 0.178 | 25 |
| pET22b-NvFX-S154N | S154N | 227 and 228 | 1.32 | 57 | 0.359 | 51 |
| pET22b-NvFX-S154D | S154D | 229 and 230 | 1.67 | 72 | 0.494 | 70 |
| pET22b-NvFX-V259A | V259A | 231 and 232 | 1.33 | 57 | 0.431 | 61 |

TABLE 23-continued

| Plasmid | Amino acid mutation | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|
| pET22b-NvFX-V259C | V259C | 233 and 234 | 1.27 | 55 | 0.474 | 67 |
| pET22b-NvFX-G263K | G263K | 235 and 236 | 0.974 | 42 | 0.324 | 46 |
| pET22b-NvFX-G263R | G263R | 237 and 238 | 0.972 | 42 | 0.315 | 45 |
| pET22b-NvFX-K66GV67P | K66G, V67P | 239 and 240 | 2.10 | 90 | — | — |

Through substitution of glutamic acid at position 98 with glutamine, histidine, lysine, or arginine, glycine at position 103 with arginine, glutamic acid at position 110 with arginine, serine at position 154 with asparagine or aspartic acid, valine at position 259 with alanine or cysteine, and glycine at position 263 with lysine or arginine in the amino acid sequence as shown in SEQ ID NO: 213, the ε-FK/α-FVH value and the ε-FK/α-FV value of the fructosyl amino acid oxidase derived from *Neocosmospora vasinfecta* became lower than those before substitution, as shown in Table 23. Through substitution of lysine at position 66 with glycine and valine at position 67 with proline, also, the ε-FK/α-FVH value of ketoamine oxidase derived from *Neocosmospora vasinfecta* became lower than that before substitution. Thus, such amino acid substitution was found to be effective for production of an amadoriase having improved substrate specificity.

EXAMPLE 31

(Introduction of Point Mutation into Amadoriase Gene Derived from *Eupenicillium terrenum*)

SEQ ID NO: 241 shows an amino acid sequence of an amadoriase derived from *Eupenicillium terrenum* into which mutations aimed at improvement of the thermostability (G184D, N272D, and H388Y) had been introduced. The recombinant plasmid pUTE100K'-EFP-T5 into which the gene encoding the amino acid sequence as shown in SEQ ID NO: 241 (SEQ ID NOs: 242) had been inserted was expressed in *E. coli*, and, consequently, activity of an amadoriase derived from *Eupenicillium terrenum* was confirmed (see WO 2007/125779).

For the purpose of introduction of mutations aimed at improvement of the substrate specificity into the amadoriase derived from *Eupenicillium terrenum*, PCR was carried out using the recombinant plasmid pUTE100K'-EFP-T5 as a template, the synthetic oligonucleotides as shown in SEQ ID NOs: 243 and 244, and KOD-Plus-(Toyobo Co., Ltd.) under the conditions as described above, *E. coli* DH5a strains were transformed, and the nucleotide sequences of DNAs encoding amadoriases in plasmid DNAs of the grown colonies were determined. As a result, the recombinant plasmid encoding the amadoriase gene derived from *Eupenicillium terrenum* through substitution of serine at position 98 in the amino acid sequence as shown in SEQ ID NO: 241 with alanine was obtained (pUTE100K'-EFP-T5-S98A).

For the purpose of introduction of point mutation aimed at improvement of substrate specificity, PCR was carried out using the recombinant plasmid pUTE100K'-EFP-T5 as a template, the synthetic oligonucleotides as shown in SEQ ID NOs: 245 and 246, and KOD-Plus-(Toyobo Co., Ltd.) under the conditions as described above, *E. coli* DH5a strains were transformed, and the nucleotide sequences of DNAs encoding amadoriases in plasmid DNAs of the grown colonies were determined. As a result, the recombinant plasmid encoding the amadoriase gene derived from *Eupenicillium terrenum* through substitution of lysine at position 110 in the amino acid sequence as shown in SEQ ID NO: 241 with arginine was obtained (pUTE100K'-EFP-T5-K110R).

For the purpose of introduction of point mutation aimed at improvement of substrate specificity, PCR was carried out using the recombinant plasmid pUTE100K'-EFP-T5 as a template, the synthetic oligonucleotides as shown in SEQ ID NOs: 249 and 250 and those as shown in SEQ ID NOs: 251 and 252, and KOD-Plus-(Toyobo Co., Ltd.) under the conditions as described above, *E. coli* DH5a strains were transformed, and the nucleotide sequences of DNAs encoding amadoriases in plasmid DNAs of the grown colonies were determined. As a result, the recombinant plasmids encoding the amadoriase gene derived from *Eupenicillium terrenum* through substitution of valine at position 259 in the amino acid sequence as shown in SEQ ID NO: 241 with alanine and cysteine, respectively, were obtained (pUTE100K'-EFP-T5-V259A and pUTE100K'-EFP-T5-V259C).

For the purpose of introduction of point mutation aimed at improvement of substrate specificity, PCR was carried out using the recombinant plasmid pUTE100K'-EFP-T5 as a template, the synthetic oligonucleotides as shown in SEQ ID NOs: 253 and 254, and KOD-Plus-(Toyobo Co., Ltd.) under the conditions as described above, *E. coli* DH5α strains were transformed, and the nucleotide sequences of DNAs encoding amadoriases in plasmid DNAs of the grown colonies were determined. As a result, the recombinant plasmid encoding the amadoriase gene derived from *Eupenicillium terrenum* through substitution of glycine at position 263 in the amino acid sequence as shown in SEQ ID NO: 241 with lysine was obtained (pUTE 100K'-EFP-T5-G263K).

EXAMPLE 32

(Evaluation of Effects of Improving Substrate Specificity of Amadoriase Derived from *Eupenicillium terrenum* into which Point Mutation has been Introduced)

The *E. coli* DH5α strains carrying the recombinant plasmids obtained above (i.e., pUTE100K'-EFP-T5-S98A, pUTE100K'-EFP-T5-K110R, pUTE100K'-EFP-T5-V259A, pUTE100K'-EFP-T5-V259C, and pUTE100K'-EFP-T5-G263K, respectively) were shake-cultured in LB-amp media supplemented with 0.1 M IPTG at 30° C. for 18 hours. The resulting cultured strains were suspended in 10 mM potassium phosphate buffer (pH 7.5), the resulting suspension was ultrasonically disintegrated, and the resultant was centrifuged at 20,000×g for 10 minutes to prepare a crude enzyme solution. The crude enzyme solution was subjected to measurement of enzyme activity to α-FV, α-FVH, and ε-FK by the method described in "B. Method of measuring activity" above, and ε-FK/α-FVH and ε-FK/α-FV were determined. Activity was measured using Reagent 1 with a pH adjusted to 8.0. The results are shown in Table 24.

TABLE 24

| Plasmid | Amino acid mutation | SEQ ID NO: of oligonucleotide | ε-FK/ ε-FVH | Ratio of Δ-FK/α-FVH (%) | ε-FK/ α-FV | Ratio of ε-FK/α-FV (%) |
|---|---|---|---|---|---|---|
| pUTE100K'-EFP-T5 | None | None | 0.107 | 100 | 0.0206 | 100 |
| pUTE100K'-EFP-T5-S98A | S98A | 243 and 244 | 0.0825 | 77 | 0.0151 | 73 |
| pUTE100K'-EFP-T5-K110R | K110R | 245 and 246 | 0.0893 | 83 | 0.0204 | 99 |
| pUTE100K'-EFP-T5-V259A | V259A | 249 and 250 | 0.0769 | 72 | 0.0172 | 84 |
| pUTE100K'-EFP-T5-V259C | V259C | 251 and 252 | 0.0333 | 31 | 0.0068 | 33 |
| pUTE100K'-EFP-T5-G263K | G263K | 253 and 254 | 0.0909 | 85 | 0.0139 | 68 |

Through substitution of serine at position 98 with alanine, lysine at position 110 with arginine, valine at position 259 with alanine or cysteine, and glycine at position 263 with lysine in the amino acid sequence as shown in SEQ ID NO: 241, the ε-FK/α-FVH value and the ε-FK/α-FV value of the amadoriase derived from *Eupenicillium terrenum* became lower than those before substitution, as shown in Table 24. Thus, such amino acid substitution was found to be effective for production of an amadoriase having improved substrate specificity.

EXAMPLE 33

(Production of a Plurality of Mutant of Amadoriase Gene Derived from *Eupenicillium terrenum* Aimed at Improvement of Substrate Specificity)

A plurality of mutants of the amadoriase gene derived from *Eupenicillium terrenum* aimed at improvement of substrate specificity were produced in an attempt to develop amadoriases having significantly lowered activity to ε-FK.

PCR was carried out using the recombinant plasmid pUTE100K'-EFP-T5-V259C as a template, the synthetic oligonucleotides as shown in SEQ ID NOs: 243 and 244, and KOD-Plus-(Toyobo Co., Ltd.) under the conditions as described above, *E. coli* DH5a strains were transformed, and the nucleotide sequences of DNAs encoding amadoriases in plasmid DNAs of the grown colonies were determined. As a result, the recombinant plasmid encoding the amadoriase gene derived from *Eupenicillium terrenum* through substitution of serine at position 98 with alanine and valine at position 259 with cysteine in the amino acid sequence as shown in SEQ ID NO: 241 was obtained (pUTE100K'-EFP-T5-S98A/V259C).

For the purpose of introduction of point mutation aimed at improvement of substrate specificity, PCR was carried out using the recombinant plasmid pUTE100K'-EFP-T5-K110R as a template, the synthetic oligonucleotides as shown in SEQ ID NOs: 247 and 248, and KOD-Plus-(Toyobo Co., Ltd.) under the conditions as described above, *E. coli* DH5a strains were transformed, and the nucleotide sequences of DNAs encoding amadoriases in plasmid DNAs of the grown colonies were determined. As a result, the recombinant plasmid encoding the amadoriase gene derived from *Eupenicillium terrenum* through substitution of lysine at position 110 with arginine and cysteine at position 154 with asparagine in the amino acid sequence as shown in SEQ ID NO: 241 was obtained (pUTE100K'-EFP-T5-K110R/C154N).

PCR was carried out using the recombinant plasmid pUTE100K'-EFP-T5-V259C as a template, the synthetic oligonucleotides as shown in SEQ ID NOs: 245 and 246, and KOD-Plus-(Toyobo Co., Ltd.) under the conditions as described above, *E. coli* DH5a strains were transformed, and the nucleotide sequences of DNAs encoding amadoriases in plasmid DNAs of the grown colonies were determined. As a result, the recombinant plasmid encoding the amadoriase gene derived from *Eupenicillium terrenum* through substitution of lysine at position 110 with arginine and valine at position 259 with cysteine in the amino acid sequence as shown in SEQ ID NO: 241 was obtained (pUTE100K'-EFP-T5-K110RN259C).

PCR was carried out using the recombinant plasmid pUTE100K'-EFP-T5-S98A-V259C as a template, the synthetic oligonucleotides as shown in SEQ ID NOs: 245 and 246, and KOD-Plus-(Toyobo Co., Ltd.) under the conditions as described above, *E. coli* DH5α strains were transformed, and the nucleotide sequences of DNAs encoding amadoriases in plasmid DNAs of the grown colonies were determined. As a result, the recombinant plasmid encoding the amadoriase gene derived from *Eupenicillium terrenum* through substitution of serine at position 98 with alanine, lysine at position 110 with arginine, and valine at position 259 with cysteine in the amino acid sequence as shown in SEQ ID NO: 241 was obtained (pUTE100K'-EFP-T5-S98A/K110RN259C).

EXAMPLE 34

(Evaluation of Effects of Improving Substrate Specificity Attained by Introduction of Multiple Mutations Aimed at Improvement of Substrate Specificity into the Amadoriase Gene Derived from *Eupenicillium terrenum*)

The *E. coli* DH5a strains carrying the recombinant plasmids obtained above (i.e., pUTE100K'-EFP-T5-S98A/V259C, pUTE100K'-EFP-T5-K110R/C154N, pUTE100K'-EFP-T5-K110R/V259C, and pUTE100K'-EFP-T5-S98A/K110R/V259C, respectively) were shake-cultured in LB-amp media supplemented with 0.1M IPTG at 30° C. for 18 hours. The resulting cultured strains were suspended in 10 mM potassium phosphate buffer (pH 7.5), the resulting suspension was ultrasonically disintegrated, and the resultant was centrifuged at 20,000×g for 10 minutes to prepare a crude enzyme solution. The crude enzyme solution was subjected to measurement of enzyme activity to α-FV, α-FVH, and ε-FK by the method described in "B. Method of measuring activity" above, and ε-FK/α-FVH and ε-FK/α-FV were determined. Activity was measured using Reagent 1 with a pH adjusted to 8.0. The results are shown in Table 25.

TABLE 25

| Plasmid | Amino acid mutation | Template plasmid | SEQ ID NO: of oligonucleotide | ε-FK/α-FVH | Ratio of ε-FK/α-FVH (%) | ε-FK/α-FV | Ratio of ε-FK/α-FV (%) |
|---|---|---|---|---|---|---|---|
| pUTE100K'-EFP-T5 | None | None | None | 0.107 | 100 | 0.0206 | 100 |
| pUTE100K'-EFP-T5-S98A | S98A | pUTE100K'-EFP-T5 | 243 and 244 | 0.0825 | 77 | 0.0151 | 73 |
| pUTE100K'-EFP-T5-K110R | K110R | pUTE100K'-EFP-T5 | 245 and 246 | 0.0893 | 83 | 0.0204 | 99 |
| pUTE100K'-EFP-T5-V259C | V259C | pUTE100K'-EFP-T5 | 251 and 252 | 0.0333 | 31 | 0.0068 | 33 |
| pUTE100K'-EFP-T5-S98A/V259C | S98A, V259C | pUTE100K'-EFP-T5-V259C | 243 and 244 | 0.0248 | 23 | 0.0058 | 28 |
| pUTE100K'-EFP-T5-K110R/C154N | K110R, C154N | pUTE100K'-EFP-T5-K110R | 247 and 248 | 0.0779 | 73 | 0.0115 | 56 |
| pUTE100K'-EFP-T5-K110R/V259C | K110R, V259C | pUTE100K'-EFP-T5-V259C | 245 and 246 | 0.0267 | 25 | 0.0060 | 29 |
| pUTE100K'-EFP-T5-S98A/K110R/V259C | S98A, K110R, V259C | pUTE100K'-EFP-T5-S98A/V259C | 245 and 246 | 0.0178 | 17 | 0.0047 | 23 |

As shown in Table 25, the ε-FK/α-FVH value and the ε-FK/α-FV value of the amadoriase derived from *Eupenicillium terrenum* into which multiple amino acid substitutions had been introduced were further lowered compared with the values attained by introduction of single amino acid substitution. This demonstrates that reactivity to ε-FK is significantly lowered.

EXAMPLE 35

(Preparation of DNA of Recombinant Plasmid pKK223-3-CFP-T9)

SEQ ID NO: 272 shows an amino acid sequence of an amadoriase derived from the genus *Coniochaeta* into which mutations aimed at improvement of the thermostability (G184D, F265L, N272D, H302R, and H388Y) had been introduced, and it is encoded by the gene as shown in SEQ ID NO: 273.

The *E. coli* JM109 strains (pKK223-3-CFP-T9) comprising the recombinant plasmid of the amadoriase gene derived from the genus *Coniochaeta* (SEQ ID NO: 273) (see WO 2007/125779) were cultured in the same manner as described in Example 1, and the culture product was centrifuged at 10,000×g for 1 minute to collect strains. The recombinant plasmid pKK223-3-CFP-T9 was extracted and purified from the strains using the GenElute Plasmid Mini-Prep Kit (manufactured by Sigma-Aldrich Corporation), and 2.5 μg of DNA of the recombinant plasmid pKK223-3-CFP-T9 was obtained.

(Site-Directed Modification of DNA of Recombinant Plasmid pKK223-3-CFP-T9)

In order to substitute glutamic acid at position 98 with alanine, serine at position 154 with asparagine, and valine at position 259 with cysteine in the amino acid sequence as shown in SEQ ID NO: 272, PCR was carried out using DNA of the recombinant plasmid pKK223-3-CFP-T9 as a template, the synthetic oligonucleotides as shown in SEQ ID NOs: 55 and 56, and KOD-Plus-(Toyobo Co., Ltd.) under the conditions as described in Example 1 above, *E. coli* JM109 strains were transformed, and the nucleotide sequences of DNAs encoding amadoriases in plasmid DNAs of the grown colonies were determined. As a result, the recombinant plasmid encoding the modified amadoriase through substitution of glutamic acid at position 98 with alanine was obtained (pKK223-3-CFP-T9-E98A).

With the use of DNA of pKK223-3-CFP-T9-E98A as a template and the synthetic oligonucleotides as shown in SEQ ID NOs: 139 and 140, the recombinant plasmid encoding a modified amadoriase resulting from substitution of glutamic acid at position 98 with alanine and serine at position 154 with asparagine was obtained in the same manner as described above (pKK223-3-CFP-T9-E98A1S154N).

With the use of DNA of pKK223-3-CFP-T9-E98A/S154N as a template and the synthetic oligonucleotides as shown in SEQ ID NOs: 151 and 152, the recombinant plasmid encoding a modified amadoriase resulting from substitution of glutamic acid at position 98 with alanine, serine at position 154 with asparagine, and valine at position 259 with cysteine was obtained in the same manner as described above (pKK223-3-CFP-T9-E98A/S154N/V259C).

The *E. coli* JM109 strains capable of producing modified amadoriases obtained in the manner described above were cultured by the method described in Example 1 (3), and 0.6 ml each of crude enzyme solutions of various types of modified amadoriases were prepared.

The enzyme solutions thus obtained were subjected to measurement of enzyme activity to α-FVH, α-FV, and ε-FK by the method described in "B. Method of measuring activity" above, and ε-FK/α-FVH and ε-FK/α-FV were determined. Activity was measured using Reagent 1 (i.e., a peroxidase-4-amino antipyrine solution) with a pH adjusted to 7.0. The results are shown in Table 26.

TABLE 26

| Plasmid | Amino acid mutation | ε-FK/α-FVH | Ratio of ε-FK/α-FVH (%) | ε-FK/α-FV | Ratio of ε-FK/α-FV (%) |
|---|---|---|---|---|---|
| pKK223-3-CFP-T9 | None | 0.0271 | 100 | 0.081 | 100 |
| pKK223-3-CFP-T9-E98A/S154N/V259C | E98A, S154N, V259C | 0.017 | 6 | 0.007 | 8 |

The ε-FK/α-FVH value and the α-FK/α-FV value of the modified amadoriases shown in Table 26 into which multiple amino acid substitutions had been introduced were lowered at significant levels compared with those before mutation. This demonstrates that accumulation of single mutations effective for improving substrate specificity of the amadoriase comprising the amino acid sequence as shown in SEQ ID NO: 1 in the amadoriase comprising the amino acid sequence as shown in SEQ ID NO: 272 can remarkably improve the substrate specificity.

The invention claimed is:

1. A modified amadoriase comprising an amino acid sequence that is at least 95% identical to the amino acid sequence as shown in SEQ ID NO: 1, and comprising one or more amino acid substitutions at positions corresponding to the amino acid sequence of SEQ ID NO: 1, selected from the group consisting of:

(a) substitution of glutamic acid at position 98 with glutamine, histidine, lysine, arginine, glycine, alanine, valine, isoleucine, leucine, methionine, cysteine, serine, threonine, asparagine, aspartic acid, phenylalanine, tyrosine, or tryptophan;

(b) substitution of valine at position 259 with alanine, cysteine, or serine;

(c) substitution of serine at position 154 with glycine, tyrosine, asparagine, glutamine, aspartic acid, glutamic acid, histidine, or cysteine;

(d) substitution of histidine at position 125 with alanine, leucine, phenylalanine, tyrosine, asparagine, glutamine, glutamic acid, lysine, or arginine;
(e) substitution of tyrosine at position 261 with alanine, leucine, phenylalanine, tryptophan, or lysine;
(f) substitution of glycine at position 263 with lysine, arginine, histidine, aspartic acid, or glutamic acid;
(g) substitution of aspartic acid at position 106 with an amino acid having a lower molecular weight than aspartic acid, selected from the group consisting of glycine, alanine, serine, valine, threonine, cysteine, leucine, isoleucine, and asparagine;
(h) substitution of glycine at position 103 with lysine, arginine, or histidine;
(i) substitution of alanine at position 355 with lysine, arginine, histidine, aspartic acid, or glutamic acid;
(j) substitution of aspartic acid at position 96 with alanine, asparagine, histidine, or serine;
(k) substitution of lysine at position 66 with glycine and/or valine at position 67 with proline;
(l) substitution of glutamine at position 70 with proline;
(m) substitution of threonine at position 100 with arginine;
(n) substitution of glutamine at position 110 with alanine, leucine, methionine, phenylalanine, tryptophan, asparagine, histidine, lysine, or arginine;
(o) substitution of alanine at position 113 with glutamic acid or lysine;
(p) substitution of leucine at position 114 with lysine or arginine; and
(q) substitution of aspartic acid at position 156 with asparagine, wherein the modified amadoriase exhibits:
(i) a lower reactivity to ε-fructosyl lysine relative to the reactivity to α-fructosyl valyl histidine compared with an amadoriase comprising the amino acid sequence as shown in SEQ ID NO: 1; or
(ii) a lower reactivity to ε-fructosyl lysine relative to the reactivity to α-fructosyl valine compared with an amadoriase comprising the amino acid sequence as shown in SEQ ID NO: 1.

2. The modified amadoriase according to claim 1 comprising one or more amino acid substitutions selected from the group consisting of:
(a) substitution of an amino acid at a position corresponding to glutamic acid at position 98 with alanine, substitution of an amino acid at a position corresponding to serine at position 154 with asparagine, and substitution of an amino acid at a position corresponding to valine at position 259 with cysteine;
(b) substitution of an amino acid at a position corresponding to glutamic acid at position 98 with arginine and substitution of an amino acid at a position corresponding to serine at position 154 with asparagine;
(c) substitution of an amino acid at a position corresponding to glutamic acid at position 98 with glutamine and substitution of an amino acid at a position corresponding to valine at position 259 with alanine;
(d) substitution of an amino acid at a position corresponding to glutamic acid at position 98 with arginine and substitution of an amino acid at a position corresponding to valine at position 259 with cysteine; and
(e) substitution of an amino acid at a position corresponding to glutamine at position 110 with arginine, substitution of an amino acid at a position corresponding to serine at position 154 with asparagine, and substitution of an amino acid at a position corresponding to valine at position 259 with alanine.

3. A modified amadoriase comprising the amino acid sequence of SEQ ID NO: 272, and consisting of at least one substitution selected from the group consisting of:
(a) a substitution of glutamic acid at position 98 with alanine;
(b) a substitution of serine at position 154 with asparagine; and
(c) a substitution of valine at position 259 with cysteine, wherein the modified amadoriase exhibits a lowered reactivity to ε-fructosyl lysine relative to the reactivity to α-ftuctosyl valyl histidine and a lowered reactivity to ε-fructosyl lysine relative to the reactivity to α-fructosyl valine compared with an amadoriase comprising SEQ ID NO:272.

4. A modified amadoriase comprising the amino acid sequence of SEQ ID NO: 241, and consisting of at least one substitution selected from the group consisting of:
(a) a substitution of serine at position 98 with alanine, substitution of lysine at position 110 with arginine, and substitution of valine at position 259 with cysteine;
(b) a substitution of serine at position 98 with alanine and substitution of valine at position 259 with cysteine; and
(c) a substitution of lysine at position 110 with arginine and substitution of valine at position 259 with cysteine,
and wherein the modified amadoriase exhibits a lowered reactivity to ε-fructosyl lysine relative to the reactivity to α-fructosyl valyl histidine and a lowered reactivity to ε-fructosyl lysine relative to the reactivity to α-fructosyl valine compared with an amadoriase comprising SEQ ID NO: 241.

5. A nucleic acid encoding the amino acid sequence according to claim 1.

6. A recombinant vector comprising the nucleic acid according to claim 5.

7. A host cell comprising the recombinant vector according to claim 6.

8. A method for producing an amadoriase, comprising the following steps:
(a) culturing the host cell according to claim 7;
(b) expressing the amadoriase gene contained in the host cell; and
(c) isolating the amadoriase from the culture product.

9. A kit used for measuring glycated hemoglobin, comprising the amadoriase according to claim 1.

* * * * *